(12) United States Patent
Guerinot et al.

(10) Patent No.: US 7,189,891 B2
(45) Date of Patent: Mar. 13, 2007

(54) ISOLATED FERRIC REDUCTASE DEFECTIVE POLYPEPTIDES AND USES THEREOF

(75) Inventors: Mary Lou Guerinot, Etna, NH (US); Elizabeth E. Rogers, Columbia, MI (US)

(73) Assignee: The Trustees of Dartmouth College, Hanover, NH (US)

( * ) Notice: Subject to any disclaimer, the term of this patent is extended or adjusted under 35 U.S.C. 154(b) by 271 days.

(21) Appl. No.: 10/672,282

(22) Filed: Sep. 25, 2003

(65) Prior Publication Data

US 2004/0154056 A1 Aug. 5, 2004

Related U.S. Application Data

(63) Continuation of application No. PCT/US02/09962, filed on Mar. 27, 2002.

(60) Provisional application No. 60/280,621, filed on Mar. 30, 2001.

(51) Int. Cl.
*C12N 15/00* (2006.01)
*C12N 15/82* (2006.01)
*A01H 5/00* (2006.01)
*C07K 14/00* (2006.01)

(52) U.S. Cl. ............... 800/278; 800/298; 530/370; 435/468

(58) Field of Classification Search .......... 530/370; 800/278, 298, 69.1; 435/278, 298, 69.1
See application file for complete search history.

(56) References Cited

U.S. PATENT DOCUMENTS 5,846,821 A 12/1998 Guerinot et al.

*Primary Examiner*—Medina A. Ibrahim
(74) *Attorney, Agent, or Firm*—Lahive & Cockfield, LLP; Giulio A. DeConti, Jr. Esq.

(57) ABSTRACT

Novel molecules of the multi-drug and toxin efflux (MATE) family of molecules, designated herein as mutant ferric reductase defective (FRD3) nucleic acid and protein molecules are disclosed. The FRD3 nucleic acid and protein molecules are useful as modulating agents in regulating metal homeostasis, e.g., iron homeostasis. The invention further describes transgenic plants in which expression of a FRD3 polypeptide of the invention is altered. Compositions containing FRD3 molecules and methods of using such molecules are also provided.

8 Claims, 32 Drawing Sheets

FIG. 1A frd3-1cDNA.seq Length: 1868 March 29, 2001 12:57
Type: N Check: 5408

```
   1  AAATAATCCC CTCTAAACTC TCCTAGATAC TCACTCATCA CTACTCATCT
  51  CAAGTTCACG TGACTACTTA TATAAGCGTT GACTACATAA AGAGACAGTT
 101  ACAGAGGAAA AAGATCTATG acggaaactg gtgatgatct tgctacggtg
 151  aagaagccaa tcccatttct cgttatcttc aaagatttaa gacatgtatt
 201  cagtagggac acaactgggc gagagattct aggcatcgcg tttccagcag
 251  ctttggcttt agctgctgat ccaatcgatt ctctgattga taccgctttt
 301  gtcgggcgtt taggagcggt tcagctagcg gcggttggag tttccattgc
 351  catattcaat caagcttcta gaattacgat atcccactt gtgagcctca
 401  caacttcatt tgtggcagag aagacacga tggagaagat gaaagaagaa
 451  gcaaacaaag ccaatcttgt tcatgcagaa actatacttg ttcaagattc
 501  tttggaaaag ggcatttctt cacctacaag taacgatacc aaccagccac
 551  agcaacctcc agctccggat acaaagtcaa atagcggaaa caaatcgaat
 601  aaaaaggaga agaggaccat tagaacagca tcaacagcta tgatcttggg
 651  gttaatcctt ggccttgtgc aagctatttt cttgattttc agttcaaagt
 701  tgcttctagg cgtcatggga gtgaaaccaa attcaccaat gttatcacca
 751  gcacacaagt acttgagcat acgagctttg ggggctcctg cattgcttct
 801  atctcttgct atgcaaggca tctttcgtgg attcaaggac accaaaactc
 851  ctctctttgc cactgtcgta gcagatgtta tcaacatagt tctcgacccc
 901  atcttcattt tgtgcttcg tctagggatc atcggtgcag ccattgccca
 951  tgtcatttct cagtacttca tgactctaat attgttcgtc ttcctcgcaa
1001  agaaagttaa tttgattcca ccaaacttcg gggatttgca gtttggaagg
1051  ttccttaaaa atgggctact attgctggcg aggaccatag cagtgacgtt
1101  ttgtcagacc ttagcagcag caatggcggc gcggctgggt acaacaccaa
```

FIG.1B

```
1151  tggctgcttt tcagatttgt ttacaagtat ggttaacttc ttctcttctc
1201  aatgatggtc ttgccgttgc tggtcaggcg attctggctt gttcgtttgc
1251  tgagaaggac tataacaaag tgactgctgt tgcatcccgt gttctacaga
1301  tgggttttgt gttaggactt ggactgtccg ttttttgttgg actaggtctc
1351  tactttggtg ccggagtttt ctccaaggac cctgctgtta ttcacctcat
1401  ggccatcgga ataccgttta tagcagcaac gcagccaata aactctctcg
1451  cctttgtatt ggatggagtc aattttggag catctgattt tgcttacact
1501  gcatactcca tggtgggagt ggcggccata agcattgcag cagtaatata
1551  tatggcaaag accatggtt tcataggaat atggatagct cttacaatct
1601  atatggctct ccgggctatt actggaattg ccaggatggc gacaggaact
1651  ggaccgtgga ggttcttgcg tggacgatca tcctcttcat cttcctagGA
1701  CTTAGTTTAT TTATAACGAG TTGCATCTCT TCTTCCTTCT TCGTTTTTGT
1751  TTATGGTTCT TGTGTTTGTT TTTCAACATT TTGTTCGAGA GACCGTTATC
1801  ATATTATCAG TTTCACATAA ATAATGCATA TTTTTAAGTC ATTAAAATAA
1851  AAAAAAAAAA AAAAAAA
```

FIG. 2A frd3-2cDNA.seq Length: 1867 March 29,2001 12:57 Type: N
Check: 3343

```
   1 AAATAATCCC CTCTAAACTC TCCTAGATAC TCACTCATCA CTACTCATCT
  51 CAAGTTCACG TGACTACTTA TATAAGCGTT GACTACATAA AGAGACAGTT
 101 ACAGAGGAAA AAGATCTATG acggaaactg gtgatgatct tgctacggtg
 151 aagaagccaa tcccatttct cgttatcttc aaagatttaa gacatgtatt
 201 cagtagggac acaactgggc gagagattct aggcatcgcg tttccagcag
 251 ctttggcttt agctgctgat ccaatcgctt ctctgattga taccgctttt
 301 gtcgggcgtt taggagcggt tcagctagcg gcggttggag tttccattgc
 351 catattcaat caagcttcta gaattacgat attcccactt gtgagcctca
 401 caacttcatt tgtggcagag gaagacacga tggagaagat gaaagaagaa
 451 gcaaacaaag ccaatcttgt tcatgcagaa actatacttg ttcaagattc
 501 tttggaaaag ggcatttctt cacctacaag taacgatacc aaccagccac
 551 agcaacctcc agctccggat acaaagtcaa atagcggaaa caaatcgaat
 601 aaaaggaga agaggaccat tagaacagca tcaacagcta tgatcttggg
 651 gttaatcctt ggccttgtgc aagctatttt cttgattttc agttcaaagt
 701 tgcttctagg cgtcatggga gtgaaaccaa attcaccaat gttatcacca
 751 gcacacaagt acttgagcat acgagctttg ggggctcctg cattgcttct
 801 atctcttgct atgcaaggca tctttcgtgg attcaaggac accaaaactc
 851 ctctctttgc cactgtcgta gcagatgtta tcaacatagt tctcgacccc
 901 atcttcattt tgtgcttcg tctagggatc atcggtgcag ccattgccca
 951 tgtcatttct cagtacttca tgactctaat attgttcgtc ttcctcgcaa
1001 agaaagttaa tttgattcca ccaaacttcg gggatttgca gtttggaagg
1051 ttccttaaaa atgggctact attgctggcg aggaccatag cagtgacgtt
1101 ttgtcagacc ttagcagcag caatggcggc gcggctgggt acaacaccaa
```

FIG. 2B

```
1151  tggctgtttt cagatttgtt tacaagtatg gttaacttct tctcttctca
1201  atgatggtct tgccgttgct ggtcaggcga ttctggcttg ttcgtttgct
1251  gagaaggact ataacaaagt gactgctgtt gcatcccgtg ttctacagat
1301  gggttttgtg ttaggacttg gactgtccgt ttttgttgga ctaggtctct
1351  actttggtgc cggagttttc tccaaggacc ctgctgttat tcacctcatg
1401  gccatcggaa taccgtttat agcagcaacg cagccaataa actctctcgc
1451  ctttgtattg gatggagtca attttggagc atctgatttt gcttacactg
1501  catactccat ggtgggagtg gcggccataa gcattgcagc agtaatatat
1551  atggcaaaga ccaatggttt cataggaata tggatagctc ttacaatcta
1601  tatggctctc cgggctatta ctggaattgc caggatggcg acaggaactg
1651  gaccgtggag gttcttgcgt ggacgatcat cctcttcatc ttcctagGAC
1701  TTAGTTTATT TATAACGAGT TGCATCTCTT CTTCCTTCTT CGTTTTTGTT
1751  TATGGTTCTT GTGTTTGTTT TTCAACATTT TGTTCGAGAG ACCGTTATCA
1801  TATTATCAGT TTCACATAAA TAATGCATAT TTTTAAGTCA TTAAAATAAA
1851  AAAAAAAAAA AAAAAA
```

FIG.3A manlcDNA.seq  Length: 1950  March 29, 2001 12:56  Type: N  Check: 2367

```
   1 AAATAATCCC CTCTAAACTC TCCTAGATAC TCACTCATCA CTACTCATCT
  51 CAAGTTCACG TGACTACTTA TATAAGCGTT GACTACATAA AGAGACAGTT
 101 ACAGAGGAAA AAGATCTATG acggaaactg gtgatgatct tgctacggtg
 151 aagaagccaa tcccatttct cgttatcttc aaagatttaa gacatgtatt
 201 cagtagggac acaactgggc gagagattct aggcatcgcg tttccagcag
 251 ctttggcttt agctgctgat ccaatcgctt ctctgattga taccgctttt
 301 gtcgggcgtt taggagcggt tcagctagcg gcggttggag tttccattgc
 351 catattcaat caagcttcta gaattacgat attcccactt gtgagcctca
 401 caacttcatt tgtggcagag gaagacacga tggagaagat gaaagaagaa
 451 gcaaacaaag ccaatcttgt tcatgcagaa actatacttg ttcaagattc
 501 tttggaaaag ggcatttctt cacctacaag taacgatacc aaccagccac
 551 agcaacctcc agctccggat acaaagtcaa atagcggaaa caaatcgaat
 601 aaaaaggaga agaggaccat tagaacagca tcaacagcta tgatcttggg
 651 gttaatcctt ggccttgtgc aagctatttt cttgattttc agttcaaagt
 701 tgcttctagg cgtcatggga gtgaaaccaa attcaccaat gttatcacca
 751 gcacacaagt acttgagcat acgagctttg ggggctcctg cattgcttct
 801 atctcttgct atgcaaggca tctttcgtgg attcaaggac accaaaactc
 851 ctctctttgc cactgataat taagttggta acttagatca tctttaatga
 901 tcactctcct tacttcttat aatattttgc cttaatgcgt gaaacagtcg
 951 tagcagatgt tatcaacata gttctcgacc ccatcttcat ttttgtgctt
1001 cgtctaggga tcatcggtgc agccattgcc catgtcattt ctcagtactt
1051 catgactcta atattgttcg tcttcctcgc aaagaaagtt aatttgattc
1101 caccaaactt cggggatttg cagtttggaa ggttccttaa aaatgggcta
1151 ctattgctgg cgaggaccat agcagtgacg ttttgtcaga ccttagcagc
1201 agcaatggcg gcgcggctgg gtacaacacc aatggctgct ttcagattt
1251 gtttacaagt atggttaact tcttctcttc tcaatgatgg tcttgccgtt
```

FIG. 3B

```
1301  gctggtcagg cgattctggc ttgttcgttt gctgagaagg actataacaa 1351  agtgactgct gttgcatccc gtgttctaca gatgggtttt gtgttaggac 1401  ttggactgtc cgttttttgtt ggactaggtc tctactttgg tgccggagtt 1451  ttctccaagg accctgctgt tattcacctc atggccatcg aataccgtt 1501  tatagcagca acgcagccaa taaactctct cgcctttgta ttggatggag 1551  tcaatttttgg agcatctgat tttgcttaca ctgcatactc catggtggga 1601  gtggcggcca taagcattgc agcagtaata tatatggcaa agaccaatgg 1651  tttcatagga atatggatag ctcttacaat ctatatggct ctccgggcta 1701  ttactggaat tgccaggatg gcgacaggaa ctggaccgtg gaggttcttg 1751  cgtggacgat catcctcttc atcttcctag GACTTAGTTT ATTTATAACG

1801  AGTTGCATCT CTTCTTCCTT CTTCGTTTTT GTTTATGGTT CTTGTGTTTG

1851  TTTTTCAACA TTTTGTTCGA GAGACCGTTA TCATATTATC AGTTTCACAT

1901  AAATAATGCA TATTTTTAAG TCATTAAAAT AAAAAAAAAA AAAAAAAAA
```

FIG. 4 wild typ FRD3 amino acid sequence
MTETGDDLATVKKPIPFLVIFKDLRHVFSRDTTGRE<u>ILGIAFPAALALAAD</u>
<u>PIASLIDTAFVGRLGAVQLAAVGVSIAIF</u>NQASRITIFPLVSLTTSFVAEE
DTMEKMKEEANKANLVHAETILVQDSLEKGISSPTSNDTNQPQQPPAPDTK
SNSGNKSNKKEKRTIRTAS<u>TAMILGLILGLVQAIFLIFSSKLLL</u>GVMGVKP
NSPMLSPAHK<u>YLSIRALGAPALLLSLAMQGIFRGFKDTKTPLFATVVADVI</u>
<u>NIVLDPIFIFVLRLGIIGAAIAHVISQYFMTLILFVFLAKKV</u>NLIPPNFGDL
QFGRFLK<u>NGLLLLARTIAVTFCQTLAAAMAARL</u>GTTPMAAFQICLQV<u>WLTSS</u>
<u>LLNDGLAVAGQA1LACSFAEKDYNKVTAVASRVLQ</u>M<u>GFVLGLGLSVFVGLGL</u>
<u>YFGAGVFSKDPAVIHLMAIGIPF1AATQP</u>IN<u>SLAFVLDGVNFGASDFAYTAY</u>
<u>SMVGVAAIS1AAVIYMAKTNGFIGIWIALTIYMALRAITGIAR</u>MATGTGPWR
FLRGRSSSSSS

Frd3-1 amino acid sequence
MTETGDDLATVKKPIPFLVIFKDLRHVFSRDTTGREILGIAFPAALALAAD
PIDSLIDTAFVGRLGAVQLAAVGVSIAIFNQASRITIFPLVSLTTSFVAEE
DTMEKMKEEANKANLVHAETILVQDSLEKGISSPTSNDTNQPQQPPAPDTK
SNSGNKSNKKEKRTIRTASTAMILGLILGLVQAIFLIFSSKLLLGVMGVKP
NSPMLSPAHKYLS1RALGAPALLLSLAMQGIFRGFKDTKTPLFATVVADVI
NIVLDPIFIFVLRLGIIGAAIAHVISQYFMTLILFVFLAKKVNLIPPNFGDL
QFGRFLKNGLLLLARTIAVTFCQTLAAAMAARLGTTPMAAFQICLQVWLTSS
LLNDGLAVAGQA1LACSFAEKDYNKVTAVASRVLQMGFVLGLGLSVFVGLGL
YFGAGVFSKDPAVIHLMAIGIPF1AATQPINSLAFVLDGVNFGASDFAYTAY
SMVGVAAIS1AAVIYMAKTNGFIGIWIALTIYMALRAITGIARMATGTGPWR
FLRGRSSSSSS

Frd3-2 amino acid sequence
MTETGDDLATVKKPIPFLVIFKDLRHVFSRDTTGREILGIAFPAALALAAD
PIASLIDTAFVGRLGAVQLAAVGVSIAIFNQASRITIFPLVSLTTSFVAEE
DTMEKMKEEANKANLVHAETILVQDSLEKGISSPTSNDTNQPQQPPAPDTK
SNSGNKSNKKEKRTIRTASTAMILGLILGLVQAIFLIFSSKLLLGVMGVKP
NSPMLSPAHKYLSIRALGAPALLLSLAMQGIFRGFKDTKTPLFATVVADVI
NIVLDPIFIFVLRLGIIGAAIAHVISQYFMTLILFVFLAKKVNLIPPNFGDL
QFGRFLKNGLLLLARTIAVTFCQTLAAAMAARLGTTPMAAFVRFVYKYG

Man1 amino acid sequence
MTETGDDLATVKKPIPFLVIFKDLRHVFSRDTTGREILGIAFPAALALAAD
PIASLIDTAFVGRLGAVQLAAVGVSIAIFNQASRITIFPLVSLTTSFVAEE
DTMEKMKEEANKANLVHAETILVQDSLEKGISSPTSNDTNQPQQPPAPDTK
SNSGNKSNKKEKRTIRTASTAMILGLILGLVQAIFLIFSSKLLLGVMGVKP
NSPMLSPAHKYLS1RALGAPALLLSLAMQGIFRGFKDTKTPLFATDN

FIG. 5A frd3-1.seq  Length: 5738  March 29, 2001  13:14  Type: N  Check: 5605

```
    1  tttctacata ttttgattc catttcata agaaaatctt cagtatatta
   51  ttacattcat atttattact tctttattat ttaaagtgat cattccaatt
  101  ttatatatag aaaattattt atttatttat ggcaaggttg caacatataa
  151  aaaaaaagtt ggtatacaaa caaatatcta aaataatccc ctctaaactc
  201  tcctagatac tcactcatca ctactcatct caagttcacg tgactactta
  251  tataagcgtt gactacataa aggtaagata ttctctccac atatctcata
  301  agttctatga tttttcttag tattgcatat atgttctcta tcctactagg
  351  atatatcaac acaacataca caagttctca attgaattag aagctcatga
  401  gtaactataa ctgtatatat agttaactag attacgagta agaatgcaat
  451  tgtaaagcct tttaattgaa cttcttcttc tttttttgat aaaaggtttt
  501  taattaaaaa aacaagtaat taaccattac aagctaggac aactaagtca
  551  tacatgttga gagtagtgag agagttaagc aaaagcttaa tctagtcctt
  601  ttaaaagcta acaaacatag tagagattat aagatgtttg gtgtaaataa
  651  caacaatacc cagtttgtac atgtgtttag aaaatagttt ggattatggt
  701  ctaaaatata taaattataa gaaagatgat gtctaacgat tcaacatagc
  751  aaaagatgat gtacacaaat gtttttgttt tacccatgta aaaaaacaga
  801  acattagttg ttaagtttat aggtttattt tctacattaa ttttcacaac
  851  tttttagtac cagaacgcac aatcaattaa gttttcatct tctatatata
  901  ctgatctaaa aatattaata taaggtttgg gataattcaa tttaatcaca
  951  tcgtttataa aaagcggtta actctacgat aactaaataa attgtgttat
 1001  atgaaaaggg gaagtggcaa tgtaggtaat ggaattgacg ttgatggctt
 1051  gaaaagatg gccttatctt gcggaacaaa caattacata cacgacacgc
 1101  actatataca actcacctgt gttggtctct gttgccatct tttatgttat
```

FIG. 5B

```
1151  tgttttccga ctgtcgcctt cctttaacta atattataat tttaaagatg
1201  ttcataaatc acagtagaaa gcttgttttt gctaaaatga acatgacacg
1251  gatcatacaa aaaatatatt ttacactata gctatatacc gatttaatct
1301  taggtacttt gaatcgtgct aaaactaaac ggccttctca aaaccctccc
1351  tcttttcctc cctccctcag aaaccctcc atcgacaaat aacgttatgc
1401  aattctctaa acaatgctcg acaagcatgt gttttagta atgctacaac
1451  ttatttctct tttcaacgtc ctaagaggca tcaaaaagat caaagatctt
1501  ggaaccgagg tcctatgcaa ggaatcatta taaagtacca tgttattttt
1551  ttaaataaca tcgttttctt aatataattt ataaataccg ttatttttac
1601  cgaaatttca tatatatgtc agttttatac tttgtacgat aacgccaaaa
1651  actttaatta tcgccaaaat tgtaaacggt attttcgtcg tttagttatt
1701  taccaaaaat aaaatgacga ttgcaactta tttagttaaa atacaaaaaa
1751  aaactaatat attaattgag cggacggaat ttttttccaa aatcccgatg
1801  tgtaaatatg agaacgtttc gaggataact tacaaattaa acattaataa
1851  aaatgataaa gtgtagttag gagctaaatt gtgatagtaa acatctatct
1901  ctaatattat taaatgaatt ataatactat tttaatcata gtattaaatt
1951  tctttaatta aaaatataaa taatttcaat ttaattctat accaaattaa
2001  cccgaaaata ttttatctaa catacacaaa gacacataaa agttttgata
2051  actgcctaaa aaaataagct tttgaattat taattagttg ttattcaatg
2101  ataaaataac attatttgtc aactagtgaa ttccaattac gcaaaatgat
2151  tcactttttt agtggaaaat atcaaagaaa aatgagaagt ttatatgaaa
2201  ataaactctt tcccactatg atgaatacat gtaagaaaac tttcatgaaa
2251  agaaaactta tttactcaat ataaaatag aagactcttt atctttcacg
2301  agtaaagtt cacgaaaacc atatttcct attgattaaa gaaatcatag
2351  aagttaaaat aatcaacaag ggcaagccaa aaacttctag tgtgggattt
2401  acttaataga agtatatata ttacgatgtt tatgcgtacc tatttcccct
2451  caatgagaag agaaattcca taatattggt gtcttaagtt tggacggaaa
```

FIG. 5C

```
2501  taaagagcag caaaaaagtt agggaaggaa acctttgttt tcttcaataa
2551  ttatagaaaa taatttcttt tattgattta gatattaaat aagcaaagat
2601  atgcatgctc attacgtgtc tataaataaa aacacgtttg tacatagcat
2651  ctactataaa cgttcctttt gcttccccga ttcttcgaaa cacttattga
2701  tatcttcaga cacaacaaat taattacaga gacagttaca gaggaaaaag
2751  atctatgacg gaaactggtg atgatcttgc tacggtgaag aagccaatcc
2801  catttctcgt tatcttcaaa gatttaaggt gtgtgtttat gtattcatga
2851  aatggtgatg aaattttga aagaagtgat gcataacatt agtttattta
2901  tgtaaaattg cagacatgta ttcagtaggg acacaactgg gcgagagatt
2951  ctaggcatcg cgtttccagc agctttggct ttagctgctg atccaatcga
3001  ttctctgatt gataccgctt tgtcgggcg tttaggagcg gttcagctag
3051  cggcggttgg agtttccatt gccatattca atcaagcttc tagaattacg
3101  atattcccac ttgtgagcct cacaacttca tttgtggcag aggaagacac
3151  gatggagaag atgaagaag aagcaaacaa agccaatctt gttcatgcag
3201  aaactatact tgttcaagat tctttggaaa agggcatttc ttcacctaca
3251  agtaacgata ccaaccagcc acagcaacct ccaggtaaat tccgcatatc
3301  tcactcgaca tgataactt ttattaaagt ttcgattgtt tttttactgt
3351  tggtttcttc tctcgatctc ttttgtttca atttgttgtt tttttggttg
3401  tattaaactt agctccggat acaaagtcaa atagcggaaa caaatcgaat
3451  aaaaaggaga agaggaccat tagaacagca tcaacagcta tgatcttggg
3501  gttaatcctt ggccttgtgc aagctatttt cttgattttc agttcaaagt
3551  tgcttctagg cgtcatggga gtgaaaccag taagttttca gaaatataca
3601  tattttgttg ggatctatag cataaaatgt tttgactaat ttgagttgaa
3651  tttggataac agaattcacc aatgttatca ccagcacaca agtacttgag
3701  catacgagct ttgggggctc ctgcattgct tctatctctt gctatgcaag
3751  gcatctttcg tggattcaag gacaccaaaa ctcctctctt tgccactggt
3801  aattaagttg ttaacttaga tcatctttaa tgatcactct ccttacttct
```

FIG. 5D

```
3851  tataatattt tgccttaatg cgtgaaacag tcgtagcaga tgttatcaac
3901  atagttctcg acccatctt cattttgtg cttcgtctag ggatcatcgg
3951  tgcagccatt gcccatgtca tttctcagta agagaaatca ctaaaaaaat
4001  tccacacatg caaaagtgat cattattgaa caaaatcgct aggcgcactc
4051  ttgtttttct acagctataa atagacttgt gaagtcataa cctcaaacaa
4101  aaacaaatga tttgtttgtg tacgtgaagg tacttcatga ctctaatatt
4151  gttcgtcttc ctcgcaaaga aagttaattt gattccacca aacttcgggg
4201  atttgcagtt tggaaggttc cttaaaaatg gtacgtatgg atgcatattt
4251  attaaaagtt gtggttcttg caataatatt ttttttaaa aacaagatcc
4301  gtcgtaggag ctaatgcaca gagtccaaaa ataaattaac aaaaaattta
4351  tctatataat aatagaattc aatcaaataa ggtctatatt taaaatattg
4401  aatattttga aatatatagt taagaaaatg agaaatgtgg atatatgtct
4451  aacaagtata gtattaaaaa tgaaagggct actattgctg gcgaggacca
4501  tagcagtgac gttttgtcag accttagcag cagcaatggc ggcgcggctg
4551  ggtacaacac caatggctgc ttttcagatt tgtttacaag tatggttaac
4601  ttcttctctt ctcaatgatg gtcttgccgt tgctggtcag gtaatcatgt
4651  tttctcgttg tattaattta tgtatagttt atatggttga tcaagttgta
4701  tgtagaaaat gatcattcaa tacgttgcag gcgattctgg cttgttcgtt
4751  tgctgagaag gactataaca aagtgactgc tgttgcatcc cgtgttctac
4801  aggttcggtc caaaaatcac attaccaaac ctttctttaa aaataaaata
4851  attgtgtaac taaaacagaa atgaatttga tacgcagatg ggttttgtgt
4901  taggacttgg actgtccgtt tttgttggac taggtctcta ctttggtgcc
4951  ggagttttct ccaaggaccc tgctgttatt cacctcatgg ccatcggaat
5001  accggtaact aataatcaaa taataattac tatagtataa aaatcatttt
5051  aaaagaattt tactaatgag aagaggttat atatatttat gcagtttata
5101  gcagcaacgc agccaataaa ctctctcgcc tttgtattgg atggagtcaa
5151  ttttggagca tctgattttg cttacactgc atactccatg gtatgcacac
```

FIG. 5E

```
5201  tatatatact atgaaatgat taaaattcct ttttttttt ttgaaatgac
5251  ttaaactttg tctatctttt tttcttgtaa tccaattatg ataaatcagg
5301  tgggagtggc ggccataagc attgcagcag taatatatat ggcaaagacc
5351  aatggtttca taggaatatg gatagctctt acaatctata tggctctccg
5401  ggctattact ggaattgcca ggtatttaaa ttgggccttt actatagccc
5451  actatagtag aagcagtatt tgactgagtg tttgaattta tgcaggatgg
5501  cgacaggaac tggaccgtgg aggttcttgc gtggacgatc atcctcttca
5551  tcttcctagg acttagttta tttataacga gttgcatctc ttcttccttc
5601  ttcgttttg tttatggttc ttgtgtttgt ttttcaacat tttgttcgag
5651  agaccgttat catattatca gtttcacata aataatgcat attttaagt
5701  cattaaaata tggagccctc tgccctcact ggcttttc
```

FIG.6A frd3-2.seq Length: 5737 March 29, 2001 13:14 Type: N Check: 374

```
   1  tttctacata tttttgattc catttcata agaaaatctt cagtatatta
  51  ttacattcat atttattact tctttattat ttaaagtgat cattccaatt
 101  ttatatatag aaaattattt atttatttat ggcaaggttg caacatataa
 151  aaaaaaagtt ggtatacaaa caaatatcta aaataatccc ctctaaactc
 201  tcctagatac tcactcatca ctactcatct caagttcacg tgactactta
 251  tataagcgtt gactacataa aggtaagata ttctctccac atatctcata
 301  agttctatga tttttcttag tattgcatat atgttctcta tcctactagg
 351  atatatcaac acaacataca caagttctca attgaattag aagctcatga
 401  gtaactataa ctgtatatat agttaactag attacgagta agaatgcaat
 451  tgtaaagcct tttaattgaa cttcttcttc ttttttttgat aaaaggtttt
 501  taattaaaaa aacaagtaat taaccattac aagctaggac aactaagtca
 551  tacatgttga gagtagtgag agagttaagc aaaagcttaa tctagtcctt
 601  ttaaaagcta acaaacatag tagagattat aagatgtttg gtgtaaataa
 651  caacaatacc cagtttgtac atgtgtttag aaaatagttt ggattatggt
 701  ctaaaatata taaattataa gaaagatgat gtctaacgat tcaacatagc
 751  aaaagatgat gtacacaaat gttttgttt tacccatgta aaaaaacaga
 801  acattagttg ttaagtttat aggtttattt tctacattaa ttttcacaac
 851  tttttagtac cagaacgcac aatcaattaa gttttcatct tctatatata
 901  ctgatctaaa aatattaata taaggtttgg gataattcaa tttaatcaca
 951  tcgtttataa aaagcggtta actctacgat aactaaataa attgtgttat
1001  atgaaaaggg gaagtggcaa tgtaggtaat ggaattgacg ttgatggctt
1051  gaaaaagatg gccttatctt gcggaacaaa caattacata cacgacacgc
1101  actatataca actcacctgt gttggtctct gttgccatct tttatgttat
```

FIG. 6B

```
1151  tgttttccga ctgtcgcctt cctttaacta atattataat tttaaagatg
1201  ttcataaatc acagtagaaa gcttgttttt gctaaaatga acatgacacg
1251  gatcatacaa aaatatatt ttacactata gctatatacc gatttaatct
1301  taggtacttt gaatcgtgct aaaactaaac ggccttctca aaaccctccc
1351  tcttttcctc cctccctcag aaaccctcc atcgacaaat aacgttatgc
1401  aattctctaa acaatgctcg acaagcatgt gttttagta atgctacaac
1451  ttatttctct tttcaacgtc ctaagaggca tcaaaaagat caaagatctt
1501  ggaaccgagg tcctatgcaa ggaatcatta taaagtacca tgttattttt
1551  ttaataaca tcgttttctt aatataattt ataaataccg ttatttttac
1601  cgaaatttca tatatatgtc agttttatac tttgtacgat aacgccaaaa
1651  actttaatta tcgccaaaat tgtaaacggt attttcgtcg tttagttatt
1701  taccaaaaat aaaatgacga ttgcaactta tttagttaaa atacaaaaaa
1751  aaactaatat attaattgag cggacggaat ttttttccaa aatcccgatg
1801  tgtaaatatg agaacgtttc gaggataact tacaaattaa acattaataa
1851  aaatgataaa gtgtagttag gagctaaatt gtgatagtaa acatctatct
1901  ctaatattat taaatgaatt ataatactat tttaatcata gtattaaatt
1951  tctttaatta aaaatataaa taatttcaat ttaattctat accaaattaa
2001  cccgaaaata ttttatctaa catacacaaa gacacataaa agttttgata
2051  actgcctaaa aaaataagct tttgaattat taattagttg ttattcaatg
2101  ataaaataac attatttgtc aactagtgaa ttccaattac gcaaaatgat
2151  tcacttttt agtggaaaat atcaaagaaa aatgagaagt ttatatgaaa
2201  ataaactctt tcccactatg atgaatacat gtaagaaaac tttcatgaaa
2251  agaaaactta tttactcaat ataaaaatag aagactcttt atctttcacg
2301  agtaaaagtt cacgaaaacc atattttcct attgattaaa gaaatcatag
2351  aagttaaaat aatcaacaag ggcaagccaa aaacttctag tgtgggattt
2401  acttaataga agtatatata ttacgatgtt tatgcgtacc tattttccct
2451  caatgagaag agaaattcca taatattggt gtcttaagtt tggacggaaa
```

FIG. 6C

```
2501  taaagagcag caaaaaagtt agggaaggaa acctttgttt tcttcaataa 2551  ttatagaaaa taatttcttt tattgattta gatattaaat aagcaaagat 2601  atgcatgctc attacgtgtc tataaataaa aacacgtttg tacatagcat 2651  ctactataaa cgttcctttt gcttcccga ttcttcgaaa cacttattga 2701  tatcttcaga cacaacaaat taattacaga gacagttaca gaggaaaaag 2751  atctatgacg gaaactggtg atgatcttgc tacggtgaag aagccaatcc 2801  catttctcgt tatcttcaaa gatttaaggt gtgtgtttat gtattcatga 2851  aatggtgatg aaatttttga aagaagtgat gcataacatt agtttattta 2901  tgtaaaattg cagacatgta ttcagtaggg acacaactgg gcgagagatt 2951  ctaggcatcg cgtttccagc agctttggct ttagctgctg atccaatcgc 3001  ttctctgatt gataccgctt ttgtcgggcg tttaggagcg gttcagctag 3051  cggcggttgg agtttccatt gccatattca atcaagcttc tagaattacg 3101  atattcccac ttgtgagcct cacaacttca tttgtggcag aggaagacac 3151  gatggagaag atgaaagaag aagcaaacaa agccaatctt gttcatgcag 3201  aaactatact tgttcaagat tctttggaaa agggcatttc ttcacctaca 3251  agtaacgata ccaaccagcc acagcaacct ccaggtaaat tccgcatatc 3301  tcactcgaca ttgataactt ttattaaagt ttcgattgtt tttttactgt 3351  tggtttcttc tctcgatctc ttttgtttca atttgttgtt tttttggttg 3401  tattaaactt agctccggat acaaagtcaa atagcggaaa caaatcgaat 3451  aaaaaggaga agaggaccat tagaacagca tcaacagcta tgatcttggg 3501  gttaatcctt ggccttgtgc aagctatttt cttgattttc agttcaaagt 3551  tgcttctagg cgtcatggga gtgaaccag taagttttca gaaatataca 3601  tattttgttg ggatctatag cataaaatgt tttgactaat ttgagttgaa 3651  tttggataac agaattcacc aatgttatca ccagcacaca agtacttgag 3701  catacgagct ttgggggctc ctgcattgct tctatctctt gctatgcaag 3751  gcatctttcg tggattcaag gacaccaaaa ctcctctctt tgccactggt 3801  aattaagttg ttaacttaga tcatctttaa tgatcactct ccttacttct
```

FIG. 6D

```
3851  tataatattt tgccttaatg cgtgaaacag tcgtagcaga tgttatcaac
3901  atagttctcg accccatctt catttttgtg cttcgtctag ggatcatcgg
3951  tgcagccatt gcccatgtca tttctcagta agagaaatca ctaaaaaaat
4001  tccacacatg caaaagtgat cattattgaa caaaatcgct aggcgcactc
4051  ttgtttttct acagctataa atagacttgt gaagtcataa cctcaaacaa
4101  aaacaaatga tttgtttgtg tacgtgaagg tacttcatga ctctaatatt
4151  gttcgtcttc ctcgcaaaga aagttaattt gattccacca aacttcgggg
4201  atttgcagtt tggaaggttc cttaaaaatg gtacgtatgg atgcatattt
4251  attaaaagtt gtggttcttg caataatatt ttttttaaa aacaagatcc
4301  gtcgtaggag ctaatgcaca gagtccaaaa ataaattaac aaaaaattta
4351  tctatataat aatagaattc aatcaaataa ggtctatatt taaaatattg
4401  aatattttga aatatatagt taagaaaatg agaaatgtgg atatatgtct
4451  aacaagtata gtattaaaaa tgaaagggct actattgctg gcgaggacca
4501  tagcagtgac gttttgtcag accttagcag cagcaatggc ggcgcggctg
4551  ggtacaacac caatggctgt tttcagattt gtttacaagt atggttaact
4601  tcttctcttc tcaatgatgg tcttgccgtt gctggtcagg taatcatgtt
4651  ttctcgttgt attaatttat gtatagttta tatggttgat caagttgtat
4701  gtagaaaatg atcattcaat acgttgcagg cgattctggc ttgttcgttt
4751  gctgagaagg actataacaa agtgactgct gttgcatccc gtgttctaca
4801  ggtcggtcc aaaaatcaca ttaccaaacc tttctttaaa aataaaataa
4851  ttgtgtaact aaaacagaaa tgaatttgat acgcagatgg gttttgtgtt
4901  aggacttgga ctgtccgttt tgttggact aggtctctac tttggtgccg
4951  gagttttctc caaggaccct gctgttattc acctcatggc catcggaata
5001  ccggtaacta ataatcaaat aataattact atagtataaa aatcatttta
5051  aaagaatttt actaatgaga agaggttata tatatttatg cagtttatag
5101  cagcaacgca gccaataaac tctctcgcct ttgtattgga tggagtcaat
5151  tttggagcat ctgatttgc ttacactgca tactccatgg tatgcacact
```

FIG. 6E

```
5201  atatatacta tgaaatgatt aaaattcctt tttttttttt tgaaatgact
5251  taaactttgt ctatctcttt ttcttgtaat ccaattatga taaatcaggt
5301  gggagtggcg gccataagca ttgcagcagt aatatatatg gcaaagacca
5351  atggtttcat aggaatatgg atagctctta caatctatat ggctctccgg
5401  gctattactg gaattgccag gtatttaaat tgggccttta ctatagccca
5451  ctatagtaga agcagtattt gactgagtgt ttgaatttat gcaggatggc
5501  gacaggaact ggaccgtgga ggttcttgcg tggacgatca tcctcttcat
5551  cttcctagga cttagtttat ttataacgag ttgcatctct tcttccttct
5601  tcgtttttgt ttatggttct tgtgtttgtt tttcaacatt ttgttcgaga
5651  gaccgttatc atattatcag tttcacataa ataatgcata tttttaagtc
5701  attaaaatat ggagccctct gccctcactg gcttttc
```

FIG. 7A man1.seq Length: 5738  March 29, 2001 13:14  Type: N  Check: 5455

```
    1  tttctacata ttttttgattc cattttcata agaaaatctt cagtatatta
   51  ttacattcat atttattact tctttattat ttaaagtgat cattccaatt
  101  ttatatatag aaaattattt atttatttat ggcaaggttg caacatataa
  151  aaaaaaagtt ggtatacaaa caaatatcta aataatccc  ctctaaactc
  201  tcctagatac tcactcatca ctactcatct caagttcacg tgactactta
  251  tataagcgtt gactacataa aggtaagata ttctctccac atatctcata
  301  agttctatga ttttcttag  tattgcatat atgttctcta tcctactagg
  351  atatatcaac acaacataca caagttctca attgaattag aagctcatga
  401  gtaactataa ctgtatatat agttaactag attacgagta agaatgcaat
  451  tgtaaagcct tttaattgaa cttcttcttc ttttttgat  aaaaggtttt
  501  taattaaaaa aacaagtaat taaccattac aagctaggac aactaagtca
  551  tacatgttga gagtagtgag agagttaagc aaaagcttaa tctagtcctt
  601  ttaaaagcta acaaacatag tagagattat aagatgtttg gtgtaaataa
  651  caacaatacc cagtttgtac atgtgtttag aaaatagttt ggattatggt
  701  ctaaaatata taaattataa gaaagatgat gtctaacgat tcaacatagc
  751  aaaagatgat gtacacaaat gtttttgttt tacccatgta aaaaaacaga
  801  acattagttg ttaagtttat aggtttattt tctacattaa ttttcacaac
  851  tttttagtac cagaacgcac aatcaattaa gttttcatct tctatatata
  901  ctgatctaaa aatattaata taaggtttgg gataattcaa tttaatcaca
  951  tcgtttataa aaagcggtta actctacgat aactaaataa attgtgttat
 1001  atgaaaaggg gaagtggcaa tgtaggtaat ggaattgacg ttgatggctt
 1051  gaaaaagatg gccttatctt gcggaacaaa caattacata cacgacacgc
 1101  actatataca actcacctgt gttggtctct gttgccatct tttatgttat
```

FIG. 7B

```
1151  tgttttccga ctgtcgcctt cctttaacta atattataat tttaaagatg
1201  ttcataaatc acagtagaaa gcttgttttt gctaaaatga acatgacacg
1251  gatcatacaa aaaatatatt ttacactata gctatatacc gatttaatct
1301  taggtacttt gaatcgtgct aaaactaaac ggccttctca aaaccctccc
1351  tcttttcctc cctccctcag aaaccectcc atcgacaaat aacgttatgc
1401  aattctctaa acaatgctcg acaagcatgt gttttagta atgctacaac
1451  ttatttctct tttcaacgtc ctaagaggca tcaaaaagat caaagatctt
1501  ggaaccgagg tcctatgcaa ggaatcatta taaagtacca tgttattttt
1551  ttaaataaca tcgttttctt aatataattt ataaataccg ttatttttac
1601  cgaaatttca tatatatgtc agttttatac tttgtacgat aacgccaaaa
1651  actttaatta tcgccaaaat tgtaaacggt attttcgtcg tttagttatt
1701  taccaaaaat aaaatgacga ttgcaactta tttagttaaa atacaaaaaa
1751  aaactaatat attaattgag cggacggaat ttttttccaa aatcccgatg
1801  tgtaaatatg agaacgtttc gaggataact tacaaattaa acattaataa
1851  aaatgataaa gtgtagttag gagctaaatt gtgatagtaa acatctatct
1901  ctaatattat taaatgaatt ataatactat tttaatcata gtattaaatt
1951  tctttaatta aaaatataaa taatttcaat ttaattctat accaaattaa
2001  cccgaaaata ttttatctaa catacacaaa gacacataaa agttttgata
2051  actgcctaaa aaaataagct tttgaattat taattagttg ttattcaatg
2101  ataaaataac attatttgtc aactagtgaa ttccaattac gcaaaatgat
2151  tcactttttt agtggaaaat atcaaagaaa aatgagaagt ttatatgaaa
2201  ataaactctt tcccactatg atgaatacat gtaagaaaac tttcatgaaa
2251  agaaaactta tttactcaat ataaaaatag aagactcttt atctttcacg
2301  agtaaaagtt cacgaaaacc atattttcct attgattaaa gaaatcatag
2351  aagttaaaat aatcaacaag ggcaagccaa aaacttctag tgtgggattt
2401  actaataga agtatatata ttacgatgtt tatgcgtacc tatttccct
2451  caatgagaag agaaattcca taatattggt gtcttaagtt tggacggaaa
```

FIG. 7C

```
2501  taaagagcag caaaaaagtt agggaaggaa acctttgttt tcttcaataa
2551  ttatagaaaa taatttcttt tattgattta gatattaaat aagcaaagat
2601  atgcatgctc attacgtgtc tataaataaa aacacgtttg tacatagcat
2651  ctactataaa cgttcctttt gcttccccga ttcttcgaaa cacttattga
2701  tatcttcaga cacaacaaat taattacaga gacagttaca gaggaaaaag
2751  atctatgacg gaaactggtg atgatcttgc tacggtgaag aagccaatcc
2801  catttctcgt tatcttcaaa gatttaaggt gtgtgtttat gtattcatga
2851  aatggtgatg aaattttga aagaagtgat gcataacatt agtttattta
2901  tgtaaaattg cagacatgta ttcagtaggg acacaactgg gcgagagatt
2951  ctaggcatcg cgtttccagc agctttggct ttagctgctg atccaatcgc
3001  ttctctgatt gataccgctt ttgtcgggcg tttaggagcg gttcagctag
3051  cggcggttgg agtttccatt gccatattca atcaagcttc tagaattacg
3101  atattcccac ttgtgagcct cacaacttca tttgtggcag aggaagacac
3151  gatggagaag atgaaagaag aagcaaacaa agccaatctt gttcatgcag
3201  aaactatact tgttcaagat tctttggaaa agggcatttc ttcacctaca
3251  agtaacgata ccaaccagcc acagcaacct ccaggtaaat tccgcatatc
3301  tcactcgaca ttgataactt ttattaaagt ttcgattgtt tttttactgt
3351  tggtttcttc tctcgatctc ttttgtttca atttgttgtt tttttggttg
3401  tattaaactt agctccggat acaaagtcaa atagcggaaa caaatcgaat
3451  aaaaaggaga agaggaccat tagaacagca tcaacagcta tgatcttggg
3501  gttaatcctt ggccttgtgc aagctatttt cttgattttc agttcaaagt
3551  tgcttctagg cgtcatggga gtgaaaccag taagttttca gaaatataca
3601  tattttgttg ggatctatag cataaaatgt tttgactaat ttgagttgaa
3651  tttggataac agaattcacc aatgttatca ccagcacaca agtacttgag
3701  catacgagct ttgggggctc ctgcattgct tctatctctt gctatgcaag
3751  gcatctttcg tggattcaag gacaccaaaa ctcctctctt gccactgat
3801  aattaagttg ttaacttaga tcatctttaa tgatcactct ccttacttct
```

FIG.7D

```
3851  tataatattt tgccttaatg cgtgaaacag tcgtagcaga tgttatcaac
3901  atagttctcg accccatctt cattttttgtg cttcgtctag ggatcatcgg
3951  tgcagccatt gcccatgtca tttctcagta agagaaatca ctaaaaaaat
4001  tccacacatg caaaagtgat cattattgaa caaaatcgct aggcgcactc
4051  ttgttttttct acagctataa atagacttgt gaagtcataa cctcaaacaa
4101  aaacaaatga tttgtttgtg tacgtgaagg tacttcatga ctctaatatt
4151  gttcgtcttc ctcgcaaaga aagttaattt gattccacca aacttcgggg
4201  atttgcagtt tggaaggttc cttaaaaatg gtacgtatgg atgcatattt
4251  attaaaagtt gtggttcttg caataatatt tttttttaaa aacaagatcc
4301  gtcgtaggag ctaatgcaca gagtccaaaa ataaattaac aaaaaattta
4351  tctatataat aatagaattc aatcaaataa ggtctatatt taaaatattg
4401  aatattttga aatatatagt taagaaaatg agaaatgtgg atatatgtct
4451  aacaagtata gtattaaaaa tgaaagggct actattgctg gcgaggacca
4501  tagcagtgac gttttgtcag accttagcag cagcaatggc ggcgcggctg
4551  ggtacaacac caatggctgc ttttcagatt tgtttacaag tatggttaac
4601  ttcttctctt ctcaatgatg gtcttgccgt tgctggtcag gtaatcatgt
4651  tttctcgttg tattaattta tgtatagttt atatggttga tcaagttgta
4701  tgtagaaaat gatcattcaa tacgttgcag gcgattctgg cttgttcgtt
4751  tgctgagaag gactataaca aagtgactgc tgttgcatcc cgtgttctac
4801  aggttcggtc caaaaatcac attaccaaac ctttctttaa aaataaaata
4851  attgtgtaac taaaacagaa atgaatttga tacgcagatg ggttttgtgt
4901  taggacttgg actgtccgtt tttgttggac taggtctcta ctttggtgcc
4951  ggagttttct ccaaggaccc tgctgttatt cacctcatgg ccatcggaat
5001  accggtaact aataatcaaa taataattac tatagtataa aaatcatttt
5051  aaaagaattt tactaatgag aagaggttat atatatttat gcagtttata
5101  gcagcaacgc agccaataaa ctctctcgcc tttgtattgg atggagtcaa
5151  ttttggagca tctgattttg cttacactgc atactccatg gtatgcacac
```

FIG. 7E

```
5201  tatatatact atgaaatgat taaaattcct ttttttttt  ttgaaatgac
5251  ttaaactttg tctatctttt tttcttgtaa tccaattatg ataaatcagg
5301  tgggagtggc ggccataagc attgcagcag taatatatat ggcaaagacc
5351  aatggtttca taggaatatg gatagctctt acaatctata tggctctccg
5401  ggctattact ggaattgcca ggtatttaaa ttgggccttt actatagccc
5451  actatagtag aagcagtatt tgactgagtg tttgaattta tgcaggatgg
5501  cgacaggaac tggaccgtgg aggttcttgc gtggacgatc atcctcttca
5551  tcttcctagg acttagttta tttataacga gttgcatctc ttcttccttc
5601  ttcgttttttg tttatggttc ttgtgtttgt ttttcaacat tttgttcgag
5651  agaccgttat catattatca gtttcacata aataatgcat attttaagt
5701  cattaaaata tggagccctc tgccctcact ggctttttc
```

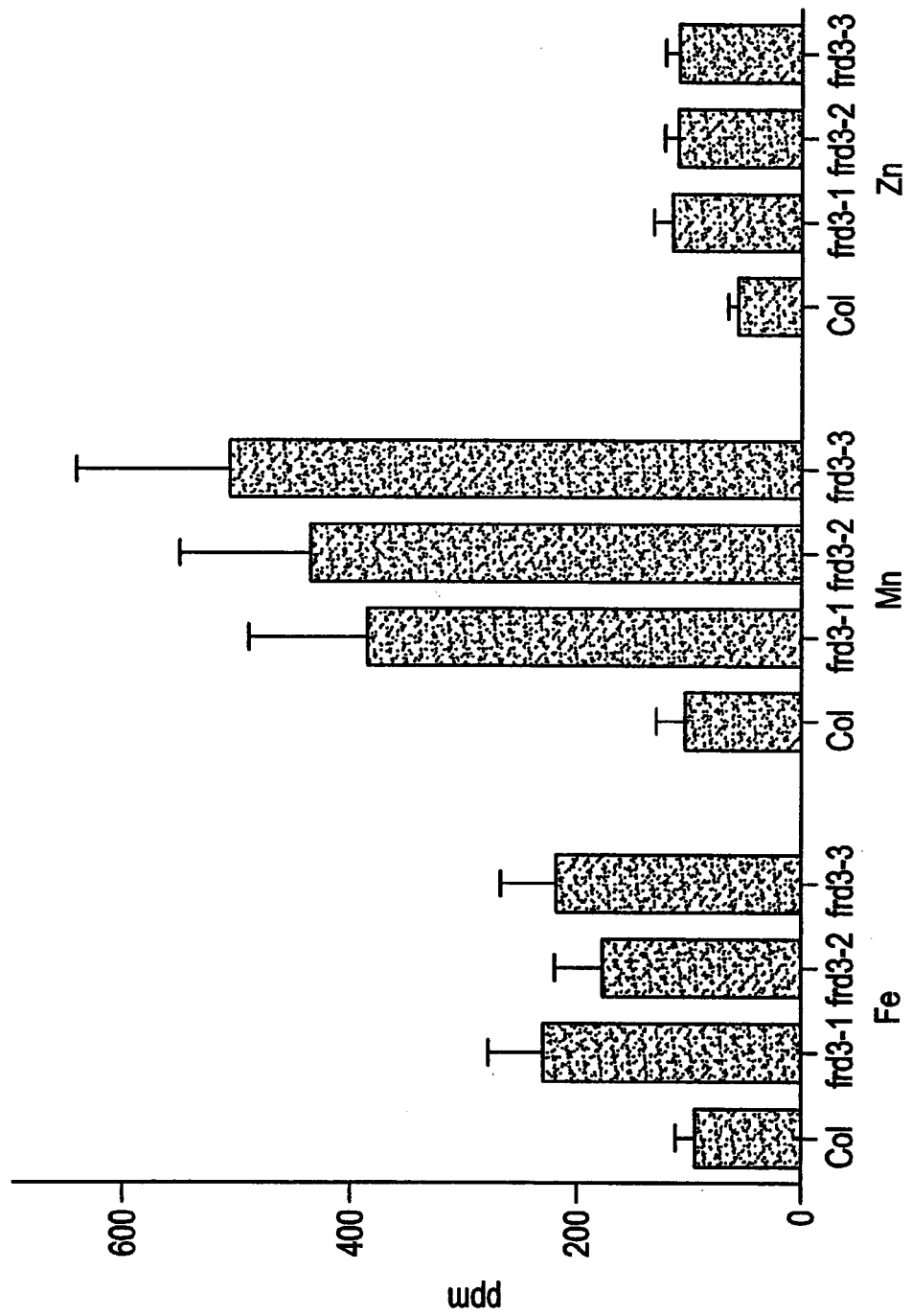

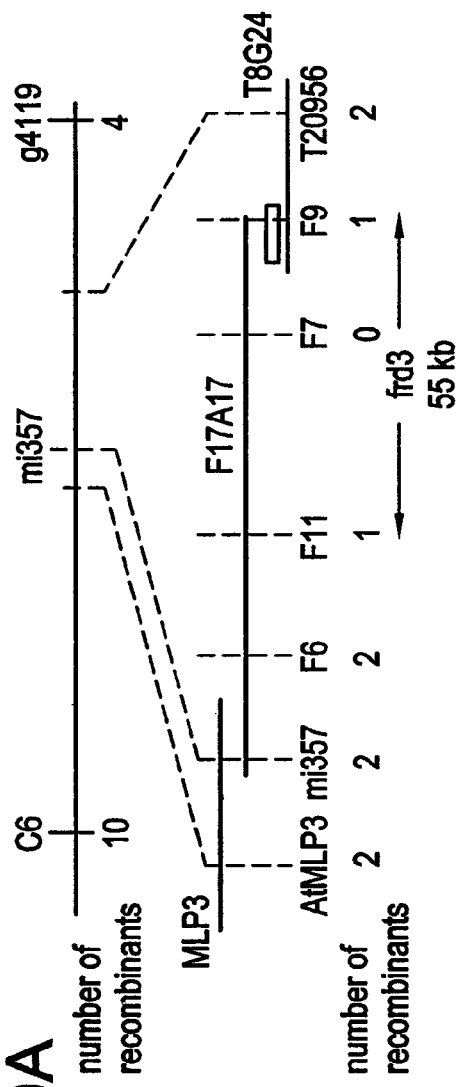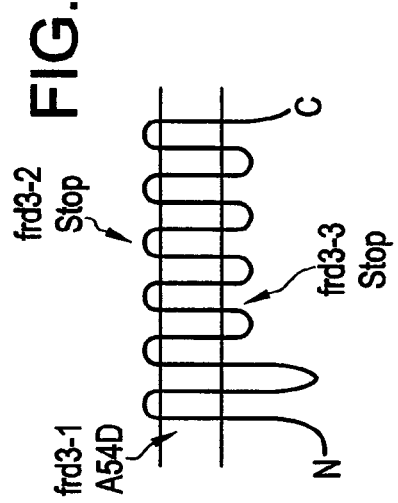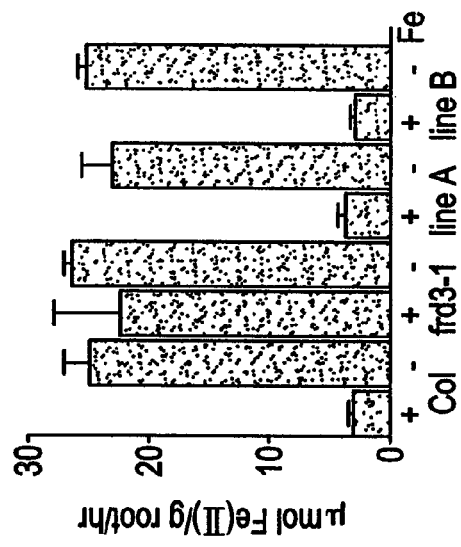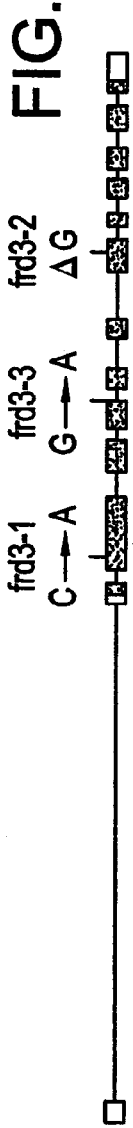
FIG. 10A
FIG. 10B
FIG. 10C
FIG. 10D

FIG. 13A

```
FRD3    1                                                       ----------MTETGDDLATVKKPIPFLVIFKDLRH----VFS
FRDL    1                                                       ----------MSEDGYNTDFPRN--PLYIFFSDFRS---VLK
EDS5    1                                                       ----------MLLCVSCLCNALVSVLAREVNGVHTG---VAR
ALF5    1                                                       ----------MADPATSSPLLDDHVGGEDERGRRSRSSTLVQ---KVI
TT12    1                                                       ----MSSTETYEPLLTRLHSDSQITERSSPEIEEFLRRGSTVTPRWLKL
ERC1    81  TLQQEAWQQGYDSHDRKRLLDEERDLLIDNKLLSQHGHGGGDIESHGHQAIGPDEEERPAEIANTWESAIESGQKISTT
NorM    1                                                       ----------------------------MHR
YdhE    1                                                       ----------------------------MQK
DinF    1                                                       ------MPPGVAVCFSSLFIRLVCMAF

FRD3    30   RDTTGREILGIAFLAELPAAALALAADPIASLIIDTAFVGRLGAVQLAAVGVSIAIFNQASRITFPLVSLTTSFVAEEDTMEKMK
FRDL    28   FDELGLEIARIALPAALALTADPIASLVDTAFIGQIGPVELAAVGVSIALFNQVSRIAFPLVSILNSFVAEEDACSSQQ
EDS5    30   PVDIKRELVMLSLPAIAGQAIDPLTLIMELAYICRLGSVELGSAGVSMAIFNTISKLFNIPLSVATSFVAEDIAKIAAQ
ALF5    36   DVEEAKAQMIYSLPMILTNVFYYCIPITSVMFASHLGQLELAGATLANSWATVSGFAFMVGLSGSLETLCGOGFGAKRYR
TT12    48   AVWESKLEWTESGASIVVSVLNYMLSEVTVMFIGHLCSLQIAGASIATVGLIQGLAYGIMLGMASAVQTVCGQAYGAROYS
ERC1    161  FKRETOVITMNALPLIFTFILONSLSLASIFSVSHLGTKELGGVTLGSMTANIIGLAAHQGLCTCLDTLCAQAYGAKNYH
NorM    4    YKEEASSEIKLATPVLIASVAQTGMGFVDIVMAGVTQTDMAAVSSHWLPSILFGIGLIEMALVPVVAQLNGSAREK
YdhE    4    YISEARLLALAIPVILAQIAIMAQTAMGFVDIVMAGYSATDMAAVAIGTSIWLPAILFGHGLIELALTPVIAQLNGSGRRER
DinF    22   LTSSDKALWHLEALPMIFSNITVPLLGVIGHLDSPVYLGGVAVGATATSFLFMLLFRMSIGLTAQAYGAKNPQ

FRD3    110  EEANKANLVHAETILVQDSLEKGISSPTSNDTNQPQQPPAPDTKSNSGNKSNKKEKRTIRTASTAMILGHLGLLVQAIFF
FRDL    108  DTVR--DHKECIEIGINNPTEETIELIPEKHKDSLSDEFKTSSSIFSISKPPAK-KRNIPSASSALIGGVLGLFQAVFF
EDS5    110  DLAS                                             EDSQSDIPSQGLPERKQLSSVSTALVLAIGIGIFEALAL
ALF5    116                                                   MLGVHLQSSCIVSLVFSILITIF
TT12    128                                                   SMGIICQRAMVLHLAAAVFLTFF
ERC1    241                                                   LVGVLVQRCAVTTIEAFLPMMYV
NorM    84                                                   IPFEIQQGVVLALISIPIIGV
YdhE    84                                                   LAHQVRQGFWLAGFVSVLIMLV
DinF    102                                                  ALARTLVQPLLIALGAGALIALLR
```

FIG. 13B

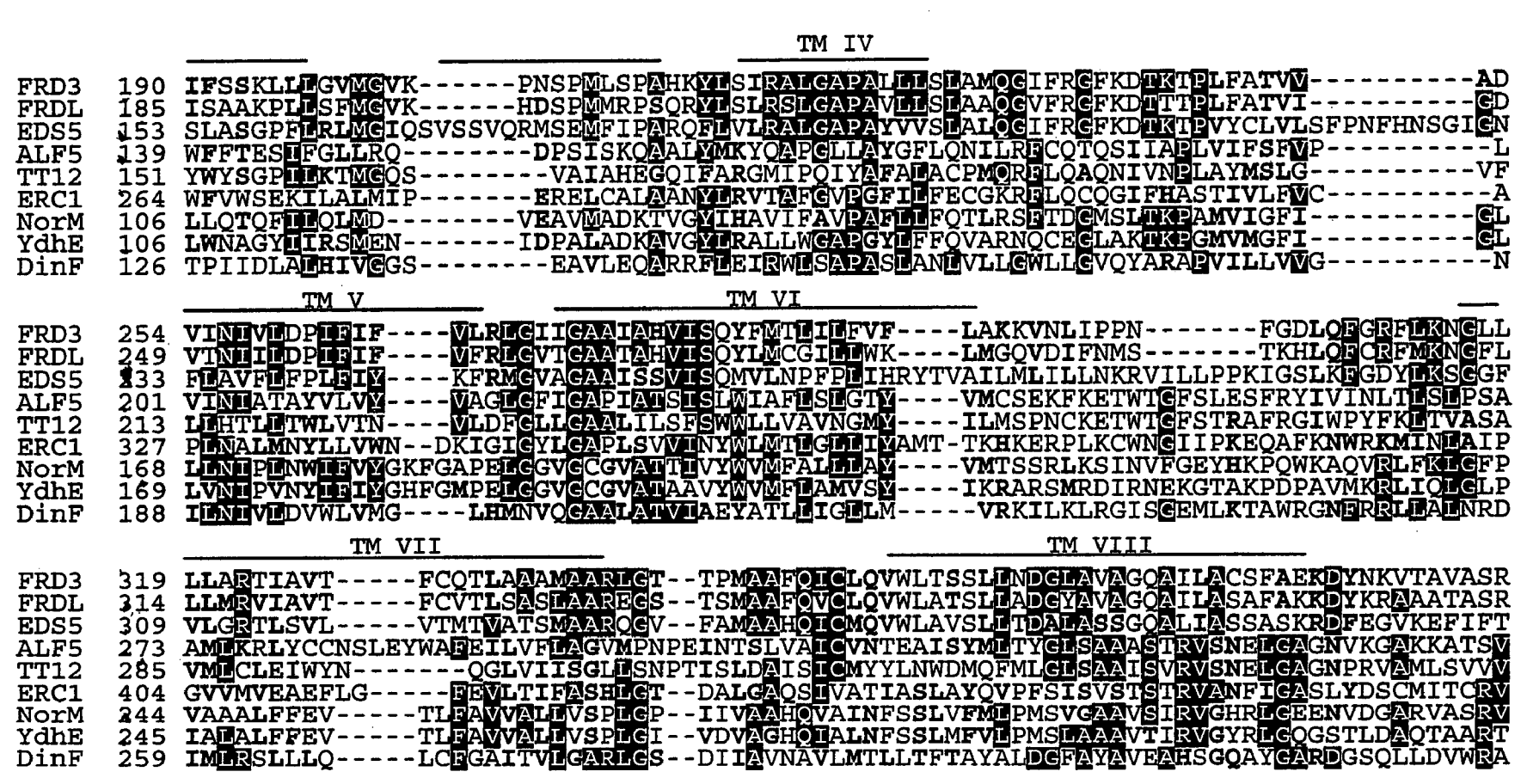

[Sequence alignment figure showing multiple protein sequences labeled FRD3, FRDL, EDS5, ALF5, TT12, ERC1, NorM, YdhE, and DinF, aligned across transmembrane regions TM IV, TM V, TM VI, TM VII, and TM VIII.]

FIG. 13C

```
                  TM IX                                    TM X                                 TM XI
FRD3  392 VLQMGFVLGLGLSVFVGLGLYFGAGVESKDPAVIHEMAIGIPEIAATQPINSLAFVLDGVNFGASDFA------YIAYSM
FRDL  387 VLQLGLVLGFVLAVILGAGLHFGARVETKDDKVLHLIISIGLPFVAGTQPINALAFVFDGVNFGASDFG------YAAASL
EDS5  382 FWGC-YLISCYIYIYRERCNVFGVVQIGVVTGIALAIVLGMSESSIADGGGRNIISVHAVCTGRVGAK--------WSV
ALF5  353 SVKLSLVLFALGVIVLLVGEHDGWVGLFSDSYIKEEFASRFELAASITLDSIQGVELSGVARGCGWQRLVTVINLATFYL
TT12  358 VNITTVLISSVLCVIVLVFRVGLSKAFILSDAEVIAAVSDLFPLLAVSIFLNGIQPIESGVAIGSGWQAVVAYVNLVTIYV
ERC1  477 SELLSFVCSSMNMFVICRYKEQIASLFSTESAVKMVDTLPLIAFMQLFDAFNASTAGCLRGQGRQKIGGYINLVAFYC
NorM  317 GIMVCLALATTITAIIIIVLSRELIAELYTNNPEVITAAMQLIEAAVYQCTDAVQVIAAGAIRGYKDMVRAIFNRTFIAVWI
YdhE  318 GEMVGVCMATLTAIFTVSLREQIALIHYNDNPEVITAAHEMLLAAVYQISDSIQVIGSGILRGYKDTRSIFYITFTAYWV
DinF  332 ACRQSGIVALIFSVVLLAGEHITALESLTQIQQADRYLIWQVILPVVGVWCYLEDCMFIGATRAT--------EMRN

FRD3  466 VGVAAISEAAVI-YMAKTNGFIGIWIALTFYMALRAITGIARMATGTGPWRFLRGRSSSSSS---------
FRDL  461 VMVAIVSILCLL-FLSSTHGFIGLWFGLTIYMSLRAAVGFWR---------------------------
EDS5  452 GGAEHVHGIADGGWIQQVKKELPVSIYK-----------------------------------------
ALF5  433 IGMPIAAFCGFK----LKFYAKGLWIGLICCIFCQSSELLMTIFRKWTKLNVATV---------------
TT12  438 IGLIPIGCVEFGFK----TSLGVAGIWWCMIACVILQTLTIIVLTLKTNWTSEVENAAQRVKTSATENQEMANAGV
ERC1  557 LGVPMAYYLAFL----YHLGVGGLWLGITSALVMMSVCQGYAVFHGDRRRILGAAARKRNAETHTS-------
NorM  397 LGIPTGVILGRTDWIVEPMGAQGFWLGLTAAALMLGVRLRWMHRQEPDVQLNFSLQ----------
YdhE  398 LGIPSGYIALIDLVVEPMGPAGEWIGFIIGLTSAAIMMLRMRFLQRLPSAIILQRASR-----------
DinF  404 SMAVAAGFALTLLTLPWLGNHALWMLALITVFLAALRGLSEAATWRRHWRNGTWFAAT----------
```

FIG.14A frd3 cDNA.seq  Length: 1868  March 29, 2001 12:57  Type: N Check: 5408

```
   1  AAATAATCCC CTCTAAACTC TCCTAGATAC TCACTCATCA CTACTCATCT
  51  CAAGTTCACG TGACTACTTA TATAAGCGTT GACTACATAA AGAGACAGTT
 101  ACAGAGGAAA AAGATCTATG acggaaactg gtgatgatct tgctacggtg
 151  aagaagccaa tcccatttct cgttatcttc aaagatttaa gacatgtatt
 201  cagtagggac acaactgggc gagagattct aggcatcgcg tttccagcag
 251  ctttggcttt agctgctgat ccaatcgctt ctctgattga taccgctttt
 301  gtcgggcgtt taggagcggt tcagctagcg gcggttggag tttccattgc
 351  catattcaat caagcttcta gaattacgat attcccactt gtgagcctca
 401  caacttcatt tgtggcagag aagacacga tggagaagat gaaagaagaa
 451  gcaaacaaag ccaatcttgt tcatgcagaa actatacttg ttcaagattc
 501  tttggaaaag ggcatttctt cacctacaag taacgatacc aaccagccac
 551  agcaacctcc agctccggat acaaagtcaa atagcggaaa caaatcgaat
 601  aaaaggaga agaggaccat tagaacagca tcaacagcta tgatcttggg
 651  gttaatcctt ggccttgtgc aagctatttt cttgattttc agttcaaagt
 701  tgcttctagg cgtcatggga gtgaaaccaa attcaccaat gttatcacca
 751  gcacacaagt acttgagcat acgagctttg gggctcctg cattgcttct
 801  atctcttgct atgcaaggca tctttcgtgg attcaaggac accaaaactc
 851  ctctctttgc cactgtcgta gcagatgtta tcaacatagt tctcgacccc
 901  atcttcattt tgtgcttcg tctagggatc atcggtgcag ccattgccca
 951  tgtcatttct cagtacttca tgactctaat attgttcgtc ttcctcgcaa
1001  agaaagttaa tttgattcca ccaaacttcg gggatttgca gtttggaagg
1051  ttccttaaaa atgggctact attgctggcg aggaccatag cagtgacgtt
1101  ttgtcagacc ttagcagcag caatggcggc gcggctgggt acaacaccaa
1151  tggctgcttt tcagatttgt ttacaagtat ggttaacttc ttctcttctc
1201  aatgatggtc ttgccgttgc tggtcaggcg attctggctt gttcgtttgc
1251  tgagaaggac ataacaaag tgactgctgt tgcatcccgt gttctacaga
```

FIG. 14B

```
1301  tgggttttgt gttaggactt ggactgtccg ttttttgttgg actaggtctc
1351  tactttggtg ccggagtttt ctccaaggac cctgctgtta ttcacctcat
1401  ggccatcgga ataccgttta tagcagcaac gcagccaata aactctctcg
1451  cctttgtatt ggatggagtc aattttggag catctgattt tgcttacact
1501  gcatactcca tggtgggagt ggcggccata agcattgcag cagtaatata
1551  tatggcaaag accaatggtt tcataggaat atggatagct cttacaatct
1601  atatggctct ccgggctatt actggaattg ccaggatggc gacaggaact
1651  ggaccgtgga ggttcttgcg tggacgatca tcctcttcat cttcctagGA
1701  CTTAGTTTAT TTATAACGAG TTGCATCTCT TCTTCCTTCT TCGTTTTTGT
1751  TTATGGTTCT TGTGTTTGTT TTTCAACATT TTGTTCGAGA GACCGTTATC
1801  ATATTATCAG TTTCACATAA ATAATGCATA TTTTTAAGTC ATTAAAATAA
1851  AAAAAAAAAA AAAAAAA
```

ISOLATED FERRIC REDUCTASE DEFECTIVE POLYPEPTIDES AND USES THEREOF

RELATED APPLICATIONS

The present application is a continuation of PCT patent application number PCT/US02/09962, filed on Mar. 27, 2002, which claims priority to U.S. provisional application Ser. No. 60/280,621, filed on Mar. 30, 2001 and entitled Novel Molecules of the Multi-Drug and Toxin Efflux (MATE) Protein Family and Uses Thereof, the entire contents of which is expressly incorporated herein by reference.

GOVERNMENT INTERESTS

Work described herein was supported in part by funding from the Life Sciences Research Foundation (LSRF) and the National Science Foundation (NSF), Contract No. IBN-9974837. The United States Government has certain rights in the invention.

BACKGROUND OF THE INVENTION

Iron deficiency is one of the most common human nutritional disorders in the world today (see the website at who.int/nut/ida.htm; Yip, R. (1994) *J. Nutr.* 124: 1479S–1490S). Indeed, iron is an essential nutrient for virtually all organisms because it plays a critical role in important biochemical processes such as respiration and photosynthesis. Although abundant in nature, iron is often available in limited amounts because the oxidized form, Fe(III), is extremely insoluble at neutral or basic pH. This fact is of particular importance to agriculture because approximately one-third of the world's soils are classified as iron-deficient (Yi, Y. et al. (1994) *Plant Physiol.* 104: 815–820). Many "iron-efficient" plant varieties have iron uptake strategies (designated strategy I or strategy II) that are directed at solubilizing iron (Römheld, V. (1987) *Physiol. Plant.* 70: 231–234). Strategy II plants, which include all of the grasses, release Fe(III) compounds called "phytosiderophores" into the surrounding soil that bind iron and are then taken up into the roots. Most other iron-efficient plants use strategy I and respond to iron deprivation by inducing the activity of membrane-bound Fe(III) chelate reductases that reduce Fe(III) to the more soluble Fe(II) form. The Fe(II) product is then taken up into the roots by an Fe(II) specific transport system that is also induced by iron-limiting growth conditions. Furthermore, the roots or strategy I plants release more protons when iron-deficient, lowering the rhizosphere pH and thereby increasing the solubility of Fe(III). Thus, it would be desirable to take advantage of this understanding of iron-uptake strategies to produce plants which have increased iron-uptake capabilities.

In addition, metal ion pollution is perhaps one of the most difficult environmental problems facing the industrial world today. Unlike the organic and even halogenated organic pollutants, which can be degraded in the soil, metals are essentially nonmutable. The electrolytic, in situ immobilization and chemical leaching technologies for cleaning polluted sites are all very expensive, particularly in light of how vast some of these sites are. With the exception of approaches like vitrification, most in situ metal ion remediation schemes require some mechanism for increased mobilization of the metal ion. This raises the possibility of further endangering local wildlife or adjacent ecosystems not already affected. Thus, a need still exists for better methods for removing toxic pollutants from the soil.

SUMMARY OF THE INVENTION

This invention is based, at least in part, on the discovery of the functional characteristics of the wild type ferric reductase defective (FRD3) nucleic acid and protein molecules and the discovery of novel mutant FRD3 molecules. Designated herein as "FRD3 nucleic acid and protein molecules," this novel group of molecules belongs to the multi-drug and toxin efflux (MATE) family, and includes, for example, FRD3 molecules such as FRD3, FRD3-1, FRD3-2, and FRD3-3 (FRD3-3 is also referred to herein as MAN1) molecules.

Wild type FRD3 nucleic acid and protein molecules, such as FRD3, are expressed in plants under metal deficient conditions, e.g., iron deficient conditions, and are capable of increasing metal uptake in plants under such conditions and decreasing metal uptake in plants under metal sufficient conditions. In contrast, mutant FRD3 nucleic acid and protein molecules, such as FRD3-1, FRD3-2, and FRD3-3, are expressed under both metal sufficient and metal deficient conditions which results in an increase of metal uptake in plants under both metal sufficient and deficient conditions. Accordingly, wild type FRD3 and mutant FRD3 nucleic acid and protein molecules are useful as modulating agents in regulating metal homeostasis, e.g., iron homeostasis.

The FRD3 nucleic acid and protein molecules share several structural/functional properties. Structurally, FRD3 polypeptides are expressed in the roots but not in shoots of plants and include, for example, at least one transmembrane domain belonging to the MATE family of molecules (Brown et al., Mol. Micro., 31:393, 1999), preferably approximately ten to twelve transmembrane domains. Functionally, FRD3 nucleic acid and protein molecules are capable of, for example, expressing metal deficiency responses, e.g., iron deficiency responses. In particular, wild type FRD3 molecules are capable of increasing metal uptake in plants under metal deficient conditions and decreasing metal uptake in plants under metal sufficient conditions. Mutant FRD3 molecules, e.g., FRD3-1, FRD3-2, and FRD3-3, are capable of expressing metal deficiency responses under both metal deficient and metal sufficient conditions. Mutant FRD3 molecules are also capable of, (1) misexpressing ferric chelate reductase activity, (2) overaccumulating metals, e.g., iron, or (3) causing chlorosis. In particular, while not intending to be limited to any theory, it is believed that the FRD3 nucleic acid and protein molecules serve as a receptor for metal deficiency signals, for example, a receptor for iron deficiency signals. Accordingly, in one aspect, this invention provides isolated nucleic acid molecules encoding FRD3 proteins or biologically active portions thereof, as well as nucleic acid fragments suitable as primers or hybridization probes for the detection of frd3-encoding nucleic acids.

In one embodiment, a frd3 nucleic acid molecule of the invention is at least 50%, 55%, 60%, 65%, 70%, 75%, 80%, 85%, 89%, 90%, 95%, 96%, 97%, 98%, 99% or more identical to the nucleotide sequence (e.g., to the entire length of the nucleotide sequence) shown in SEQ ID NO:1, 2, 4, 5, 7, 8, 20, or a complement thereof.

In a preferred embodiment, the isolated nucleic acid molecule includes the nucleotide sequence shown in SEQ ID NO:1, 2, 4, 5, 7, 8, 20, or a complement thereof. In another embodiment, the nucleic acid molecule includes the coding region of SEQ ID NO:2 (nucleotides 118–1698), the coding region of SEQ ID NO:5 (nucleotides 118–1182), the coding region of SEQ ID NO:8 (nucleotides 118–870), or the coding region of SEQ ID NO:20 (nucleotides 118–1698). In yet a further embodiment, the nucleic acid molecule includes the coding region of SEQ ID NO:2 and nucleotides 1–117 or 1699–1868 of SEQ ID NO:1, the coding region of SEQ ID NO:5 and nucleotides 1–117 or 1183–1867 of SEQ ID NO:5, the coding region of SEQ ID NO:8 and nucleotides 1–117 or 871–1950 of SEQ ID NO:1, or the coding region of SEQ ID NO:20 and nucleotides 1–117 or 1699–1950 of SEQ ID NO:20. In another preferred embodiment, the nucleic acid molecule consists of the nucleotide sequence shown in SEQ ID NO:1, 2, 4, 5, 7, 8, 20, or the coding region thereof.

In another embodiment, a frd3 nucleic acid molecule includes a nucleotide sequence encoding a protein having an amino acid sequence sufficiently identical to the amino acid sequence of SEQ ID NO:3, 6, 9, or 10. In a preferred embodiment, a frd3 nucleic acid molecule includes a nucleotide sequence encoding a protein having an amino acid sequence at least 50%, 55%, 60%, 65%, 70%, 75%, 80%, 85%, 89%, 90%, 95%, 96%, 97%, 98%, 99% or more identical to the entire length of the amino acid sequence of SEQ ID NO: 3, 6, 9, or 10.

In another preferred embodiment, an isolated nucleic acid molecule encodes the amino acid sequence of a FRD3 polypeptide (e.g., an *A. thaliana* FRD3-1 polypeptide, an *A. thaliana* FRD3-2 polypeptide, or an *A. thaliana* FRD3-3 polypeptide). In yet another preferred embodiment, the nucleic acid molecule includes a nucleotide sequence encoding a protein having the amino acid sequence of SEQ ID NO:3, 6, 9, or 10. In yet another preferred embodiment, the nucleic acid molecule is at least 50, 100, 150, 200, 250, 300, 350, 400, 450, 500, 550, 600, 650, 653, 700, 750, 800, 850, 900, 950, 1000, 1100, 1200, 1300, 1400, 1500, 1600, 1700 or more nucleotides in length. In a further preferred embodiment, the nucleic acid molecule is at least 50, 100, 150, 200, 250, 300, 350, 400, 450, 500, 550, 600, 650, 653, 700, 750, 800, 850, 900, 950, 1000, 1100, 1200, 1300, 1400, 1500, 1600, 1700 or more nucleotides in length and encodes a protein having a FRD3 activity (as described herein).

Another embodiment of the invention features nucleic acid molecules, preferably frd3 nucleic acid molecules, which specifically detect frd3 nucleic acid molecules relative to nucleic acid molecules encoding non-FRD3 proteins. For example, in one embodiment, such a nucleic acid molecule is at least 20, 30, 40, 50, 100, 150, 200, 250, 300, 350, 400, 450, 500, 550, 600, 650, 653, 700, 750, 800, 850, 900, 950, 1000, 1100, 1200, 1300, 1400, 1500, 1600, 1700 or more nucleotides in length and hybridizes under stringent conditions to a nucleic acid molecule comprising the nucleotide sequence shown in SEQ ID NO:1, 2, 4, 5, 7, 8, 20, or a complement thereof.

In preferred embodiments, the nucleic acid molecules are at least 15 nucleotides (e.g., 15 contiguous nucleotides) in length and hybridize under stringent conditions to the nucleotide molecules set forth in SEQ ID NO: 1, 2, 4, 5, 7, 8, 20, or a complement thereof. In certain embodiments, the nucleic acid molecules are at least 15 nucleotides in length and hybridize under stringent conditions to nucleotides 1–117 and 1699–1868 of SEQ ID NO:2, nucleotides 1–117 and 1183–1867 of SEQ ID NO:5, nucleotides 1–117 and 871–1950 of SEQ ID NO:8, or nucleotides 1–117 and 1699–1868 of SEQ ID NO:20. In another embodiment, the nucleic acid molecules comprise nucleotides 1–117 and 1699–1868 of SEQ ID NO:2, nucleotides 1–117 and 1183–1867 of SEQ ID NO:5, nucleotides 1–117 and 871–1950 of SEQ ID NO:8, or nucleotides 1–117 and 1699–1868 of SEQ ID NO:20.

In other preferred embodiments, the nucleic acid molecule encodes a naturally occurring allelic variant of a polypeptide comprising the amino acid sequence of SEQ ID NO:3, 6, 9, or 10, wherein the nucleic acid molecule hybridizes to a nucleic acid molecule comprising SEQ ID NO:1, 2, 4, 5, 7, 8, 20, or a complement thereof, under stringent conditions.

Another embodiment of the invention provides an isolated nucleic acid molecule which is antisense to a frd3 nucleic acid molecule, e.g., the coding strand of a frd3 nucleic acid molecule. Double stranded RNA comprising frd3-specific sequences in the sense and antisense orientations and capable of duplex formation with frd3 genes is also within the scope of the present invention.

Another aspect of the invention provides a vector comprising a frd3 nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a FRD3 protein, by culturing in a suitable medium, a host cell, e.g., a mammalian host cell such as a non-human mammalian cell, of the invention containing a recombinant expression vector, such that the protein is produced.

Another aspect of this invention features isolated, e.g., isolated from the *Arabidopsis* family of plants, recombinant, or synthetic FRD3 proteins and polypeptides (e.g., FRD3-1, FRD3-2, and FRD3-3). In one embodiment, an isolated FRD3 protein includes at least one transmembrane domain belonging to the MATE family of molecules, preferably approximately ten to twelve transmembrane domains.

In a preferred embodiment, a FRD3 protein includes at least one transmembrane domain belonging to the MATE family of molecules and has an amino acid sequence at least about 50%, 55%, 60%, 65%, 67%, 68%, 70%, 72%, 75%, 80%, 85%, 87%, 90%, 95%, 96%, 97%, 98%, 99% or more identical to the amino acid sequence of SEQ ID NO:3, 6, 9, or 10.

In another preferred embodiment, a FRD3 protein includes at least one transmembrane domain belonging to the MATE family of molecules and has a FRD3 activity (as described herein).

In yet another preferred embodiment, a FRD3 protein includes at least one transmembrane domain belonging to the MATE family of molecules and is encoded by a nucleic acid molecule having a nucleotide sequence which hybridizes under stringent hybridization conditions to a nucleic acid molecule comprising the nucleotide sequence of SEQ ID NO:1, 2, 4, 5, 7, 8, 20, or a complement thereof.

In another embodiment, the invention features fragments of the protein having the amino acid sequence of SEQ ID NO:3, 6, 9, or 10, wherein the fragment comprises at least 15 amino acids (e.g., contiguous amino acids) of the amino acid sequence of SEQ ID NO:3, 6, 9, or 10. In another embodiment, a FRD3 protein has the amino acid sequence of SEQ ID NO:3, 6, 9, or 10.

In another embodiment, the invention features a FRD3 protein which is encoded by a nucleic acid molecule consisting of a nucleotide sequence at least about 50%, 55%, 60%, 65%, 70%, 75%, 80%, 85%, 90%, 95%, 96%, 97%, 98%, 99% or more identical to a nucleotide sequence of SEQ ID NO:1, 2, 4, 5, 7, 8, 20, or a complement thereof. This invention further features a FRD3 protein which is encoded by a nucleic acid molecule consisting of a nucleotide sequence which hybridizes under stringent hybridization conditions to a nucleic acid molecule comprising the nucleotide sequence of SEQ ID NO:1, 2, 4, 5, 7, 8, 20, or a complement thereof.

The proteins of the present invention or portions thereof, e.g., biologically active portions thereof, can be modified to alter FRD3 bioactivity, e.g., to impart desired characteristics thereon, such as increased solubility, enhanced therapeutic or prophylactic efficacy, or stability. Such modified peptides are considered functional equivalents of peptides having an activity of FRD3 as defined herein. A modified peptide can be produced in which the amino acid sequence has been altered, such as by amino acid substitution, deletion, or addition. In another embodiment, a component which imparts a desired characteristic on a peptide can be linked to the peptide to form a modified peptide.

The proteins of the present invention or portions thereof, e.g., biologically active portions thereof, can be operatively linked to a non-FRD3 polypeptide (e.g., heterologous amino acid sequences) to form fusion proteins. The invention further features antibodies, such as monoclonal or polyclonal antibodies, that specifically bind proteins of the invention, preferably FRD3 proteins. In addition, the FRD3 proteins or biologically active portions thereof can be incorporated into pharmaceutical compositions, which optionally include pharmaceutically acceptable carriers.

In another aspect, the present invention provides a method for detecting the presence of a FRD3 nucleic acid molecule, protein, or polypeptide in a biological sample by contacting the biological sample with an agent capable of detecting a FRD3 nucleic acid molecule, protein, or polypeptide such that the presence of a FRD3 nucleic acid molecule, protein or polypeptide is detected in the biological sample.

In another aspect, the present invention provides a method for detecting the presence of FRD3 activity in a biological sample by contacting the biological sample with an agent capable of detecting an indicator of FRD3 activity such that the presence of FRD3 activity is detected in the biological sample.

In another aspect, the invention provides a method for modulating FRD3 activity comprising contacting a cell capable of expressing FRD3 with an agent that modulates FRD3 activity such that FRD3 activity in the cell is modulated. In one embodiment, the agent inhibits FRD3 activity. In another embodiment, the agent stimulates FRD3 activity. In one embodiment, the agent is an antibody that specifically binds to a FRD3 protein. In another embodiment, the agent modulates expression of FRD3 by modulating transcription of a frd3 gene or translation of a frd3 mRNA. In yet another embodiment, the agent is a nucleic acid molecule having a nucleotide sequence that is antisense to the coding strand of a frd3 mRNA or a frd3 gene. In yet another embodiment, the agent is a double stranded RNA molecule.

The invention also provides transgenic plants in which the expression of an FRD3 polypeptide is altered, as well as seeds and cells derived from such plants. For example, the invention includes a method for evaluating the effect of the expression or misexpression of a frd3 gene on a parameter related to iron homeostasis. The method includes providing a transgenic plant having a frd3 transgene, or which otherwise misexpresses a frd3 gene, contacting the transgenic plant with an agent, and evaluating the effect of the transgene or misexpression of the frd3 gene on the parameter related to iron homeostasis (e.g., by comparing the value of the parameter for a transgenic plant with the value for a control).

In addition, the transgenic plant, e.g., maize, wheat, rye, sorghum, cassava, beans, rice, beans, and peas, in which expression of a FRD3 polypeptide is altered can be incorporated into a pharmaceutical composition which includes the transgenic plant, or a portion thereof, and a pharmaceutically acceptable carrier. Such compositions can be used as human or animal nutritional supplements to provide, for example, iron to a subject with iron-deficiency or zinc to a subject with zinc-deficiency.

In another aspect the invention provides methods for identifying a compound that binds to or modulates the activity of a FRD3 protein, by providing an indicator composition comprising a FRD3 protein having FRD3 activity, contacting the indicator composition with a test compound, and determining the effect of the test compound on FRD3 activity in the indicator composition to identify a compound that modulates the activity of a FRD3 protein.

Methods for identifying an agent which inhibits or activates/stimulates a FRD3 polypeptide are also within the scope of the invention. These methods include contacting a first polypeptide comprising a naturally occurring ligand of FRD3, with a second polypeptide comprising a FRD3 polypeptide and an agent to be tested and then determining binding of the second polypeptide to the first polypeptide. Inhibition of binding of the first polypeptide to the second polypeptide indicates that the agent is an inhibitor of a FRD3 polypeptide while activation/stimulation of binding of the first polypeptide to the second polypeptide indicates that the agent is an activator/stimulator or a FRD3 polypeptide.

In another aspect, the invention features a method for evaluating a candidate compound for the ability to interact with a FRD3 polypeptide. This method includes contacting the compound with the FRD3 polypeptide and evaluating the ability of the compound to interact with the FRD3 polypeptide. This method can be performed in vitro or in vivo.

The FRD3 polypeptides of the invention can be used to modulate metal concentrations in vitro or in vivo. In one aspect, the invention provides a method for modulating metal concentration in a biological sample containing the metal. This method includes providing a transgenic plant in which expression of a FRD3 polypeptide is altered and contacting the transgenic plant with the biological sample such that the metal concentration in the biological sample is modulated.

The invention further provides methods for removing a pollutant from soil. These methods include contacting a transgenic plant in which expression of an FRD3 polypeptide is altered with the soil such that the pollutant is removed from the soil. In a preferred embodiment, the pollutant is a metal, e.g., a metal selected from the group consisting of Pb, As, Co, Cu, Zn, Cd and/or Hg.

Additional methods of the invention include methods for treating a disorder associated with metal-deficiency, e.g., iron-deficiency or zinc-deficiency, in a subject. These methods include administering to a subject a therapeutically effective amount of a composition comprising a transgenic plant, or a portion thereof, in which expression of a FRD3 polypeptide is altered. In a preferred embodiment, the composition is administered in combination with a pharmaceutically acceptable carrier. In other preferred embodiments, the FRD3 polypeptide in the transgenic plant is overexpressed. In yet other preferred embodiments, the disorder associated with iron-deficiency is anemia.

Still additional methods of the invention include methods for promoting plant growth and/or survival. These methods include introducing into a plant a nucleic acid encoding a FRD3 polypeptide.

Other features and advantages of the invention will be apparent from the following detailed description and claims.

BRIEF DESCRIPTION OF THE FIGURES

FIGS. 1a–1b depicts the cDNA sequence of frd3-1 (SEQ ID NO:2).

FIGS. 2a–2b depicts the cDNA sequence of frd3-2 (SEQ ID NO:5).

FIGS. 3a–3b depicts the cDNA sequence of frd3-3 (SEQ ID NO:8).

FIG. 4 depicts the amino acid sequences of wild type FRD3 (SEQ ID NO:10) with transmembrane domains shown in bold, FRD3-1 (SEQ ID NO:3), FRD3-2 (SEQ ID NO:6), and FRD3-3 (SEQ ID NO:9).

FIGS. 5a–5e depicts the genomic sequence of frd3-1 (SEQ ID NO:1).

FIGS. 6a–6e depicts the genomic sequence of frd3-2 (SEQ ID NO:4).

FIGS. 7a–7e depicts the genomic sequence of frd3-3 (also referred to herein as man1) (SEQ ID NO:7).

FIG. 9 is a bar graph showing frd3 alleles accumulate more Fe, Mn and Zn in their shoots. Pooled samples of two week old shoots from plants grown on B5 plates were subjected to elemental analysis. This experiment was repeated and similar results obtained.

FIG. 10 shows the positional cloning and structure of the wild type frd3 gene.

(A) The region of Chromosome 3 containing frd3. The chromosome is depicted by the uppermost horizontal line with the flanking markers C6 and g4119. Below that are three BACs from the AGI minimal tiling path: MLP3, F17A17, and T8G24. Markers (see Materials and Methods), the number of recombinant chromosomes out of the 1640 examined, and the final 55 kb interval containing frd3 are shown below. The striped bar indicates the segment of genomic DNA used to complement frd3-1.

(B) Complementation of frd3-1. An 11 kb segment of genomic DNA, when expressed in frd3-1, restores the repression of Fe(III) chelate reductase activity in plants grown for three days in the presence of Fe(III) EDTA. Values are the mean of nine individual plants and error bars depict standard error.

(C) Predicted topology of the FRD3 protein. The 12 transmembrane domains, as predicted by HMMTOP, and the location and nature of the mutations carried by the three mutant alleles are shown.

(D) Intron/exon structure of frd3. The narrow lines depict intron sequences and broader lines, exon sequences. The broad, filled line corresponds to the open reading frame and the broad open line to the 5' and 3' untranslated regions. Line lengths are approximately to scale.

Figure 11:
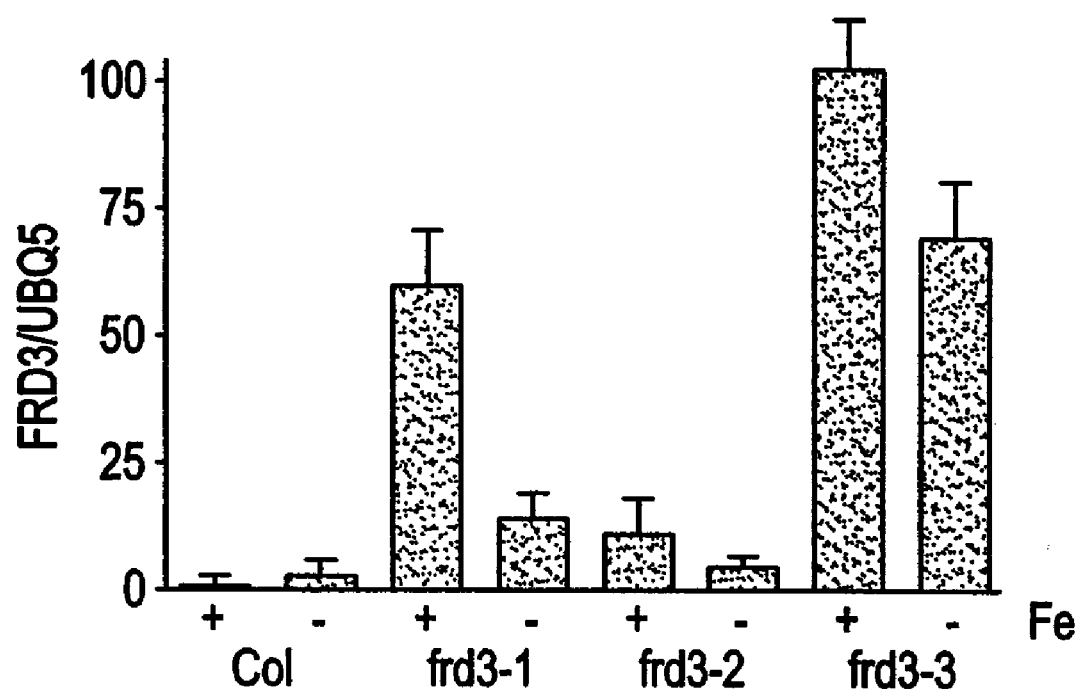

FIG. 11 is a bar graph showing wild type frd3 expression levels depend on iron status and genotype. The RNA blot used in FIG. 9 was re-probed with frd3. The expression level of frd3 was normalized to UBQ5 and is shown in arbitrary units. Results are presented as a graph to emphasize the very large differences in expression levels. Values are the mean of three replicate experiments and error bars indicate standard error.

Figure 12:
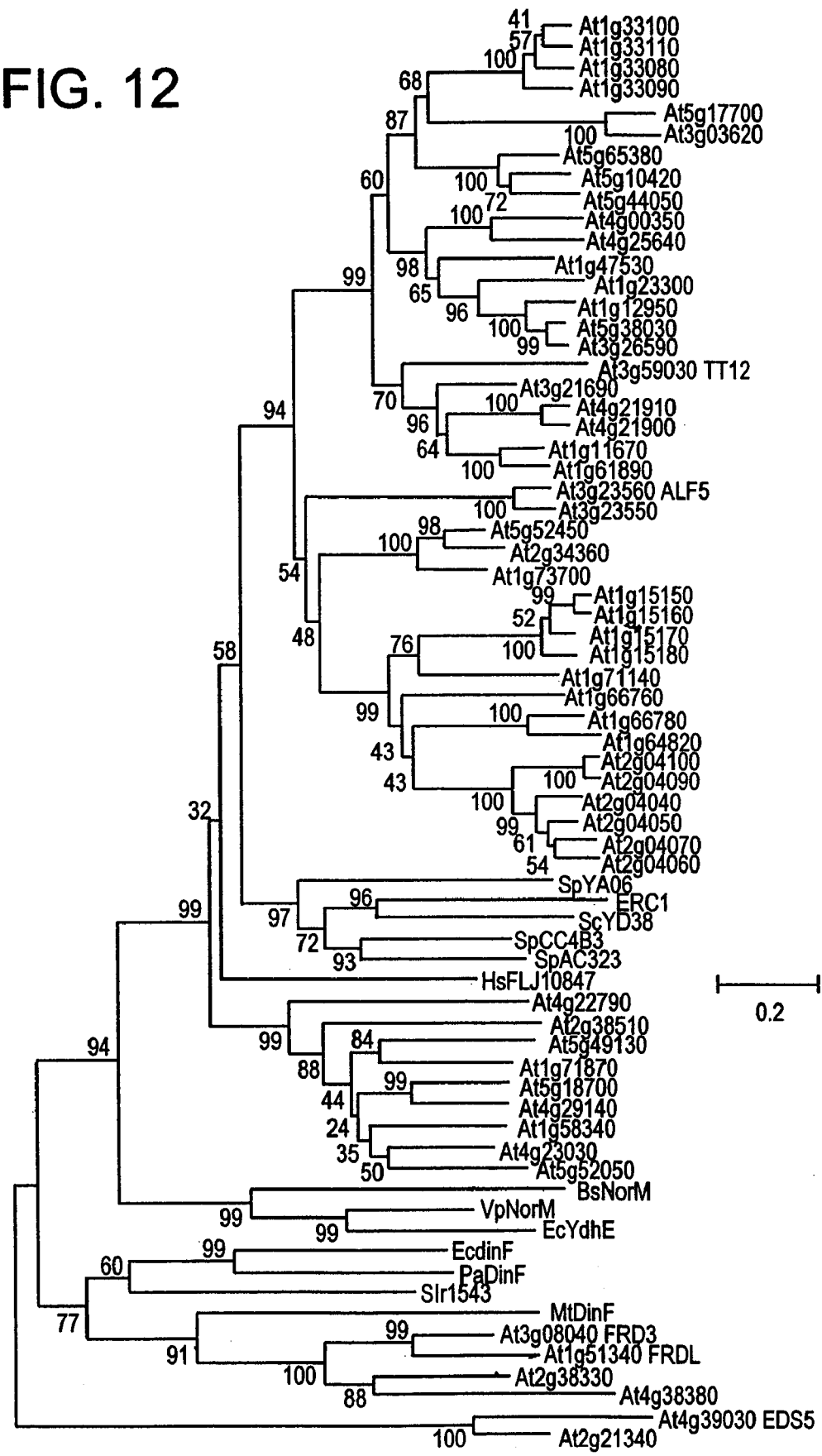

FIG. 12 is a dendogram showing amino acid sequence similarity relationships among selected MATE family members. Multiple sequence alignments were performed using the BCM Search Launcher and the dendogram using MEGA 2.1. Bootstrap values are shown next to each junction.

FIG. 13 is an alignment of the amino acid sequences of selected MATE family members. FRD3 (SEQ ID NO:3), FRDL (SEQ ID NO: 12), EDS5 (SEQ ID NO: 13), ALF5 (SEQ ID NO: 14), TT12 (SEQ ID NO: 15), ERC1 (SEQ ID NO: 16), NorM (SEQ ID NO: 17), YdhE (SEQ ID NO: 18) and DinF (SEQ ID NO: 19). Identical residues are on a black background and conservative substitutions on gray. Lines depict FRD3 transmembrane domains as predicted by HMMTOP. Multiple sequence alignments were performed using the BCM Search Launcher and residue shading using BoxShade 3.21.

FIGS. 14a–14b depicts the cDNA sequence of frd3 (SEQ ID NO:20).

DETAILED DESCRIPTION OF THE INVENTION

This invention is based, at least in part, on the discovery of the functional characteristics of the wild type ferric reductase defective (FRD3) nucleic acid and protein molecules and the discovery of mutant FRD3 molecules. Designated herein as "FRD3 nucleic acid and protein molecules," this novel group of molecules belongs to the multi-drug and toxin efflux (MATE) family, and includes, for example, FRD3 molecules such as FRD3, FRD3-1, FRD3-2, and FRD3-3 (FRD3-3 is also referred to herein as MAN1) molecules.

Wild type FRD3 nucleic acid and protein molecules, such as FRD3, are expressed in plants under metal deficient conditions, e.g., iron deficient conditions, and are capable of increasing metal uptake in plants under such conditions and decreasing metal uptake in plants under metal sufficient conditions. In contrast, mutant FRD3 nucleic acid and protein molecules, such as FRD3-1, FRD3-2, and FRD3-3, are expressed under both metal sufficient and metal deficient conditions which results in an increase of metal uptake in plants under both metal sufficient and deficient conditions. Accordingly, wild type FRD3 and mutant FRD3 nucleic acid and protein molecules are useful as modulating agents in regulating metal homeostasis, e.g., iron homeostasis.

The frd3 gene was identified in the plant *Arabidopsis thaliana*. *Arabidopsis thaliana*, a common wall cress, is a small member of the mustard or crucifer family. frd3 encodes an integral membrane protein 526 amino acid residues long which contains approximately ten to twelve transmembrane domains and may act as a regulatory factor involved in sensing and/or responding to iron levels frd3. The mutant alleles of the frd3 gene, i.e., additional members of the FRD3 family, designated herein as frd3-1, frd3-2, and frd3-3, possess single base pair alterations in a single open reading frame compared to the wild type frd3 gene.

The FRD3 nucleic acid and protein molecules share several structural/functional properties. Structurally, FRD3 polypeptides are expressed in the roots but not in shoots of plants and include, for example, at least one transmembrane domain belonging to the MATE family of molecules (Brown et al., Mol. Micro., 31:393, 1999), preferably approximately ten to twelve transmembrane domains. Functionally, FRD3 nucleic acid and protein molecules are capable of, for example, expressing metal deficiency responses, e.g., iron deficiency responses. In particular, wild type FRD3 molecules are capable of increasing metal uptake in plants under metal deficient conditions and decreasing metal uptake in plants under metal sufficient conditions. Mutant FRD3 molecules, e.g., FRD3-1, FRD3-2, and FRD3-3, are capable of expressing metal deficiency responses under both metal deficient and metal sufficient conditions. Mutant FRD3 molecules are also capable of, (1) misexpressing ferric chelate reductase activity, (2) overaccumulating metals, e.g., iron, or (3) causing chlorosis. In particular, while not intending to be limited to any theory, it is believed that the FRD3 nucleic acid and protein molecules serve as a receptor for metal deficiency signals, for example, a receptor for iron deficiency signals. Accordingly, in one aspect, this invention provides isolated nucleic acid molecules encoding FRD3 proteins or biologically active portions thereof, as well as nucleic acid fragments suitable as primers or hybridization probes for the detection of frd3-encoding nucleic acids.

As used herein, the term "multi-drug and toxin efflux" or "MATE" includes a molecule which is involved in a variety of processes by functioning as a transporter of small organic molecules. As a subset of the MATE family of molecules, the terms "ferric reductase defective," "FRD3," or "mutant FRD3" include molecules which serves as a receptor for metal deficiency signals, for example, a receptor for iron deficiency signals. Accordingly, FRD3 nucleic acid and protein molecules are capable of modulating metal concentrations. Bioactivity associated with FRD3 molecules, or "FRD3 activity," includes, for example, the expression of metal deficiency responses, e.g., iron deficiency responses. Mutant FRD3 molecules are also capable of (1) misexpressing ferric chelate reductase activity, (2) overaccumulating metals, e.g., iron, or (3) causing chlorosis. As modulators of metal concentrations, FRD3 molecules of the present invention provide novel diagnostic targets and therapeutic agents to control a variety of disorders relating to metal deficiency, e.g., iron deficiency or anemia. FRD3 molecules of the present invention also provide novel tools for promoting plant growth and/or survival and for removing pollutants from soil.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., monkey proteins. Members of a family may also have common functional characteristics.

For example, the family of FRD3 proteins comprises at least one transmembrane domain belonging to the MATE family of molecules in the protein or corresponding nucleic acid molecule. In a preferred embodiment, FRD3 molecules comprise at least about 3, 6, 9, 10, 11, 12, or more transmembrane domains belonging to the MATE family of molecules.

As used herein, the term "transmembrane domain" includes an amino acid sequence of about 15 amino acid residues in length which spans the plasma membrane. More preferably, a transmembrane domain includes about at least 5, 10, 12, 15, 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al., (1996) *Annual Rev. Neurosci.* 19: 235–263, the contents of which are incorporated herein by reference. As shown in FIG. 4, transmembrane domains of FRD3 correspond to the transmembrane domains found in the wild type FRD3 polypeptide which include, for example, amino acid residues 37–57, 61–80, 173–197, 215–237, 245–267, 272–294, 316–339, 355–379, 395–419, 423–447, 452–476, and 485–504 of SEQ ID NO: 10. Accordingly, FRD3 proteins having at least 50–60% homology, preferably about 60–70%, more preferably about 70–80%, or about 80–90% homology with a transmembrane domain of FRD3 are within the scope of the invention.

Isolated proteins of the present invention, preferably FRD3 proteins, have an amino acid sequence sufficiently identical to the amino acid sequence of SEQ ID NO:3, 6, 9, or 10, or are encoded by a nucleotide sequence sufficiently identical to SEQ ID NO:1, 2, 4, 5, 7, 8, or 20. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, a "FRD3 activity", "biological activity of FRD3" or "FRD3-mediated activity," includes an activity exerted by a FRD3 protein, polypeptide or nucleic acid molecule on a FRD3 responsive cell or tissue, or on a FRD3 protein substrate, as determined in vivo, or in vitro, according to standard techniques. In one embodiment, a FRD3 activity is a direct activity, such as an association with a FRD3 target molecule. As used herein, a "target molecule" or "binding partner" is a molecule with which a FRD3 protein binds or interacts in nature, such that FRD3 mediated function is achieved. A FRD3 target molecule can be a non-FRD3 molecule or a FRD3 protein or polypeptide of the present invention. In an exemplary embodiment, a FRD3 target molecule is a FRD3 substrate (e.g., a peptide). Alternatively, a FRD3 activity is an indirect activity, such as a cellular signaling activity mediated by interaction of the FRD3 protein with a FRD3 ligand or substrate. The biological activities of FRD3 are described herein. For example, the FRD3 proteins of the present invention can have one or more of the following activities: (1) the expression of metal deficiency, e.g., iron deficiency, responses under conditions of metal sufficiency or metal deficiency, (2) the misexpression of ferric chelate reductase activity, (3) the overaccumulation of metals, e.g., iron, or (4) chlorosis.

Accordingly, another embodiment of the invention features isolated FRD3 proteins and polypeptides having a FRD3 activity. Other preferred proteins are FRD3 proteins having at least one transmembrane domain and, preferably, a FRD3 activity.

Additional preferred proteins have at least one transmembrane domain and are, preferably, encoded by a nucleic acid molecule having a nucleotide sequence which hybridizes under stringent hybridization conditions to a nucleic acid molecule comprising the nucleotide sequence of SEQ ID NO:1, 3, 4, 6, 8, 9, or a complement thereof.

Various aspects of the invention are described in further detail in the following subsections:

I. Isolated frd3 Nucleic Acid Molecules

One aspect of the invention pertains to isolated nucleic acid molecules that encode FRD3 proteins or biologically active portions thereof, as well as nucleic acid fragments sufficient for use as hybridization probes to identify frd3-encoding nucleic acid molecules (e.g., frd3 mRNA) and fragments for use as PCR primers for the amplification or mutation of frd3 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated frd3 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, 2, 4, 5, 7, 8, 20, or a portion thereof, can be isolated using standard molecular biology techniques and the sequence information provided herein. Using all or portion of the nucleic acid sequence of SEQ ID NO:1, 2, 4, 5, 7, 8, or 20, as a hybridization probe, frd3 nucleic acid molecules can be isolated using standard hybridization and cloning techniques (e.g., as described in Ausubel, F. M., Brent, R., Kingston, R. E., Moore, D. D., Seidman, J. G., Smith, J. A., and Struhl, K. (2002) Current Protocols in Molecular Biology. (New York, N.Y.: John Wiley & Sons).

Moreover, a nucleic acid molecule encompassing all or a portion of SEQ ID NO:1, 2, 4, 5, 7, 8, or 20, can be isolated by the polymerase chain reaction (PCR) using synthetic oligonucleotide primers designed based upon the sequence of SEQ ID NO: 1, 2, 4, 5, 7, 8, or 20.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to frd3 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO: 1, 2, 4, 5, 7, 8, or 20. This cDNA may comprise sequences encoding the FRD3 protein, i.e., "the coding region," from nucleotides 118–1698 of SEQ ID NO:2, nucleotides 118–1182 of SEQ ID NO:5, nucleotides 118–870 of SEQ ID NO:8, or nucleotides 118–1698 of SEQ ID NO:20, as well as 5' untranslated sequences (nucleotides 1–117 of SEQ ID NOs:2, 5, 8, or 20) and 3' untranslated sequences (nucleotides 1699–1868 of SEQ ID NO:2, nucleotides 1183–1867 of SEQ ID NO:5, nucleotides 871–1950 of SEQ ID NO:8, or nucleotides 1699–11868 of SEQ ID NO:20). Alternatively, the nucleic acid molecule can comprise only the coding region of SEQ ID NO:2, 5, or 8 (e.g., nucleotides 118–1698 of SEQ ID NO:2, nucleotides 118–1182 of SEQ ID NO:5, nucleotides 118–870 of SEQ ID NO:8, or nucleotides 118–1698 of SEQ ID NO:20).

In another preferred embodiment, an isolated nucleic acid molecule of the invention comprises a nucleic acid molecule which is a complement of the nucleotide sequence shown in SEQ ID NO: 1, 2, 4, 5, 7, 8, or 20, or a portion of any of these nucleotide sequences. A nucleic acid molecule which is complementary to the nucleotide sequence shown in SEQ ID NO: 1, 2, 4, 5, 7, 8, or 20, is one which is sufficiently complementary to the nucleotide sequence shown in SEQ ID NO: 1, 2, 4, 5, 7, 8, or 20, such that it can hybridize to the nucleotide sequence shown in SEQ ID NO: 1, 2, 4, 5, 7, 8, or 20, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 96%, 97%, 98%, 99% or more identical to the entire length of the nucleotide sequence shown in SEQ ID NO: 1, 2, 4, 5, 7, 8, or 20, or a portion of any of these nucleotide sequences.

Moreover, the nucleic acid molecule of the invention can comprise only a portion of the nucleic acid sequence of SEQ ID NO: 1, 2, 4, 5, 7, 8, or 20, for example, a fragment which can be used as a probe or primer or a fragment encoding a portion of a FRD3 protein, e.g., a biologically active portion of a FRD3 protein. The nucleotide sequences determined from the cloning of frd3 genes allow for the generation of probes and primers designed for use in identifying and/or cloning other FRD3 family members, as well as FRD3 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO: 1, 2, 4, 5, 7, 8, or 20, of an anti-sense sequence of SEQ ID NO: 1, 2, 4, 5, 7, 8, or 20, or of a naturally occurring allelic variant or mutant of SEQ ID NO: 1, 2, 4, 5, 7, 8, or 20. In one embodiment, a nucleic acid molecule of the present invention comprises a nucleotide sequence which is greater than 50–100, 100–150, 150–200, 200–250, 250–300, 300–350, 350–400, 400–450, 450–500, 500–550, 550–600, 600–650, 653, 653–700, 700–750, 750–800, 800–850, 850–900, 900–950, 950–1000, 1000–1050, 1050–1100, 1100–1150, 1150–1200, 1200–1250, 1250–1300, 1300–1350, 1350–1400, 1400–1450, 1450–1500, 1500–1550, 1550–1600, 1600–1650, 1650–1700, 1700–1750 or more nucleotides in length and hybridizes under stringent hybridization conditions to a nucleic acid molecule of SEQ ID NO: 1, 2, 4, 5, 7, 8, or 20.

Probes based on the frd3 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a FRD3 protein, such as by measuring a level of a frd3-encoding nucleic acid in a sample of cells from a subject e.g., detecting frd3 mRNA levels or determining whether a genomic frd3 gene has been mutated or deleted.

A nucleic acid fragment encoding a "biologically active portion of a FRD3 protein" can be prepared by isolating a portion of the nucleotide sequence of SEQ ID NO: 1, 2, 4, 5, 7, 8, or 20 which encodes a polypeptide having a FRD3 biological activity (the biological activities of the FRD3 proteins are described herein), expressing the encoded portion of the FRD3 protein (e.g., by recombinant expression in vitro) and assessing the activity of the encoded portion of the FRD3 protein. Biologically active portions of a FRD3 protein can be identified, for example, by a ferric chelate reductase assay (Yi and Guerinot (1996) Plant J. 10:835–844).

The invention further encompasses nucleic acid molecules that differ from the nucleotide sequence shown in SEQ ID NO: 1, 2, 4, 5, 7, 8, or 20 due to degeneracy of the genetic code and thus encode the same FRD3 proteins as those encoded by the nucleotide sequence shown in SEQ ID NO: 1, 2, 4, 5, 7, 8, or 20. In another embodiment, an isolated nucleic acid molecule of the invention has a nucleotide sequence encoding a protein having an amino acid sequence shown in SEQ ID NO:3, 6, 9, or 10.

In addition to the frd3 nucleotide sequences shown in SEQ ID NO: 1, 2, 4, 5, 7, 8, or 20, it will be appreciated by those skilled in the art that DNA sequence polymorphisms that lead to changes in the amino acid sequences of the FRD3 proteins may exist within a population (e.g., a plant population). Such genetic polymorphism in the frd3 genes may exist within a population due to natural allelic variation. As used herein, the terms "gene" and "recombinant gene" refer to nucleic acid molecules which include an open reading frame encoding a FRD3 protein, preferably an *Arabidopsis* FRD3 protein, and can further include non-coding regulatory sequences, and introns.

Allelic variants of FRD3 include both functional and non-functional FRD3 proteins. Functional allelic variants are naturally occurring amino acid sequence variants of the FRD3 protein that retain FRD3-mediated activity. Functional allelic variants will typically contain only conservative substitution of one or more amino acids of SEQ ID NO:3, 6, 9, or 10, or substitution, deletion or insertion of non-critical residues in non-critical regions of the protein.

Non-functional allelic variants are naturally occurring amino acid sequence variants of the FRD3 protein that do not retain FRD3-mediated activity as described herein. Non-functional allelic variants will typically contain a non-conservative substitution, a deletion, or insertion or premature truncation of the amino acid sequence of SEQ ID NO:3, 6, 9, or 10, or a substitution, insertion or deletion in critical residues or critical regions of the protein.

The present invention further provides human orthologues of the FRD3 protein. Orthologues of the FRD3 protein are proteins that are isolated from human organisms and possess the same FRD3 activities of the FRD3 protein. Orthologues of the FRD3 protein can readily be identified as comprising an amino acid sequence that is substantially identical to SEQ ID NO:3, 6, 9, or 10.

Moreover, nucleic acid molecules encoding other FRD3 family members and, thus, which have a nucleotide sequence which differs from the frd3 sequence of SEQ ID NO: 1, 2, 4, 5, 7, 8, or 20, are intended to be within the scope of the invention. For example, other frd3 cDNAs can be identified based on the nucleotide sequences of frd3. Moreover, nucleic acid molecules encoding FRD3 proteins from different species, and which, thus, have a nucleotide sequence which differs from the frd3 sequence of SEQ ID NO: 1, 2, 4, 5, 7, 8, or 20 are intended to be within the scope of the invention. For example, a genomic library from several other dicots, e.g., tomato, broccoli or mustard, can be screened to obtain genes of the FRD3 family. Positive clones are then analyzed and sequenced to obtain additional family members.

Nucleic acid molecules corresponding to natural allelic variants and homologues of the frd3 cDNAs of the invention can be isolated based on their homology to the frd3 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the frd3 cDNAs of the invention can further be isolated by mapping to the same chromosome or locus as the frd3 genes.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO: 1, 2, 4, 5, 7, 8, or 20. In other embodiment, the nucleic acid is at least 50–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1050, 1050–1100, 1100–1150, 1150–1200, 1200–1250, 1250–1300, 1300–1350, 1350–1400, 1400–1450, 1450–1500, 1500–1550, 1550–1600, 1600–1650, 1650–1700, 1700–1750 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (2002), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\% \text{ G+C})-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5 M $NaH_2PO_4$, 7% SDS at about 65° C., followed by one or more washes at 0.02 M $NaH_2PO_4$, 1% SDS at 65° C., see e.g., Church and Gilbert (1984) *Proc. Natl. Acad. Sci. USA* 81:1991–1995, (or, alternatively, 0.2×SSC, 1% SDS).

In addition to naturally-occurring allelic variants of the FRD3 sequences that may exist in the population, the skilled artisan will further appreciate that changes can be introduced by mutation into the nucleotide sequences of SEQ ID NO: 1, 2, 4, 5, 7, 8, or 20, thereby leading to changes in the amino acid sequence of the encoded FRD3 proteins, without altering the functional ability of the FRD3 proteins. For example, nucleotide substitutions leading to amino acid substitutions at "non-essential" amino acid residues can be made in the sequence of SEQ ID NO: 1, 2, 4, 5, 7, 8, or 20. A "non-essential" amino acid residue is a residue that can be altered from FRD3 sequences (e.g., the sequence of SEQ ID NOs:3, 6, 9, or 10) without altering the biological activity thereof, whereas an "essential" amino acid residue is required for biological activity. For example, amino acid residues that are conserved among the FRD3 proteins of the present invention, e.g., those present in a transmembrane domain, are predicted to be particularly unamenable to alteration. Furthermore, additional amino acid residues that are conserved between the FRD3 proteins of the present invention and other members of the FRD3 family are not likely to be amenable to alteration.

Accordingly, another aspect of the invention pertains to nucleic acid molecules encoding FRD3 proteins that contain changes in amino acid residues that are not essential for activity. Such FRD3 proteins differ in amino acid sequence from SEQ ID NO:3, 6, 9, or 10, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95%, 96%, 97%, 98%, 99% or more identical to SEQ ID NO:3, 6, 9, or 10.

An isolated nucleic acid molecule encoding a FRD3 protein identical to the protein of SEQ ID NO:3, 6, 9, or 10 can be created by introducing one or more nucleotide substitutions, additions or deletions into the nucleotide sequence of SEQ ID NO: 1, 2, 4, 5, 7, 8, or 20 such that one or more amino acid substitutions, additions or deletions are introduced into the encoded protein. Mutations can be introduced into SEQ ID NO: 1, 2, 4, 5, 7, 8, or 20 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a FRD3 protein is preferably replaced with another amino acid residue from the same side chain family. Alternatively, in another embodiment, mutations can be introduced randomly along all or part of a frd3 coding sequence, such as by saturation mutagenesis, and the resultant mutants can be screened for FRD3 biological activity to identify mutants that retain activity. Following mutagenesis of SEQ ID NO: 1, 2, 4, 5, 7, 8, or 20, the encoded protein can be expressed recombinantly and the activity of the protein can be determined.

In a preferred embodiment, a mutagenized FRD3 protein can be assayed for the ability to: (1) express metal deficiency responses, e.g., iron deficiency responses, under conditions of metal sufficiency, (2) misexpress ferric chelate reductase activity, (3) overaccumulate metals, e.g., iron, or (4) cause chlorosis.

In addition to the nucleic acid molecules encoding FRD3 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire frd3 coding strand, or to only a portion thereof. In one embodiment, an antisense nucleic acid molecule is antisense to a "coding region" of the coding strand of a nucleotide sequence encoding frd3. The term "coding region" refers to the region of the nucleotide sequence comprising codons which are translated into amino acid residues (e.g., the coding region of frd3-1 corresponds to nucleotides 118–1698 of SEQ ID NO:2, the coding region of frd3-2 corresponds to nucleotides 118–1182 of SEQ ID NO:5, and the coding region of frd3-3 corresponds to nucleotides 118–870 of SEQ ID NO:8). In another embodiment, the antisense nucleic acid molecule is antisense to a "noncoding region" of the coding strand of a nucleotide sequence encoding FRD3 polypeptides. The term "noncoding region" refers to 5' and 3' sequences which flank the coding region that are not translated into amino acids (i.e., also referred to as 5' and 3' untranslated regions).

Given the coding strand sequences encoding FRD3 polypeptides disclosed herein, antisense nucleic acids of the invention can be designed according to the rules of Watson and Crick base pairing. The antisense nucleic acid molecule can be complementary to the entire coding region of frd3 mRNA, but more preferably is an oligonucleotide which is antisense to only a portion of the coding or noncoding region of frd3 mRNA. For example, the antisense oligonucleotide can be complementary to the region surrounding the translation start site of frd3 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Another aspect of the invention pertains to double stranded RNA comprising frd3-specific sequences in the sense and antisense orientations and capable of duplex formation with frd3 genes. As further described in Chuang and Meryerowitz (2000) PNAS 97(9):4985–4990, such double stranded RNA can be used to mediate interference with the expression of certain genes.

The antisense nucleic acid molecules of the invention are typically administered to a subject or generated in situ such that they hybridize with or bind to cellular mRNA and/or genomic DNA encoding a FRD3 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave frd3 mRNA transcripts to thereby inhibit translation of frd3 mRNA. A ribozyme having specificity for a frd3-encoding nucleic acid can be designed based upon the nucleotide sequence of a frd3 cDNA disclosed herein (i.e., SEQ ID NO: 3). For example, a derivative of a *Tetrahymena* L-19 IVS RNA can be constructed in which the nucleotide sequence of the active site is complementary to the nucleotide sequence to be cleaved in a frd3-encoding mRNA. See, e.g., Cech et al. U.S. Pat. No. 4,987,071; and Cech et al. U.S. Pat. No. 5,116,742. Alternatively, frd3 mRNA can be used to select a catalytic RNA having a specific ribonuclease activity from a pool of RNA molecules. See, e.g., Bartel, D. and Szostak, J. W. (1993) *Science* 261:1411–1418.

Alternatively, frd3 gene expression can be inhibited by targeting nucleotide sequences complementary to the regulatory region of frd3 nucleic acid molecules to form triple helical structures that prevent transcription of a frd3 gene in target cells. See generally, Helene, C. (1991) *Anticancer Drug Des.* 6(6): 569–84; Helene, C. et al. (1992) *Ann. N.Y. Acad. Sci.* 660:27–36; and Maher, L. J. (1992) *Bioassays* 14(12):807–15.

In yet another embodiment, the frd3 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of frd3 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of frd3 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of FRD3 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of frd3 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous frd3 gene within a cell line or microorganism may be modified by inserting a heterologous DNA regulatory element into the genome of a stable cell line or cloned microorganism such that the inserted regulatory element is operatively linked with the endogenous frd3 gene. For example, an endogenous frd3 gene which is normally "transcriptionally silent", i.e., a frd3 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous frd3 gene may be activated by insertion of a promiscuous regulatory element that works across cell types.

A heterologous regulatory element may be inserted into a stable cell line or cloned microorganism, such that it is operatively linked with an endogenous frd3 gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated FRD3 Proteins and Anti-FRD3 Antibodies

One aspect of the invention pertains to isolated FRD3 proteins, and biologically active portions thereof, as well as polypeptide fragments suitable for use as immunogens to raise anti-FRD3 antibodies. In one embodiment, native FRD3 proteins can be isolated from cells or tissue sources by an appropriate purification scheme using standard protein purification techniques. In another embodiment, FRD3 proteins are produced by recombinant DNA techniques. Alternative to recombinant expression, a FRD3 protein or polypeptide can be synthesized chemically using standard peptide synthesis techniques.

An "isolated" or "purified" protein or biologically active portion thereof is substantially free of cellular material or other contaminating proteins from the cell or tissue source from which the FRD3 protein is derived, or substantially free from chemical precursors or other chemicals when chemically synthesized. The language "substantially free of cellular material" includes preparations of FRD3 protein in which the protein is separated from cellular components of the cells from which it is isolated or recombinantly produced. In one embodiment, the language "substantially free of cellular material" includes preparations of FRD3 protein having less than about 30% (by dry weight) of non-FRD3 protein (also referred to herein as a "contaminating protein"), more preferably less than about 20% of non-FRD3 protein, still more preferably less than about 10% of non-FRD3 protein, and most preferably less than about 5% non-FRD3 protein. When the FRD3 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of FRD3 protein in which the protein is separated from chemical precursors or other chemicals which are involved in the synthesis of the protein. In one embodiment, the language "substantially free of chemical precursors or other chemicals" includes preparations of FRD3 protein having less than about 30% (by dry weight) of chemical precursors or non-FRD3 chemicals, more preferably less than about 20% chemical precursors or non-FRD3 chemicals, still more preferably less than about 10% chemical precursors or non-FRD3 chemicals, and most preferably less than about 5% chemical precursors or non-FRD3 chemicals.

As used herein, a "biologically active portion" of a FRD3 protein includes a fragment of a FRD3 protein which participates in an interaction between a FRD3 molecule and a non-FRD3 molecule. Biologically active portions of a FRD3 protein include peptides comprising amino acid sequences sufficiently identical to or derived from the amino acid sequence of the FRD3 protein, e.g., the amino acid sequence shown in SEQ ID NO:3, 6, 9, or 10, which include less amino acids than the full length FRD3 protein, and exhibit at least one activity of a FRD3 protein. Typically, biologically active portions comprise a domain or motif with at least one activity of the FRD3 protein, e.g., modulation of metal concentrations. A biologically active portion of a FRD3 protein can be a polypeptide which is, for example, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775 or more amino acids in length. Biologically active portions of a FRD3 protein can be used as targets for developing agents which modulate a FRD3 mediated activity, e.g., modulation of metal concentrations.

In one embodiment, a biologically active portion of a FRD3 protein comprises at least one transmembrane domain. Moreover, other biologically active portions, in which other regions of the protein are deleted, can be prepared by recombinant techniques and evaluated for one or more of the functional activities of a native FRD3 protein.

In a preferred embodiment, the FRD3 protein has an amino acid sequence shown in SEQ ID NO:3, 6, 9, or 10. In other embodiments, the FRD3 protein is substantially identical to SEQ ID NO:3, 6, 9, or 10 and retains the functional activity of the protein of SEQ ID NO:3, 6, 9, or 10 yet differs in amino acid sequence due to natural allelic variation or mutagenesis, as described in detail in subsection I above. Accordingly, in another embodiment, the FRD3 protein is a protein which comprises an amino acid sequence at least about 50%, 55%, 60%, 65%, 70%, 75%, 80%, 85%, 90%, 95%, 96%, 97%, 98%, 99% or more identical to SEQ ID NO: 3, 6, 9, or 10.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the FRD3 amino acid sequence of SEQ ID NO:2 having 526 amino acid residues, at least 158, preferably at least 210, more preferably at least 263, even more preferably at least 316, even more preferably at least 368, and even more preferably at least 421 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at the GCG website), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the GCG website), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.*, 4: 11–17 (1988)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to frd3 nucleic acid molecules of the invention. BLAST protein searches can be performed with the XBLAST program, score=100, wordlength=3 to obtain amino acid sequences homologous to FRD3 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See the NCBI website.

The invention also provides FRD3 chimeric or fusion proteins. As used herein, a FRD3 "chimeric protein" or "fusion protein" comprises a FRD3 polypeptide operatively linked to a non-FRD3 polypeptide. A "FRD3 polypeptide" refers to a polypeptide having an amino acid sequence corresponding to a FRD3 molecule, whereas a "non-FRD3 polypeptide" refers to a polypeptide having an amino acid sequence corresponding to a protein which is not substantially homologous to the FRD3 protein, e.g., a protein which is different from the FRD3 protein and which is derived from the same or a different organism. Within a FRD3 fusion protein the FRD3 polypeptide can correspond to all or a portion of a FRD3 protein. In a preferred embodiment, a FRD3 fusion protein comprises at least one biologically active portion of a FRD3 protein. In another preferred embodiment, a FRD3 fusion protein comprises at least two biologically active portions of a FRD3 protein. Within the fusion protein, the term "operatively linked" is intended to indicate that the FRD3 polypeptide and the non-FRD3 polypeptide are fused in-frame to each other. The non-FRD3 polypeptide can be fused to the N-terminus or C-terminus of the FRD3 polypeptide.

For example, in one embodiment, the fusion protein is a GST-FRD3 fusion protein in which the FRD3 sequences are fused to the C-terminus of the GST sequences. Such fusion proteins can facilitate the purification of recombinant FRD3.

In another embodiment, the fusion protein is a FRD3 protein containing a heterologous signal sequence at its N-terminus. In certain host cells (e.g., mammalian host cells), expression and/or secretion of FRD3 can be increased through use of a heterologous signal sequence.

The FRD3 fusion proteins of the invention can be incorporated into pharmaceutical compositions and administered to a subject in vivo. The FRD3 fusion proteins can be used to affect the bioavailability of a FRD3 substrate. Use of FRD3 fusion proteins may be useful therapeutically for the treatment of disorders caused by, for example, (i) aberrant modification or mutation of a gene encoding a FRD3 protein; (ii) mis-regulation of the frd3 gene; and (iii) aberrant post-translational modification of a FRD3 protein.

Moreover, the FRD3 fusion proteins of the invention can be used as immunogens to produce anti-FRD3 antibodies in a subject, to purify FRD3 ligands and in screening assays to identify molecules which inhibit the interaction of FRD3 with a FRD3 substrate.

Preferably, a FRD3 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 2002). Moreover, many expression vectors are commercially available that already encode a fusion moiety (e.g., a GST polypeptide). A frd3-encoding nucleic acid can be cloned into such an expression vector such that the fusion moiety is linked in-frame to the FRD3 protein.

The present invention also pertains to variants of the FRD3 proteins which function as either FRD3 agonists (mimetics) or as FRD3 antagonists. Variants of the FRD3 proteins can be generated by mutagenesis, e.g., discrete point mutation or truncation of a FRD3 protein. An agonist of the FRD3 proteins can retain substantially the same, or a subset, of the biological activities of the naturally occurring form of a FRD3 protein. An antagonist of a FRD3 protein can inhibit one or more of the activities of the naturally occurring form of the FRD3 protein by, for example, competitively modulating a FRD3-mediated activity of a FRD3 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the FRD3 protein.

In one embodiment, variants of a FRD3 protein which function as either FRD3 agonists (mimetics) or as FRD3 antagonists can be identified by screening combinatorial libraries of mutants, e.g., truncation mutants, of a FRD3 protein for FRD3 protein agonist or antagonist activity. In one embodiment, a variegated library of FRD3 variants is generated by combinatorial mutagenesis at the nucleic acid level and is encoded by a variegated gene library. A variegated library of FRD3 variants can be produced by, for example, enzymatically ligating a mixture of synthetic oligonucleotides into gene sequences such that a degenerate set of potential frd3 sequences is expressible as individual polypeptides, or alternatively, as a set of larger fusion proteins (e.g., for phage display) containing the set of frd3 sequences therein. There are a variety of methods which can be used to produce libraries of potential FRD3 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential FRD3 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a FRD3 protein coding sequence can be used to generate a variegated population of FRD3 fragments for screening and subsequent selection of variants of a FRD3 protein. In one embodiment, a library of coding sequence fragments can be generated by treating a double stranded PCR fragment of a frd3 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of FRD3 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of FRD3 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify FRD3 variants (Arkin and Yourvan (1992) *Proc. Natl. Acad. Sci. USA* 89:7811–7815; Delgrave et al. (1993) *Protein Engineering* 6(3): 327–331).

In one embodiment, cell based assays can be exploited to analyze a variegated FRD3 library. For example, a library of expression vectors can be transfected into a cell line which ordinarily responds to a FRD3 ligand in a particular FRD3 ligand-dependent manner. The transfected cells are then contacted with a FRD3 ligand and the effect of expression of the mutant on, e.g., modulation of iron concentrations can be detected. Plasmid DNA can then be recovered from the cells which score for inhibition, or alternatively, potentiation of signaling by the FRD3 ligand, and the individual clones further characterized.

An isolated FRD3 protein, or a portion or fragment thereof, can be used as an immunogen to generate antibodies that bind FRD3 using standard techniques for polyclonal and monoclonal antibody preparation. A full-length FRD3 protein can be used or, alternatively, the invention provides antigenic peptide fragments of FRD3 for use as immunogens. The antigenic peptide of FRD3 comprises at least 8 amino acid residues of the amino acid sequence shown in SEQ ID NO:3, 6, 9, or 10 and encompasses an epitope of FRD3 such that an antibody raised against the peptide forms a specific immune complex with the FRD3 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of FRD3 that are located on the surface of the protein, e.g., hydrophilic regions, as well as regions with high antigenicity.

A FRD3 immunogen typically is used to prepare antibodies by immunizing a suitable subject, (e.g., rabbit, goat, mouse or other mammal) with the immunogen. An appropriate immunogenic preparation can contain, for example, recombinantly expressed FRD3 protein or a chemically synthesized FRD3 polypeptide. The preparation can further include an adjuvant, such as Freund's complete or incomplete adjuvant, or similar immunostimulatory agent. Immunization of a suitable subject with an immunogenic FRD3 preparation induces a polyclonal anti-FRD3 antibody response.

Accordingly, another aspect of the invention pertains to anti-FRD3 antibodies. The term "antibody" as used herein refers to immunoglobulin molecules and immunologically active portions of immunoglobulin molecules, i.e., molecules that contain an antigen binding site which specifically binds (immunoreacts with) an antigen, such as FRD3. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind FRD3 molecules. The term "monoclonal antibody" or "monoclonal antibody composition", as used herein, refers to a population of antibody molecules that contain only one species of an antigen binding site capable of immunoreacting with a particular epitope of FRD3. A monoclonal antibody composition thus typically displays a single binding affinity for a particular FRD3 protein with which it immunoreacts.

Polyclonal anti-FRD3 antibodies can be prepared as described above by immunizing a suitable subject with a FRD3 immunogen. The anti-FRD3 antibody titer in the immunized subject can be monitored over time by standard techniques, such as with an enzyme linked immunosorbent assay (ELISA) using immobilized FRD3. If desired, the antibody molecules directed against FRD3 can be isolated from the mammal (e.g., from the blood) and further purified by well known techniques, such as protein A chromatography to obtain the IgG fraction. At an appropriate time after immunization, e.g., when the anti-FRD3 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a FRD3 immunogen as described above, and the culture supernatants of the resulting hybridoma cells are screened to identify a hybridoma producing a monoclonal antibody that binds FRD3.

Any of the many well known protocols used for fusing lymphocytes and immortalized cell lines can be applied for the purpose of generating an anti-FRD3 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind FRD3, e.g., using a standard ELISA assay.

Alternative to preparing monoclonal antibody-secreting hybridomas, a monoclonal anti-FRD3 antibody can be identified and isolated by screening a recombinant combinatorial immunoglobulin library (e.g., an antibody phage display library) with FRD3 to thereby isolate immunoglobulin library members that bind FRD3. Kits for generating and screening phage display libraries are commercially available (e.g., the Pharmacia *Recombinant Phage Antibody System*, Catalog No. 27–9400–01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al (1993) *EMBO J* 12:725–734; Hawkins et al. (1992) *J. Mol. Biol.* 226: 889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-FRD3 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-FRD3 antibody (e.g., monoclonal antibody) can be used to isolate FRD3 by standard techniques, such as affinity chromatography or immunoprecipitation. An anti-FRD3 antibody can facilitate the purification of natural FRD3 from cells and of recombinantly produced FRD3 expressed in host cells. Moreover, an anti-FRD3 antibody can be used to detect FRD3 protein (e.g., in a cellular lysate or cell supernatant) in order to evaluate the abundance and pattern of expression of the FRD3 protein. Anti-FRD3 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a FRD3 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., FRD3 proteins, mutant forms of FRD3 proteins, fusion proteins, and the like).

The recombinant expression vectors of the invention can be designed for expression of FRD3 proteins in prokaryotic or eukaryotic cells. For example, FRD3 proteins can be expressed in bacterial cells such as E. coli, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in FRD3 activity assays, (e.g., direct assays or competitive assays described in detail below), or to generate antibodies specific for FRD3 proteins, for example. In a preferred embodiment, a FRD3 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the FRD3 expression vector is a yeast expression vector. Examples of vectors for expression in yeast *S. cerevisiae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, FRD3 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), lung specific promoters, and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to frd3 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al, Antisense RNA as a molecular tool for genetic analysis, *Reviews—Trends in Genetics*, Vol. 1(1) 1986.

Another aspect of the invention pertains to host cells into which a frd3 nucleic acid molecule of the invention is introduced, e.g., a frd3 nucleic acid molecule within a recombinant expression vector or a frd3 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a FRD3 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a FRD3 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a FRD3 protein. Accordingly, the invention further provides methods for producing a FRD3 protein using the host cells of the invention. In one embodiment, the method comprises culturing the host cell of the invention (into which a recombinant expression vector encoding a FRD3 protein has been introduced) in a suitable medium such that a FRD3 protein is produced. In another embodiment, the method further comprises isolating a FRD3 protein from the medium or the host cell.

The host cells of the invention can also be used to produce transgenic plants. As used herein, the term "transgenic" refers to a cell, group of cells, or organism, e.g., plant or animal, which includes a DNA sequence which is inserted by artifice therein. If the DNA sequence is inserted into a cell, the sequence becomes part of the genome of the organism which develops from that cell. For example, the transgenic organisms are generally transgenic plants and the DNA transgene is inserted artificially into the nuclear or plastidic genome. As used herein, the term "transgene" refers to any piece of DNA which is artificially inserted into a cell, group of cells, or organism, e.g., plant or animal, and becomes a part of the genome of the organism which develops from that cell. Such a transgene can include a gene which is partly or entirely heterologous to the transgenic organism, or can include a gene homologous to an endogenous gene of the organism.

For example, in one embodiment, a host cell of the invention is a plant cell, e.g., a protoplast, into which frd3-coding sequences have been introduced. As used herein, a "plant cell" refers to any self-propagating cell bounded by a semi-permeable membrane and containing a plastid. Such a cell requires a cell wall if further propagation is desired. For example, plant cells of the invention include algae, cyanobacteria, seed suspension cultures, embryos, meristematic regions, callus tissue, leaves, roots, shoots, gametophytes, sporophytes, pollen, and microspores. As used herein, the term "plant" refers to either a whole plant, a plant part, a plant cell, or a group of plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The transformation of plants in accordance with the invention can be carried out in essentially any of the various ways known to those skilled in the art of plant molecular biology. See, in general, *Methods in Enzymology* Vol. 153 ("Recombinant DNA Part D") 1987, Wu and Grossman Eds., Academic Press and European Patent Application EP 693554.

Selection of an appropriate vector is relatively simple, as the constraints are minimal. The minimal traits of the vector are that the desired nucleic acid sequence be introduced in a relatively intact state. Thus any vector which produces a plant carrying the introduced DNA sequence is sufficient. Also, any vector which introduces a substantially intact RNA which can ultimately be converted into a stably maintained DNA sequence can be used to transform a plant cell.

Even a naked piece of DNA confers the properties of this invention, though at low efficiency. The decision as to whether to use a vector, or which vector to use, is determined by the method of transformation selected.

If naked nucleic acid introduction methods are chosen, then the vector need be no more than the minimal nucleic acid sequences necessary to confer the desired traits, without the need for additional other sequences. Thus, the possible vectors include the Ti plasmid vectors, shuttle vectors designed merely to maximally yield high numbers of copies, episomal vectors containing minimal sequences necessary for ultimate replication once transformation has occurred, transposon vectors, homologous recombination vectors, mini-chromosome vectors, and viral vectors, including the possibility of RNA forms of the gene sequences. The selection of vectors and methods to construct them are commonly known to persons of ordinary skill in the art and are described in general technical references (*Methods in Enzymology Vol.* 153 ("Recombinant DNA Part D") 1987, Wu and Grossman Eds., Academic Press).

In one embodiment, the foreign nucleic acid is mechanically transferred by microinjection directly into plant cells by use of micropipettes. Alternatively, the foreign nucleic acid can be transferred into the plant cell by using polyethylene glycol. This forms a precipitation complex with the genetic material that is taken up by the cell (Paszkowski et al. (1984) *EMBO J.* 3:2712–22).

In another embodiment, foreign nucleic acid can be introduced into the plant cells by electroporation (Fromm et al. (1985) *Proc. Natl. Acad. Sci. USA* 82:5824). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells with the transformed gene can be accomplished using phenotypic markers.

Cauliflower mosaic virus (CaMV) can also be used as a vector for introducing the foreign nucleic acid into plant cells (Hohn et al. (1982) "Molecular Biology of Plant Tumors," Academic Press, New York, pp. 549–560; Howell, U.S. Pat. No. 4,407,956). CaMV viral DNA genome is inserted into a parent bacterial plasmid creating a recombinant DNA molecule which can be propagated in bacteria. After cloning, the recombinant plasmid again can be cloned and further modified by introduction of the desired DNA sequence into the unique restriction site of the linker. The modified viral portion of the recombinant plasmid is then excised from the parent bacterial plasmid, and used to inoculate the plant cells or plants.

Another method of introduction of foreign nucleic acid into plant cells is high velocity ballistic penetration by small particles with the nucleic acid either within the matrix of small beads or particles, or on the surface (Klein et al. (1987) *Nature* 327:70–73). Although typically only a single introduction of a new nucleic acid segment is required, this method particularly provides for multiple introductions.

A preferred method of introducing the nucleic acids into plant cells is to infect a plant cell, an explant, a meristem or a seed with *Agrobacterium tumefaciens* transformed with the nucleic acid. Under appropriate conditions known in the art, the transformed plant cells are grown to form shoots, roots, and develop further into plants. The nucleic acids can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al. (1984) "Inheritance of Functional Foreign Genes in Plants," *Science* 233:496–498; Fraley et al. (1983) *Proc. Natl. Acad. Sci. USA* 80:4803).

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without affecting its transferring ability. By removing the tumor-causing genes so that they no longer interfere, the modified Ti plasmid can then be used as a vector for the transfer of the gene constructs of the invention into an appropriate plant cell.

There are presently at least three different ways to transform plant cells with *Agrobacterium*: (1) co-cultivation of *Agrobacterium* with cultured isolated protoplasts; (2) transformation of cells or tissues with *Agrobacterium*; or (3) transformation of seeds, apices or meristems with *Agrobacterium*. The first method requires an established culture system that allows culturing protoplasts and plant regeneration from cultured protoplasts. The second method requires that the plant cells or tissues can be transformed by *Agrobacterium* and that the transformed cells or tissues can be induced to regenerate into whole plants. The third method requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and can be used in this invention.

All plants from which protoplasts can be isolated and cultured to give whole regenerated plants can be transformed by the present invention so that whole plants are recovered which contain the transferred foreign gene. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum,* and *Datura.*

Practically all plants can be regenerated from cultured cells or tissues. The term "regeneration" as used herein, means growing a whole plant from a plant cell, a group of plant cells, a plant part or a plant piece (e.g. from a protoplast, callus, or tissue part) (*Methods in Enzymology* Vol. 153 ("Recombinant DNA Part D") 1987, Wu and Grossman Eds., Academic Press; also *Methods in Enzymology,* Vol. 118; and Klee et al., (1987) *Annual Review of plant Physiology,* 38:467–486).

Plant regeneration from cultural protoplasts is described in Evans et al., "Protoplasts Isolation and Culture," *Handbook of Plant Cell Cultures* 1:124–176 (MacMillan Publishing Co. New York 1983); M. R. Davey, "Recent Developments in the Culture and Regeneration of Plant Protoplasts," *Protoplasts* (1983)-Lecture Proceedings, pp. 12–29, (Birkhauser, Basal 1983); P. J. Dale, "Protoplast Culture and Plant Regeneration of Cereals and Other Recalcitrant Crops," *Protoplasts* (1983)-Lecture Proceedings, pp. 31–41, (Birkhauser, Basel 1983); and H. Binding, "Regeneration of Plants," *Plant Protoplasts,* pp. 21–73, (CRC Press, Boca Raton 1985).

Regeneration from protoplasts varies from species to species of plants, but generally a suspension of transformed protoplasts containing copies of the exogenous sequence is first generated. In certain species, embryo formation can then be induced from the protoplast suspension, to the stage of ripening and germination as natural embryos. The culture media can contain various amino acids and hormones, such as auxin and cytokinins. It can also be advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In vegetatively propagated crops, the mature transgenic plants are propagated by the taking of cuttings or by tissue culture techniques to produce multiple identical plants for trialling, such as testing for production characteristics. Selection of a desirable transgenic plant is made and new varieties are obtained thereby, and propagated vegetatively for commercial sale. In seed propagated crops, the mature transgenic plants are self crossed to produce a homozygous inbred plant. The inbred plant produces seed containing the gene for the newly introduced foreign gene activity level. These seeds can be grown to produce plants that have the selected phenotype. The inbreds according to this invention can be used to develop new hybrids. In this method a selected inbred line is crossed with another inbred line to produce the hybrid.

Parts obtained from the regenerated plant, such as flowers, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences. Progeny and variants, and mutants of the regenerated plants are also included within the scope of this invention.

However, any additional attached vector sequences which confers resistance to degradation of the nucleic acid fragment to be introduced, which assists in the process of genomic integration or provides a means to easily select for those cells or plants which are transformed are advantageous and greatly decrease the difficulty of selecting useable transgenic plants or plant cells.

Selection of transgenic plants or plant cells is typically based upon a visual assay, such as observing color changes (e.g., a white flower, variable pigment production, and uniform color pattern on flowers or irregular patterns), but can also involve biochemical assays of either enzyme activity or product quantitation. Transgenic plants or plant cells are grown into plants bearing the plant part of interest and the gene activities are monitored, such as by visual appearance (for flavonoid genes) or biochemical assays (Northern blots); Western blots; enzyme assays and flavonoid compound assays, including spectroscopy, see, Harborne et al. (Eds.), (1975) *The Flavonoids*, Vols. 1 and 2, [Acad. Press]). Appropriate plants are selected and further evaluated. Methods for generation of genetically engineered plants are further described in U.S. Pat. Nos. 5,283,184, 5,482,852, and European Patent Application EP 693 554.

An example of a commercial application of the transgenic plants of the invention is in agriculture. Iron is an essential nutrient for crop plants because it is required for the activity of iron-containing proteins involved in photosynthesis and respiration. Although iron is abundant in the soil, its acquisition can be difficult under aerobic conditions because it is very insoluble at moderate pH. This issue is important in agriculture because a third of the world's soils are iron-deficient. Therefore, understanding how plants accumulate iron is critical for increased production of crops that would themselves be richer sources of iron in foods. The ability to develop transgenic plants, through manipulation of the frd3 gene and other members of the MATE family, that are more efficient in extracting iron from soil has important agricultural implications.

A second example of a commercial application of the transgenic plants of the invention is in environmental pollution remediation. Removal of toxic metals from contaminated sites is particularly difficult. Unlike organic pollutants, metal pollutants cannot be biodegraded. The current method of removing metals from contaminated sites is excavation, removal of the soil, and burial in a hazardous waste site. Phytoremediation, the technique of using plants to extract metals from soil, is a more economical and environmentally-safe alternative. Genetically engineered plants of the present invention that are created to be metal specific present great potential for this technology. IRT1 or other members of the MATE family can be manipulated in a plant species to allow high-level accumulation of a specific toxic metal from a contaminated soil.

IV. Pharmaceutical Compositions

The transgenic plant in which the expression of a FRD3 polypeptide is altered, or portions thereof, and other agents described herein can be incorporated into pharmaceutical compositions suitable for administration. Such compositions typically comprise the transgenic plant in which the expression of a FRD3 polypeptide is altered, a portion thereof, or agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one embodiment, polypeptides, compositions, transgenic plants or portions thereof, of the invention can be administered to a subject to treat metal-deficiency, e.g., iron- or zinc-deficiency, or can be administered to a subject, e.g., human or animal, as a nutritional supplement, e.g., as a metal source, e.g., as an iron or zinc supplement. The polypeptides, compositions, or plants are administered to the subjects in a biologically compatible form suitable for pharmaceutical administration in vivo. By "biologically compatible form suitable for administration in vivo" is meant a form of the polypeptide, composition, or plant, e.g., transgenic plant, to be administered in which any toxic effects are outweighed by the therapeutic effects of the polypeptide composition or plant. Administration of a therapeutically active or therapeutically effective amount of a polypeptide, composition, or plant of the present invention is defined as an amount effective, at dosages and for periods of time necessary to achieve the desired result. For example, a therapeutically active amount of a transgenic plant in which expression of a FRD3 polypeptide is altered can vary according to factors such as the disease state, age, sex, and weight of the subject, and the ability of the composition to elicit a desired response in the subject. Dosage regimens may be adjusted to provide the optimum therapeutic response. For example, several divided doses can be administered daily or the dose can be proportionally reduced as indicated by the exigencies of the therapeutic situation.

The polypeptides, composition, or plant can be administered in a convenient manner such as by oral administration, e.g., as a nutritional supplement, injection (subcutaneous, intravenous, etc.), and other methods of parenteral administration. Depending on the route of administration, the polypeptide, composition, or plant can be coated in a material to protect it from the action of enzymes, acids and other natural conditions which may inactivate the agent.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the polypeptides, compositions, or plants are prepared with carriers that protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals.

To administer a polypeptide, composition, or plant by other than parenteral administration, it may be necessary to coat it with, or co-administer it with, a material to prevent its inactivation. For example, a transgenic plant in which expression of a FRD3 polypeptide is altered or a portion thereof can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al. (1984) *J. Neuroimmunol* 7:27). Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the polypeptide, composition, or plant in the required amount in an appropriate solvent with one or a combination of ingredients enumerated above, as required, followed by filtered sterilization. Generally, dispersions are prepared by incorporating the polypeptide, composition, or plant into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

V. Uses and Methods of the Invention

The invention further pertains to methods for modulating metal concentration in a biological sample containing the metal or in a subject. These methods include providing a transgenic plant in which expression of a FRD3 polypeptide is altered and contacting the transgenic plant with the biological sample such that the metal concentration in the biological sample is modulated. The term "modulating" as used herein refers to increasing or decreasing the concentration of a metal in a biological sample. As used herein, the term "metal" includes stable metals and radioactive metals such as iron, lead, chromium, mercury, cadmium, cobalt, barium, nickel, molybdenum, copper, arsenic, selenium, zinc, antimony, beryllium, gold, manganese, silver, thallium, tin, rubidium, vanadium, strontium, yttrium, technecium, ruthenium, palladium, indium, cesium, uranium, plutonium, and cerium. The term "metal" is also intended to include a mixture of two or more metals and mixtures of metals and common organic pollutants such as, for example, lead and chromium in combination with nitrophenol, benzene, and/or alkyl benzyl sulfonates (detergents). As used herein the phrase "biological sample" refers to a material, solid or liquid, in which it is desirable to modulate a metal concentration. Examples of biological samples include metal contaminated liquids such as industrial and residential waste streams, water-treatment plant effluents, ground and surface water, diluted sludge and other aqueous streams containing radioactive and nonradioactive metals, as well as soils or sediments. The soils or sediments can include a variety of soil types having wide ranges of water content, organic matter content, mineral content and metal content. As used herein, the phrase "transgenic plant in which expression of a FRD3 polypeptide is altered" refers to a transgenic plant in which a FRD3 polypeptide is misexpressed, e.g., the expression of a FRD3 polypeptide is enhanced, induced, prevented or suppressed. For example, a transgenic plant in which a FRD3 polypeptide is altered, e.g., by misexpression, can be a metal accumulating plant.

"Misexpression", as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

To measure metal accumulation of a plant in a biological sample, seeds of a particular plant to be tested are grown in a greenhouse, the appropriate metal is administered to the plant and soil, and the roots and shoots harvested for routine determination of biomass and metal content. Chemical analysis of metal content in soils and plants is well characterized. See, e.g., Blincoe et al. (1987) *Comm. Soil. Plant Anal.* 18: 687; Baker et al. (1982) "Atomic Absorption Spectrometry," pp. 13–17 in *Methods of Soil Analysis*, part 2, *Am. Soc. Agron.*, Madison, Wis. Metal in plant tissues is preferably assayed with plasma spectrometry, allowing ashing and acid extraction. Metal remaining in the solution is measured, for example, by atomic absorption or plasma spectrometry. See, e.g., Soltanpour et al. (1982) "Optical emission spectrometry," pp. 29–65 in *Methods of soil Analysis*, part 2, *Am. Soc. Agron.*, Madison, Wis.

Other methods of the invention include methods for removing a pollutant from soil, e.g., phytoremediation (Guerinot, M. L. and Salt, D. E. (2001) Plant Physiol. 125: 164–167) These methods include contacting the transgenic plant in which expression of FRD3 polypeptide is altered with the soil such that the pollutant is removed from the soil, i.e., the concentration of the pollutant in the soil prior to contact with the transgenic plant is greater than the concentration of the pollutant in the soil after contact with the transgenic plant. The term "pollutant" as used herein refers to any metal, e.g., radioactive or nonradioactive metal, that is found in the soil at toxic levels. As used herein, the phrase "toxic levels" refers to the concentration of metal which is higher than the concentration at which these metals naturally occur in the soil. Such toxic levels are usually produced by industries and other pollution centers. For example, metals such as mercury, cobalt, lead, arsenic, cadmium, zinc, copper, alone or in combination with other metals and/or detergents, as described above, are known soil pollutants.

Still other methods of the present invention include methods for treating a disorder associated with metal-deficiency, e.g., iron-deficiency or zinc-deficiency, in a subject. These methods include administering to a subject a therapeutically effective amount of a composition comprising the transgenic plant, or a portion thereof, in which expression of a FRD3 polypeptide is altered. In a preferred embodiment, the composition is administered in combination with a pharmaceutically acceptable carrier. In another preferred embodiment, the FRD3 polypeptide is overexpressed. Subjects who can be treated by the method of this invention include living organisms, e.g. mammals, e.g., humans. Examples of preferred subjects are those who have or are susceptible to iron-deficiency or zinc-deficiency, e.g., infants and women of childbearing age. As used herein, the phrase "a disorder associated with metal-deficiency" refers to any disease or disorder that results from a negative balance between metal intake and metal loss, e.g., iron intake and iron loss or zinc intake and zinc loss. For example, whenever there is rapid growth, as occurs during infancy, early childhood, adolescence and pregnancy, positive iron balance is difficult to maintain. Iron-deficiency can be the result of low dietary iron content, especially bioavailable iron, while in areas endemic for hookworm, intestinal blood loss secondary to heavy infestation contributes to iron-deficiency in both women and men. More severe forms of iron-deficiency usually result in anemia. In addition to iron, zinc is a metal with great nutritional importance, particularly during periods of rapid growth, due to its intervention in cellular replication as well as in development of the immune response. There is considerable evidence that zinc deficiency in humans is a serious worldwide problem and outweighs the potential problem of accidental, self-imposed, or environmental exposure to zinc excess. Acute deficiency (Henkin et al. (1975) *Arch Neurol* 322:745–751) and chronic deficiency (Prasad A. S. (1991) *Am J Clin Nutr* 53:403–412) are well-known entities in human populations and are probably much more common than generally recognized. The importance of zinc for human health was first documented in 1963 (Prasad et al. (1963) *J Lab Clin Med* 61:537–549). During the past 25 years, deficiency of zinc in humans due to nutritional factors and several disease states has now been documented throughout the world. Prevalence of zinc deficiency is high in populations that consume large quantities of cereal proteins containing high amounts of phytate, an organic phosphate compound. Alcoholism, malabsorption, sickle cell anemia, chronic renal disease, and other chronically debilitating diseases are known to be predisposing factors for zinc deficiency in humans (Prasad A S, (Prasad, A S, ed.) (1988) *New York: Alan R. Liss* 3–53; Hambridge M. (2000) J. Nutr. 130: 1344S–1349S).

Based upon clinical data and using traditional, epidemiologic techniques, Henkin and Aamodt (Henkin R I, Aamodt R L, (Inglett G E, ed.) (1983) *Washington: American Chemical Society* 83–105) have reclassified zinc deficiency into three syndromes; these are (a) acute, (b) chronic, and (c) subacute zinc deficiency. Acute zinc deficiency is relatively uncommon and follows parenteral hyperalimentation or oral L-histidine administration. Chronic zinc deficiency is more common, usually resulting from chronic dietary lack of zinc. Subacute or latent zinc deficiency is the most common of these syndromes. It is estimated that there are 4 million people in the United States with this syndrome, the initial symptom being dysfunction of taste and olfaction; treatment with exogenous zinc restores taste and smell but this usually requires months before these functions are returned to normal (Henkin et al. (1976) *Am J Med Sci* 272:285–299). Diagnosis of these disorders is most efficacious following oral administration of zinc tracers such as $^{65}$Zn, $^{67}$Zn, or $^{70}$Zn with subsequent evaluation of the kinetics of transfer of the isotope into various body tissues, the formulation of the data by compartmental analysis, and the integration of the data by a systematic model of zinc metabolism.

Clinical symptoms of human zinc-deficiency states exhibit a spectrum ranging from mild to severe and may even be fatal if unrecognized and not corrected (Prasad, A S (Prasad, A S, ed.) (1988) *New York: Alan R. Liss,* 3–53). The clinical manifestations of severely zinc deficient subjects include bullous pustular dermatitis, diarrhea, alopecia, mental disturbances, and intercurrent infections due to cell-mediated immune disorders. These severe signs are seen in patients with acrodermatitis enteropathica secondary to an inborn error of zinc absorption, patients receiving total parenteral nutrition without zinc, and patients receiving penicillamine therapy. Growth retardation, male hypogonadism, skin changes, poor appetite, mental lethargy, abnormal dark adaptation, and delayed wound healing are usual manifestations of moderate deficiency of zinc. Recent studies show that a mild or marginal deficiency of zinc in humans is characterized by neurosensory changes, oligospermia in males, decreased serum testosterone in males, hyperammonemia, decreased serum thymulin activity, decreased IL-2 production, decreased natural killer cell activity, alterations in T cell subpopulations (Prasad, AS (Prasad, AS, ed.) (1988) *New York: Alan R. Liss,* 3–53), impaired neuropsychological functions (Penland, J. G. (1976) *FASEB, J* 5:A938), and decreased ethanol clearance (Milne et al. (1991) *Am J Clin Nutr* 53:25).

It has also been shown that DNA damage from micronutrient deficiencies are a likely major cause of cancer (Ames, B. (2001) Mutation Res. 475: 7–20). Accordingly, compositions of the present invention are useful in treating and preventing cancer.

The compositions of the invention can be administered to the subject by a route of administration which allows the composition to perform its intended function. Various routes of administration are described herein in the section entitled "Pharmaceutical Compositions". Administration of a therapeutically active or therapeutically effective amount of the composition of the present invention is defined as an amount effective, at dosages and for periods of time, necessary to achieve the desired result.

Other aspects of the invention pertain to methods for evaluating a candidate compound for the ability to interact with, e.g., bind, a FRD3 polypeptide. These methods include contacting the candidate compound with the FRD3 polypeptide and evaluating the ability of the candidate compound to interact with, e.g., to bind or form a complex with the FRD3polypeptide. These methods can be performed in vitro, e.g., in a cell free system, or in vivo, e.g., in a two-hybrid interaction trap assay. These methods can be used to identify naturally occurring molecules which interact with FRD3 polypeptides. They can also be used to find natural or synthetic inhibitors of FRD3 polypeptides.

Yet other aspects of the invention pertain to methods for identifying agents which modulate, e.g., inhibit or activate/ stimulate, a FRD3 polypeptide or expression thereof. Also contemplated by the invention are the agents which modulate, e.g., inhibit or activate/stimulate FRD3 polypeptides or FRD3 polypeptide expression and which are identified according to methods of the present invention. In one embodiment, these methods include contacting a first polypeptide, e.g., a naturally occurring ligand of FRD3, with a second polypeptide comprising a FRD3 polypeptide and an agent to be tested and determining binding of the second polypeptide to the first polypeptide. Inhibition of binding of the first polypeptide to the second polypeptide indicates that the agent is an inhibitor of a FRD3 polypeptide. Activation of binding of the first polypeptide to the second polypeptide indicates that the agent is an activator/stimulator of a FRD3 polypeptide.

This invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Methods and Materials

*Arabidopsis* lines and growth conditions: The *Arabidopsis* (*Arabidopsis thaliana*) mutants frd3-1, frd3-2 and the corresponding Columbia gl-1 wild type have been described previously (Yi (1995) *Iron uptake in Arabidopsis thaliana,* Ph.D., Dartmouth College, Hanover, N.H.). man1 was obtained from the *Arabidopsis* Biological Resource Center (see the website at biosci.ohio-state.edu/~plantbio/Facilities/abrc/abrchome.htm). Unless otherwise specified, plants were grown under sterile conditions as described previously (Yi and Guerinot (1996) Plant J. 10:835–844). Briefly, seeds were sown on Petri plates containing Gamborg's B5 media (Sigma) and grown until the 4 to 6 true leaf stage and then transferred to plates with or without 50 μM Fe(III) EDTA for iron-sufficient or deficient conditions, respectively, for three days prior to analysis. Both Fe(III) chelate reductase assays and the pH plates were also described previously (Yi and Guerinot (1996)).

RNA blot hybridization: RNA isolation, RNA blotting and all molecular biology procedures were performed using standard protocols (Ausubel et al. (2001) Current Protocols in Molecular Biology. (New York, N.Y.: John Wiley & Sons)). RNA blots (5 μg total RNA per lane) were visualized either by exposure to film for one to two days or to a Molecular Dynamics Typhoon PhosphoImager screen for 4 to 24 hours. FRO2 and IRT1 probes were made from previously published cDNA clones (Eide et al. (1996) Natl. Acad. Sci. USA 93:5624–5628; Robinson et al. (1999) Nature 397:694–697) and a UBQ5 PCR product was amplified as described (Rogers and Ausubel (1997) Plant Cell 9:305–316). Probe DNA containing approximately 30 μC $^{32}$P was used for each blot.

Immunoblots: Immunoblots were performed as previously described (Connolly et al. (2002) Plant Cell in press). Total protein was prepared from the roots and shoots of plants grown axenically on plates that were either iron-deficient or iron-sufficient. Extracts were prepared by grinding tissue (2 ml buffer per 1 g wet tissue) on ice in extraction buffer (50 mM Tris pH 8.0, 5% glycerol, 4% SDS, 1% polyvinyl-polypyrrolidone, 1 mM PMSF), followed by centrifugation at 4° C. for fifteen minutes at 14,000×g. The supernatant was recovered and total protein was estimated using the BCA protein assay (Pierce, Rockford, Ill.). Samples for SDS-PAGE were diluted with an equal volume of 2× sample prep buffer (Ausubel et al. (2001) Current Protocols in Molecular Biology. (New York, N.Y.: John Wiley & Sons)) and boiled for two minutes. Total protein (10 µg) was separated by SDS-PAGE (Laemmli (1970) Nature 227:680–685) and transferred to polyvinylidene fluoride membrane by electroblotting (Towbin et al. (1979) Proc. Natl. Acad. Sci. USA 76:4350–4354). Membranes were blocked in 1×PBST (0.1% Tween 20 in 1×PBS) with 5% nonfat dry milk for 3 hr at 37° C. and then washed 2 times in 1×PBST for 5 min each. The membranes were then incubated overnight at 4° C. with an anti-IRT1 antibody (1:1,000 fold dilution in 1×PBST, 1% nonfat dry milk). The IRT1 antibody was raised and affinity purified against a synthetic peptide (PANDVTLPIKEDDSSN (SEQ ID NO: 11)) that corresponds to amino acids 162 to 177 of the IRT1 deduced protein sequence and is unique to IRT1 (Quality Controlled Biochemicals, Inc.). Next, the membranes were washed in 1×PBST, 4 times for 15 min each. Membranes were then incubated for 1 hour with goat-anti-rabbit IgG conjugated to Horseradish peroxidase (HRP) (1:5000 dilution in 1×PBST, 1% nonfat dry milk) (Pierce) followed by 4 washes for 15 min each in 1×PBST. Chemiluminescence was performed using the Renaissance Western Blot Chemiluminescence Reagent according to the directions of the manufacturer (NEN Life Science Products).

Elemental Analysis: Approximately 200 plants grown under iron-sufficient or iron-deficient conditions were pooled and subjected to elemental analysis. Metal content of the tissue was determined by the Dartmouth Superfund Trace Metal Core Facility by use of a magnetic sector-inductively coupled plasma-mass spectrometer (ICP-MS ELEMENT, Finnigan MAT) as previously described (Chen et al. (2000) Limnology and Oceanography 45:1525–1536.). All values obtained were within the linear sensitivity range for this instrument.

Detection of NA: Nicotianamine was extracted from Arabidopsis tissue as previously described (Pich et al. (2001) Planta 213:967–976). Briefly, samples were ground in liquid nitrogen, extracted in $H_2O$ at 80° C., centrifuged and the supernatant was dried by lyophilization. Extracts were redissolved in $H_2O$ and spotted on TLC plates, which were developed in butanol:acetic acid:$H_2O$ (4:1:1) (Shojima et al. (1989) Plant Cell Physiol. 30:673–677). NA was visualized after reaction with nihydrin. Samples were co-chromatographed with chemically synthesized NA (the kind gift of Dr. Axel Pich, Oldenburg, Germany) for identification purposes.

frd3 Mapping and Complementation: CAPS, SSLP (simple sequence length polymorphism), and RFLP (restriction fragment length polymorphism) markers, publicly available on the *Arabidopsis* Information Resource (TAIR) web page at arabidopsis.org, were used where possible to obtain a rough map position of frd3. AtMLP3, F6, and F7, are SSLP markers constructed around simple sequence repeats in the corresponding BAC sequence. F9 is an RFLP marker identified experimentally. The polymorphism covered by F11 is from the Cereon *Arabidopsis* Polymorphism Collection (available on the TAIR web site) and was scored by sequencing PCR products of that region. The complementing clone was constructed by digesting BAC T8G24 and ligating the total digest into the binary vector pCambia2300, available on the internet at the website of cambia.org.au according to standard molecular biology procedures (Ausubel et al. (2001)). The resulting clones were screened by PCR for the construct of interest. The complementing clone was introduced into thefrd3-1 mutant by *Agrobacterium*-mediated transformation (Clough and Bent (1998) Plant J. 16:735–743). 5'RACE was performed according to the instruction manual for the 5'RACE System for Rapid Amplification of cDNA Ends, Version 2.0 (Life Technologies).

DNA and Protein Sequence Analysis: DNA sequencing was performed at the Dartmouth Molecular Biology Core Facility on an ABI Prism 3100 Automated DNA Sequencer. Sequence was analyzed with the GCG (Genetics Computer Group) software package and by BLAST available on the internet at the website of ncbi.nlm.nih.gov. Multiple sequence alignments were performed using the BCM Search Launcher available on the internet at the website of dot.imgen.bcm.tmc.edu:9331/multi-align/multi-align. These alignments were transformed into dendograms using MEGA version 2.1 available on the internet at the website of megasoftware.net or colored using BoxShade available on the internet at the website of embnet.org.

Example 1

Cloning of FRD3

An *Arabidopsis* mutant that constitutively expresses all three strategy I iron deficiency responses was identified. The frd3 gene was mapped to a 55 kb interval on Chromosome III. The gene was identified by sequencing genomic DNA coding for candidate genes in this 55 kb interval from all three mutant alleles, frd3-1, frd3-2, and man1 (renamed frd3-3). This sequence was compared to the publicly available genomic sequence. The identified open reading frame has different single base pair alterations in each of the three alleles. frd3-1 has a C to A nucleotide change that yields an alanine to aspartic acid change in the protein. frd3-2 has a single nucleotide deletion in the coding sequence which results in a frameshift and the addition of nine novel amino acids followed by a premature stop codon. man1 has a G to A change at the first nucleotide of an intron. This leads to the retention of the intron in the cDNA and in the corresponding protein, this leads to the addition of two novel amino acids followed by a premature stop codon. A description of the MAN1 mutant is included in Delhaize, E. (1996) *Plant Physiol*. 111:849–855, the contents of which are herein incorporated by reference.

The accession number for the BAC, T8G24, containing this open reading frame is AC074395. As currently annotated, frd3 is the second gene on this BAC. Its gene number is T8G24.8 and its protein ID is AAG50830.1. In the MIPS database, wild type FRD3 is At3g08040. There is one EST sequence for this gene, accession number AV546075. It consists of 376 base pairs from the 3' end of the cDNA. It was deposited by Kazusa and we obtained cDNA clone from them (clone number RZL08b02). The whole cDNA clone was sequenced, confirming the predicted splice sites and protein sequence. A RT-PCR product was also sequences for man1 around the site of the mutation in man1.

Example 2

Characterization of Wild Type FRD3 and Mutant FRD3

FRD3 proteins can be characterized with respect to their patterns of expression and localization. Based on previous RT-PCR experiments, FRD3 is expressed in *Arabipopsis* roots but not in shoots. FRD3 is present in the roots under both iron-sufficient and iron-deficient conditions. In situ hybridization techniques and a GUS translational fusion reporter gene construct can be used to determine when and where FRD3 is expressed, e.g., in which particular cell types. Immunolocalization can be used to determine the subcellular location of FRD3, either with antibodies to an epitope-tagged version of FRD3 or with antibodies to FRD3 itself. FRD3 can also be overexpressed in a wild type *Arabidopsis* plant to determine if it confers phenotypes of interest.

Figure 8A:
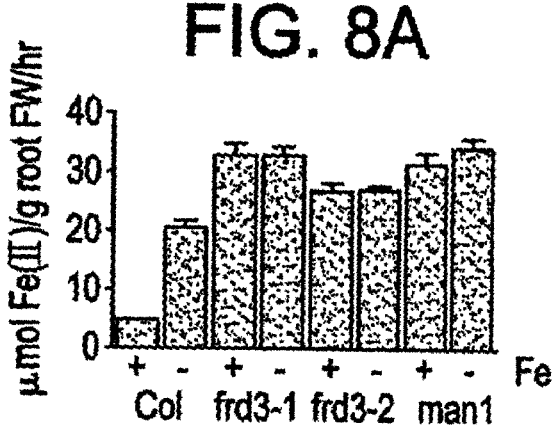
FIG. 8 includes are graphs (A) and (B) showing ferric chelate reductase activity. (A) frd3 and man1 exhibit constitutive Fe(III) chelate reductase activity. Plants grown with or without Fe(III) EDTA for three days were assayed for Fe(III) chelate reductase activity. (B) frd3 and man1 are recessive and allelic. All plants were grown with Fe(III) EDTA for three days. For both panels, values are the mean of nine (9) plants and standard errors are shown. Experiments were performed at least twice and representative data sets are shown.

It is also possible to characterize the biochemical function of FRD3. For example, FRD3 can be expressed in yeast (*Saccharomyces cerevisiae*) to test the FRD3 iron-binding or iron-transporting properties. FRD3 could bind or transport iron either alone or as iron complexed to a low molecular weight chelator, e.g., nicotianamine, a non-protein amino acid and iron chelator that has been shown in other plants to be involved in iron homeostasis.

man1 is allelic to frd3: A comparison of wild type, frd3-1, frd3-2, and man1 Fe(III) chelate reductase activities in both iron-sufficient and iron-deficient plants is shown in FIG. 8A. In wild type (ecotype Columbia), Fe(III) chelate reductase activity is induced approximately 4-fold by iron deficiency. However, in all three of the mutants, Fe(III) chelate reductase activity is equivalent under iron-sufficient and iron-deficient growth conditions. In addition, cupric (Cu(II)) reductase activity is upregulated in the mutants (data not shown). The *Arabidopsis* frd1 mutant lacks both Fe(III) chelate reductase activity and Cu(II) reductase activity (Yi and Guerinot (1996) Plant J. 10:835–844). Both reductase activities are restored by the addition of a wild-type FRO2 gene (Robinson et al. (1999) Nature 397:694–697). Therefore, the Cu(II) reductase activity, as well as Fe(III) chelate reductase activity is attributed to the FRO2 protein.

Figure 8B:
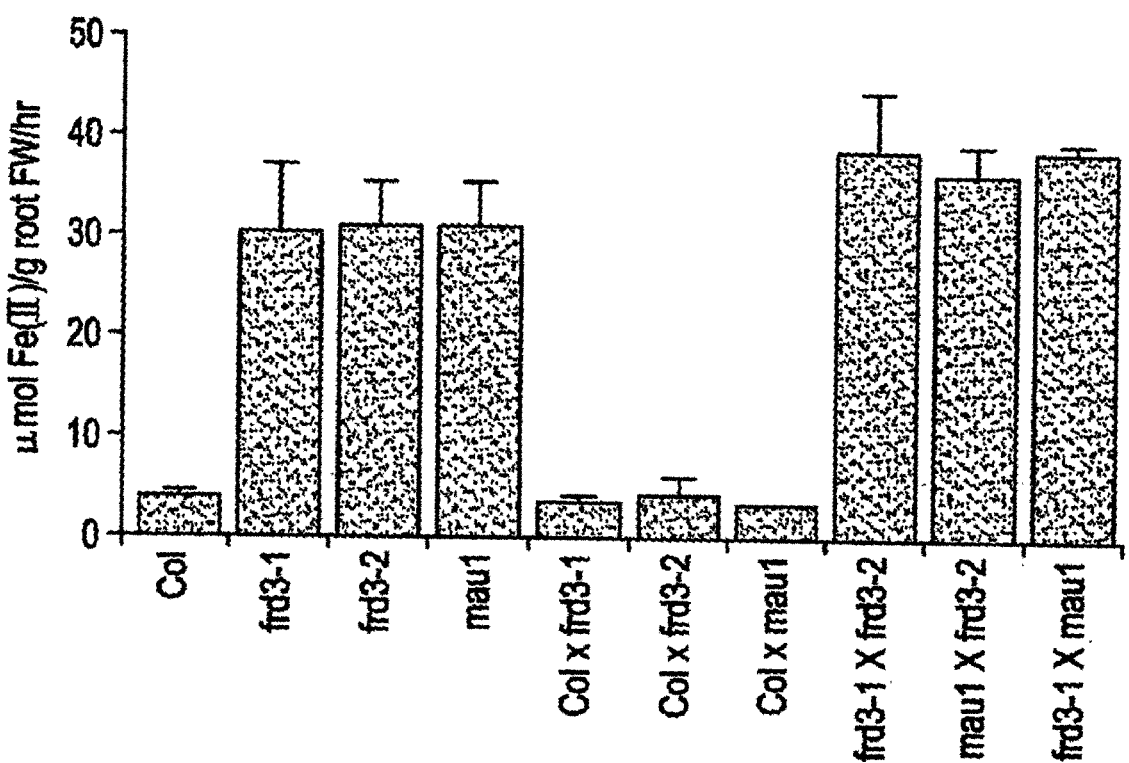

FIG. 8B shows Fe(III) chelate reductase activity of F1 progeny of the mutants crossed to the wild-type parent, and to each other. These plants were grown under iron-sufficient conditions to emphasize the mutant phenotype. F1 progeny from wild type crossed to each of the mutants show low, wild type levels of Fe(III) chelate reductase activity, demonstrating that all three of the mutations are recessive; in fact, all three segregate as single recessive Mendelian loci (data not shown). F1 progeny from mutant to mutant crosses all show high levels of reductase activity (FIG. 8B) comparable to the parental phenotype. This indicates that none of the three complement each other and are all alleles of the same locus. Therefore, man1 has been renamed frd3-3.

In order to further investigate the Fe(III) chelate reductase activity, the expression of the FRO2 Fe(III) chelate reductase gene was examined by RNA blot hybridization. Unlike the situation in wild type plants, FRO2 is expressed constitutively in the roots of mutants carrying any frd3, i.e., any of the three alleles of frd3 (data not shown). This is to be expected, because FRO2 is the gene responsible for the iron deficiency induced root Fe(III) chelate reductase activity (Robinson et al. (1999), an activity that is constitutively present in frd3, the frd3 mutant.

frd3 constitutively expresses all three Strategy I responses: To test if frd3 constitutively expressed another Strategy I iron deficiency response, Fe(II) transport, the expression of the iron-regulated transporter IRT1 was examined. The expression of IRT1 parallels the expression of FRO2, with expression in the roots of frd3 plants under both iron-sufficient and deficient conditions (data not shown). The IRT1 protein has been shown to be subject to post-transcriptional regulation (Connolly et al. (2002) Plant Cell in press) so it cannot be assumed that elevated mRNA levels correspond to elevated levels of IRT1 protein. Therefore, IRT1 protein levels were assayed by immunoblot (data not shown); the IRT1 protein does accumulate in iron-sufficient roots of the frd3. Therefore, frd3 cannot sense iron levels and is responding in an iron-deficient manner under iron-sufficient growth conditions.

Because IRT1 was shown to transport iron, manganese and zinc when expressed in yeast (Eide et al (1996) Natl. Acad. Sci. USA 93:5624–5628; Korshunova et al. (1999) Plant Mol. Biol. 40:37–44) and is overexpressed in frd3, shoot metal levels in the frd3 were examined. As shown in FIG. 9, mutants carrying all three alleles of the wild type frd3 show 2–3× higher levels of iron, 2× higher levels of zinc and 3–4× higher levels of manganese in their shoots than the wild type. Copper levels were unchanged in the mutants (data not shown). frd3-3 (man1) has previously been shown to have higher levels of zinc and manganese but not iron in its shoots (Delhaize (1996)). This difference might be accounted for by the different levels of iron in the media used in the two works. In this study, plants were grown on 100 µM ferrous sulfate while in the work of Delhaize, 20 µM Fe(III)EDDHA was used. In this study, iron levels of soil grown plants were similar in the wild type and frd3 (data not shown), in agreement with results previously reported for soil grown man1/frd3-3 plants (Delhaize (1996)). Recently, seeds produced by man1 mutant plants were shown to have metal levels similar to seeds from wild type plants (Lott and West (2001) Can. J. Bot. 79:1292–1296); this is in agreement with the results obtained here (data not shown).

It has been shown previously that levels of the iron chelator nicotianamine (NA) parallel iron levels in plant tissue (Pich et al. (2001) Planta 213:967–976). NA levels in the roots and the shoots of wild type and frd3-1 mutant plants grown under both iron sufficient and iron-deficient conditions were examined by TLC. All samples from frd3 plants contained at least 2-fold higher amounts of NA as compared to the corresponding sample from wild type plants (data not shown).

To show that frd3 plants constitutively efflux protons, plants were grown with or without Fe(III) EDTA for three days and then transferred to bromocresol purple plates for 18 hr. Iron-deficient wild type (ecotype Columbia) and iron-sufficient and deficient frd3-1 reduce the pH of the medium below 5.2 (data not shown). Iron-sufficient wild type causes the pH to rise above 7.0. Accordingly, based on pH indicator plates, frd3-1 acidifies the media surrounding its roots when grown both under iron-sufficient and deficient conditions. In contrast, wild type only acidifies the surrounding media after being grown under iron-deficient conditions. Therefore, frd3 plants constitutively efflux protons which is another Strategy I iron deficiency response. Thus, frd3 plants constitutively express the three known Strategy I iron deficiency responses.

Cloning of wild type frd3 by a map-based approach: To identify the molecular basis of the frd3 phenotype, frd3-1 was crossed to Landsberg-erecta (Ler) and mapped using CAPS (cleaved amplified polymorphic sequence) markers (Konieczny and Ausubel (1993) Plant J. 4:403–410). frd3 mapped to the top of Chromosome 3, in agreement with published mapping data for man1 (Delhaize (1996)). Approximately 820 homozygous mutant F2 progeny from the inter-ecotype cross were examined to refine the map position to a 55 kb interval as shown in FIG. 10A. This interval was completely covered by a single BAC, F 17A17 that was sequenced as part of the *Arabidopsis* Genome Initiative (AGI). Predicted open reading frames in this region were sequenced from one or more of the frd3 alleles, looking for differences between the mutant and wild type sequences. Non-synonymous single base-pair alterations were found in all three alleles in one ORF in this region.

Expression of wild type genomic DNA containing only this ORF (marked by the striped box in FIG. 10A) in frd3-1 complements the chlorotic phenotype and restores the iron deficiency inducible Fe(III) chelate reductase activity (FIG. 10B). Thereby identifying the gene containing the mutations responsible for the frd3 phenotypes. Wild type frd3 encodes an integral membrane protein 526 amino acids long. The computer topology prediction program HMMTOP (Tusnady and Simon (2001) J. Mol. Biol. 283:489–506) predicts 12 transmembrane domains, as diagrammed in FIG. 10C, with the N- and C-termini internal. Wild type FRD3 is predicted to localize to the plasma membrane according to PSORT (Nakai and Kanehisa (1992) Genomics 14:897–911) and TargetP (Emanuelsson et al. (2000) J. Mol. Biol. 300: 1005–1016).

The wild type frd3 gene corresponds to an EST sequence and the cDNA clone was obtained from the Kazusa DNA Research Institute and completely sequenced. The cDNA sequence has been deposited in Genbank (accession number AF448231). A string of As at the 3' end of the sequence and 5' RACE (rapid amplification of cDNA ends) confirmed that this clone was full length; the transcriptional start site is 117 bp upstream of the ATG. The cDNA sequence is consistent with the protein sequence predicted by AGI. Comparison of the wild type frd3 genomic and cDNA sequences revealed that the wild type frd3 gene has 13 exons and 12 introns, as diagrammed in FIG. 10D. It is notable that the first intron is in the 5' untranslated region and is almost 2.6 kb in length; this is much larger than the approximately 170 bp average for *Arabidopsis* introns (*Arabidopsis* Genome Initiative (2000) Nature 408:796–815). Long introns in other *Arabidopsis* genes have been shown to play important roles in the regulation of gene expression (Jeon et al. (2000) Plant Physiol. 123:1005–1014).

FIG. 10D also indicates the single nucleotide sequence changes in the three frd3 mutant alleles. frd3-1 has a C to A transversion. In the protein, this causes an aspartic acid to substitute for an alanine residue at position 54 in the first transmembrane domain (see FIG. 10C). frd3-2 has a deletion of a single G in the eighth exon, causing a frame shift and the addition of seven novel amino acids followed by a premature stop codon; frd3-2 codes for approximately two-thirds of the wild type protein. frd3-3 has a G to A transition in the first nucleotide of the fifth intron. Because this G is part of the required GT in a splice donor site, such a change would be predicted to lead to the retention of the intron. Sequence data from a frd3-3 RT-PCR product confirms that this intron is retained (data not shown). This shifts the reading frame at a point approximately half way through the protein, leading to the addition of two novel amino acids followed by a premature stop codon.

frd3 Expression: The expression of wild type frd3 and frd3 in the roots is shown in FIG. 11. No expression was detected in the shoots of wild type or any of the mutant alleles either by RNA blot hybridization or by RT-PCR (data not shown). In wild type, wild type frd3 is expressed both under iron-sufficient and deficient conditions. After normalization to the control gene UBQ5, wild type frd3 mRNA levels are approximately 2-fold higher under iron deficiency. mRNA levels are considerably higher in plants carrying frd3 than in wild type and higher when plants are grown under iron-sufficient conditions rather than iron-deficient conditions. The difference in wild type frd3 mRNA levels under iron sufficiency varies from approximately 10-fold higher than wild type in frd3-2 to almost 100-fold higher in frd3-3. Accordingly, wild type frd3 is itself regulated by the process it controls. Because the wild type FRD3 is an integral membrane protein, this is an indirect effect.

Wild Type frd3 and frd3 are Members of the MATE Gene Family: Wild type FRD3 and FRD3 are members of the MATE (multi-drug and toxin efflux) family, an extensive group of membrane proteins involved in a variety of processes by functioning as a transporter of small organic molecules. In addition to *Arabidopsis*, there are MATE family members in humans, the yeasts *Saccharomyces cerevisiae* and *Schizosaccharomyces pombe*, *Escherichia coli* and other bacteria, and archaea. *Arabidopsis* has 56 MATE family members, which is 10 times more than any other sequenced organism (*Arabidopsis* Genome Initiative (2000)). FIG. 12 shows a dendogram which includes all 56 *Arabidopsis* proteins, one human protein, five proteins from yeast and selected bacterial members. The *Arabidopsis* genes fall into two main groups. The top group in FIG. 12 contains 50 *Arabidopsis* members and is loosely associated with the yeast and human family members. The other smaller group contains FRD3 and the bacterial NorM and DinF proteins.

FIG. 13 shows an alignment of nine MATE proteins: five from *Arabidopsis;* the yeast protein ERC1; and three bacterial family members. These nine proteins share sequence homology along their entire lengths except for the very N-terminal portion. As would be expected, the transmembrane domains are the most conserved. FRD3 is 57.8% identical to another *Arabidopsis* protein, FRD3-like or FRDL. FRD3 and FRDL are unique among the MATE family members shown in FIG. 13 in possessing a larger cytoplasmic loop between transmembrane domains II and III.

Equivalents Those skilled in the art will recognize, or be able to ascertain using no more than routine experimentation, many equivalents to the specific embodiments of the invention described herein. Such equivalents are intended to be encompassed by the following claims.

What is claimed:

1. An isolated ferric reductase defective (FRD3) polypeptide comprising the amino acid sequence selected from the group consisting of the amino acid sequence set forth in SEQ ID NO:3, 6, and 9.

2. A transgenic plant comprising an isolated FRD3 polypeptide, wherein the FRD3 polypeptide comprises the amino acid sequence selected from the group consisting of the amino acid sequence set forth in SEQ ID NO:3, 6, and 9.

3. The transgenic plant of claim 2, wherein the plant is selected from the group consisting of maize, wheat, rye, sorghum, cassava, beans, rice, beans, and peas.

4. A method for modulating metal concentration in a medium containing the metal, comprising:

(a) providing the transgenic plant of claim 2; and
(b) contacting the transgenic plant with the medium, such that the metal concentration in the medium is modulated.

5. A method for removing a pollutant from soil, comprising contacting the transgenic plant of claim 2 with the soil such that the pollutant is removed from the soil.

6. The method of claim 5, wherein the pollutant is a metal.

7. The method of claim 6, wherein the metal is selected from the group consisting of As, Pb, Co, Cd, Hg, Zn, and Cu.

8. A method for promoting plant growth, comprising introducing into a plant the isolated FRD3 polypeptide of claim 1.

* * * * *

SEQUENCE LISTING

```
<160> NUMBER OF SEQ ID NOS: 20

<210> SEQ ID NO 1
<211> LENGTH: 5738
<212> TYPE: DNA
<213> ORGANISM: Arabidopsis thaliana
```

<400> SEQUENCE: 1

| | | | | | |
|---|---|---|---|---|---|
| tttctacata | ttttgattc | cattttcata | agaaaatctt | cagtatatta | ttacattcat | 60 |
| atttattact | tctttattat | ttaaagtgat | cattccaatt | ttatatatag | aaaattattt | 120 |
| atttatttat | ggcaaggttg | caacatataa | aaaaaagtt | ggtatacaaa | caaatatcta | 180 |
| aaataatccc | ctctaaactc | tcctagatac | tcactcatca | ctactcatct | caagttcacg | 240 |
| tgactactta | tataagcgtt | gactacataa | aggtaagata | ttctctccac | atatctcata | 300 |
| agttctatga | tttttcttag | tattgcatat | atgttctcta | tcctactagg | atatatcaac | 360 |
| acaacataca | caagttctca | attgaattag | aagctcatga | gtaactataa | ctgtatatat | 420 |
| agttaactag | attacgagta | agaatgcaat | tgtaaagcct | tttaattgaa | cttcttcttc | 480 |
| ttttttttgat | aaaaggtttt | taattaaaaa | aacaagtaat | taaccattac | aagctaggac | 540 |
| aactaagtca | tacatgttga | gagtagtgag | agagttaagc | aaaagcttaa | tctagtcctt | 600 |
| ttaaaagcta | acaaacatag | tagagattat | aagatgtttg | gtgtaaataa | caacaatacc | 660 |
| cagtttgtac | atgtgtttag | aaaatagttt | ggattatggt | ctaaaatata | taaattataa | 720 |
| gaaagatgat | gtctaacgat | tcaacatagc | aaaagatgat | gtacacaaat | gtttttgttt | 780 |
| tacccatgta | aaaaaacaga | acattagttg | ttaagtttat | aggtttatt | tctacattaa | 840 |
| ttttcacaac | ttttagtac | cagaacgcac | aatcaattaa | gttttcatct | tctatatata | 900 |
| ctgatctaaa | aatattaata | taaggtttgg | gataattcaa | tttaatcaca | tcgtttataa | 960 |
| aaagcggtta | actctacgat | aactaaataa | attgtgttat | atgaaaaggg | gaagtggcaa | 1020 |
| tgtaggtaat | ggaattgacg | ttgatggctt | gaaaagatg | gccttatctt | gcggaacaaa | 1080 |
| caattacata | cacgacacgc | actatataca | actcacctgt | gttggtctct | gttgccatct | 1140 |
| tttatgttat | tgttttccga | ctgtcgcctt | cctttaacta | atattataat | tttaaagatg | 1200 |
| ttcataaatc | acagtagaaa | gcttgttttt | gctaaaatga | acatgacacg | gatcatacaa | 1260 |
| aaaatatatt | ttacactata | gctatatacc | gatttaatct | taggtacttt | gaatcgtgct | 1320 |
| aaaactaaac | ggccttctca | aaaccctccc | tcttttcctc | cctccctcag | aaaccccctcc | 1380 |
| atcgacaaat | aacgttatgc | aattctctaa | acaatgctcg | acaagcatgt | gttttagta | 1440 |
| atgctacaac | ttatttctct | tttcaacgtc | ctaagaggca | tcaaaaagat | caagatcttt | 1500 |
| ggaaccgagg | tcctatgcaa | ggaatcatta | taaagtacca | tgttatttt | ttaaataaca | 1560 |
| tcgtttctt | aatataattt | ataaataccg | ttatttttac | cgaaatttca | tatatatgtc | 1620 |
| agttttatac | tttgtacgat | aacgccaaaa | actttaatta | tcgccaaaat | tgtaaacggt | 1680 |
| attttcgtcg | tttagttatt | taccaaaaat | aaaatgacga | ttgcaactta | tttagttaaa | 1740 |
| atacaaaaaa | aaactaatat | attaattgag | cggacggaat | ttttttccaa | atcccgatg | 1800 |
| tgtaaatatg | agaacgtttc | gaggataact | tacaaattaa | acattaataa | aaatgataaa | 1860 |
| gtgtagttag | gagctaaatt | gtgatagtaa | acatctatct | ctaatattat | taaatgaatt | 1920 |
| ataatactat | tttaatcata | gtattaaatt | tctttaatta | aaaatataaa | taatttcaat | 1980 |
| ttaattctat | accaaattaa | cccgaaaata | ttttatctaa | catacacaaa | gacacataaa | 2040 |
| agttttgata | actgcctaaa | aaataagct | tttgaattat | taattagttg | ttattcaatg | 2100 |
| ataaaataac | attatttgtc | aactagtgaa | ttccaattac | gcaaaatgat | tcacttttt | 2160 |
| agtggaaaat | atcaaagaaa | aatgagaagt | ttatatgaaa | ataaactctt | tcccactatg | 2220 |
| atgaatacat | gtaagaaaac | tttcatgaaa | agaaaactta | tttactcaat | ataaaaatag | 2280 |

```
aagactcttt atctttcacg agtaaaagtt cacgaaaacc atattttcct attgattaaa    2340
gaaatcatag aagttaaaat aatcaacaag ggcaagccaa aaacttctag tgtgggattt    2400
acttaataga agtatatata ttacgatgtt tatgcgtacc tattttccct caatgagaag    2460
agaaattcca taatattggt gtcttaagtt tggacgaaaa taaagagcag caaaaaagtt    2520
agggaaggaa acctttgttt tcttcaataa ttatagaaaa taatttcttt tattgattta    2580
gatattaaat aagcaaagat atgcatgctc attacgtgtc tataaataaa aacacgtttg    2640
tacatagcat ctactataaa cgttcctttt gcttccccga ttcttcgaaa cacttattga    2700
tatcttcaga cacaacaaat taattacaga gacagttaca gaggaaaaag atctatgacg    2760
gaaactggtg atgatcttgc tacggtgaag aagccaatcc catttctcgt tatcttcaaa    2820
gatttaaggt gtgtgtttat gtattcatga aatggtgatg aaattttttga aagaagtgat    2880 gcataacatt agtttattta tgtaaaattg cagacatgta ttcagtaggg acacaactgg    2940
gcgagagatt ctaggcatcg cgtttccagc agctttggct ttagctgctg atccaatcga    3000
ttctctgatt gataccgctt ttgtcgggcg tttaggagcg gttcagctag cggcggttgg    3060
agtttccatt gccatattca atcaagcttc tagaattacg atattcccac ttgtgagcct    3120
cacaacttca tttgtggcag aggaagacac gatggagaag atgaaagaag aagcaaacaa    3180
agccaatctt gttcatgcag aaactatact tgttcaagat tctttggaaa agggcatttc    3240
ttcacctaca agtaacgata ccaaccagcc acagcaacct ccaggtaaat tccgcatatc    3300
tcactcgaca ttgataactt ttattaaagt ttcgattgtt tttttactgt tggtttcttc    3360
tctcgatctc ttttgtttca atttgttgtt tttttggttg tattaaactt agctccggat    3420
acaaagtcaa atagcggaaa caaatcgaat aaaaaggaga agaggaccat tagaacagca    3480
tcaacagcta tgatcttggg gttaatcctt ggccttgtgc aagctatttt cttgattttc    3540
agttcaaagt tgcttctagg cgtcatggga gtgaaaccag taagttttca gaaatataca    3600
tattttgttg ggatctatag cataaaatgt tttgactaat ttgagttgaa tttggataac    3660
agaattcacc aatgttatca ccagcacaca agtacttgag catacgagct ttgggggctc    3720
ctgcattgct tctatctctt gctatgcaag gcatctttcg tggattcaag gacaccaaaa    3780
ctcctctctt tgccactggt aattaagttg ttaacttaga tcatctttaa tgatcactct    3840
ccttacttct tataatattt tgccttaatg cgtgaaacag tcgtagcaga tgttatcaac    3900
atagttctcg accccatctt cattttttgtg cttcgtctag ggatcatcgg tgcagccatt    3960
gcccatgtca tttctcagta agagaaatca ctaaaaaaat tccacacatg caaaagtgat    4020
cattattgaa caaaatcgct aggcgcactc ttgttttttct acagctataa atagacttgt    4080
gaagtcataa cctcaaacaa aaacaaatga tttgtttgtg tacgtgaagg tacttcatga    4140
ctctaatatt gttcgtcttc ctcgcaaaga aagttaattt gattccacca aacttcgggg    4200
atttgcagtt tggaaggttc cttaaaaatg gtacgtatgg atgcatattt attaaaagtt    4260
gtggttcttg caataatatt tttttttaaa aacaagatcc gtcgtaggag ctaatgcaca    4320
gagtccaaaa ataaattaac aaaaaattta tctatataat aatagaattc aatcaaataa    4380
ggtctatatt taaatattg aatattttga aatatatagt taagaaaatg agaaatgtgg    4440
atatatgtct aacaagtata gtattaaaaa tgaagggct actattgctg gcgaggacca    4500
tagcagtgac gttttgtcag accttagcag cagcaatggc ggcgcggctg gtacaacac    4560 caatggctgc ttttcagatt tgtttacaag tatggttaac ttcttctctt ctcaatgatg    4620
gtcttgccgt tgctggtcag gtaatcatgt tttctcgttg tattaatta tgtatagttt    4680
```

-continued

```
atatggttga tcaagttgta tgtagaaaat gatcattcaa tacgttgcag gcgattctgg    4740
cttgttcgtt tgctgagaag gactataaca aagtgactgc tgttgcatcc cgtgttctac    4800
aggttcggtc caaaaatcac attaccaaac ctttctttaa aaataaaata attgtgtaac    4860
taaaacagaa atgaatttga tacgcagatg ggttttgtgt taggacttgg actgtccgtt    4920
tttgttggac taggtctcta ctttggtgcc ggagttttct ccaaggaccc tgctgttatt    4980
cacctcatgg ccatcggaat accggtaact aataatcaaa taataattac tatagtataa    5040
aaatcatttt aaaagaattt tactaatgag aagaggttat atatatttat gcagtttata    5100
gcagcaacgc agccaataaa ctctctcgcc tttgtattgg atggagtcaa ttttggagca    5160
tctgattttg cttacactgc atactccatg gtatgcacac tatatatact atgaaatgat    5220
taaaattcct tttttttttt ttgaaatgac ttaaactttg tctatctttt tttcttgtaa    5280
tccaattatg ataaatcagg tgggagtggc ggccataagc attgcagcag taatatatat    5340
ggcaaagacc aatggtttca taggaatatg gatagctctt acaatctata tggctctccg    5400
ggctattact ggaattgcca ggtatttaaa ttgggccttt actatagccc actatagtag    5460
aagcagtatt tgactgagtg tttgaattta tgcaggatgc cgacaggaac tggaccgtgg    5520
aggttcttgc gtggacgatc atcctcttca tcttcctagg acttagttta tttataacga    5580
gttgcatctc ttcttccttc ttcgtttttg tttatggttc ttgtgtttgt ttttcaacat    5640
tttgttcgag agaccgttat catattatca gtttcacata ataatgcat attttttaagt    5700 cattaaaata tggagccctc tgccctcact ggcttttc                            5738
```

<210> SEQ ID NO 2
<211> LENGTH: 1868
<212> TYPE: DNA
<213> ORGANISM: Arabidopsis thaliana
<220> FEATURE:
<221> NAME/KEY: CDS
<222> LOCATION: (118)...(1695)

<400> SEQUENCE: 2

```
aaataatccc ctctaaactc tcctagatac tcactcatca ctactcatct caagttcacg     60
tgactactta tataagcgtt gactacataa agagacagtt acagaggaaa aagatct atg    120
                                                                  Met
                                                                   1 acg gaa act ggt gat gat ctt gct acg gtg aag aag cca atc cca ttt       168
Thr Glu Thr Gly Asp Asp Leu Ala Thr Val Lys Lys Pro Ile Pro Phe
        5                  10                  15 ctc gtt atc ttc aaa gat tta aga cat gta ttc agt agg gac aca act       216
Leu Val Ile Phe Lys Asp Leu Arg His Val Phe Ser Arg Asp Thr Thr
         20                  25                  30 ggg cga gag att cta ggc atc gcg ttt cca gca gct ttg gct tta gct       264
Gly Arg Glu Ile Leu Gly Ile Ala Phe Pro Ala Ala Leu Ala Leu Ala
 35                  40                  45 gct gat cca atc gat tct ctg att gat acc gct ttt gtc ggg cgt tta       312
Ala Asp Pro Ile Asp Ser Leu Ile Asp Thr Ala Phe Val Gly Arg Leu
 50                  55                  60                  65 gga gcg gtt cag cta gcg gcg gtt gga gtt tcc att gcc ata ttc aat       360
Gly Ala Val Gln Leu Ala Ala Val Gly Val Ser Ile Ala Ile Phe Asn
         70                  75                  80 caa gct tct aga att acg ata ttc cca ctt gtg agc ctc aca act tca       408
Gln Ala Ser Arg Ile Thr Ile Phe Pro Leu Val Ser Leu Thr Thr Ser
         85                  90                  95 ttt gtg gca gag gaa gac acg atg gag aag atg aaa gaa gaa gca aac       456
```

```
                Phe Val Ala Glu Glu Asp Thr Met Glu Lys Met Lys Glu Glu Ala Asn
                                100                 105                 110 aaa gcc aat ctt gtt cat gca gaa act ata ctt gtt caa gat tct ttg              504
Lys Ala Asn Leu Val His Ala Glu Thr Ile Leu Val Gln Asp Ser Leu
        115                 120                 125 gaa aag ggc att tct tca cct aca agt aac gat acc aac cag cca cag              552
Glu Lys Gly Ile Ser Ser Pro Thr Ser Asn Asp Thr Asn Gln Pro Gln
130                 135                 140                 145 caa cct cca gct ccg gat aca aag tca aat agc gga aac aaa tcg aat              600
Gln Pro Pro Ala Pro Asp Thr Lys Ser Asn Ser Gly Asn Lys Ser Asn
                150                 155                 160 aaa aag gag aag agg acc att aga aca gca tca aca gct atg atc ttg              648
Lys Lys Glu Lys Arg Thr Ile Arg Thr Ala Ser Thr Ala Met Ile Leu
        165                 170                 175 ggg tta atc ctt ggc ctt gtg caa gct att ttc ttg att ttc agt tca              696
Gly Leu Ile Leu Gly Leu Val Gln Ala Ile Phe Leu Ile Phe Ser Ser
180                 185                 190 aag ttg ctt cta ggc gtc atg gga gtg aaa cca aat tca cca atg tta              744
Lys Leu Leu Leu Gly Val Met Gly Val Lys Pro Asn Ser Pro Met Leu
        195                 200                 205 tca cca gca cac aag tac ttg agc ata cga gct ttg ggg gct cct gca              792
Ser Pro Ala His Lys Tyr Leu Ser Ile Arg Ala Leu Gly Ala Pro Ala
210                 215                 220                 225 ttg ctt cta tct ctt gct atg caa ggc atc ttt cgt gga ttc aag gac              840
Leu Leu Leu Ser Leu Ala Met Gln Gly Ile Phe Arg Gly Phe Lys Asp
                230                 235                 240 acc aaa act cct ctc ttt gcc act gtc gta gca gat gtt atc aac ata              888
Thr Lys Thr Pro Leu Phe Ala Thr Val Val Ala Asp Val Ile Asn Ile
        245                 250                 255 gtt ctc gac ccc atc ttc att ttt gtg ctt cgt cta ggg atc atc ggt              936
Val Leu Asp Pro Ile Phe Ile Phe Val Leu Arg Leu Gly Ile Ile Gly
260                 265                 270 gca gcc att gcc cat gtc att tct cag tac ttc atg act cta ata ttg              984
Ala Ala Ile Ala His Val Ile Ser Gln Tyr Phe Met Thr Leu Ile Leu
        275                 280                 285 ttc gtc ttc ctc gca aag aaa gtt aat ttg att cca cca aac ttc ggg             1032
Phe Val Phe Leu Ala Lys Lys Val Asn Leu Ile Pro Pro Asn Phe Gly
290                 295                 300                 305 gat ttg cag ttt gga agg ttc ctt aaa aat ggg cta cta ttg ctg gcg             1080
Asp Leu Gln Phe Gly Arg Phe Leu Lys Asn Gly Leu Leu Leu Leu Ala
                310                 315                 320 agg acc ata gca gtg acg ttt tgt cag acc tta gca gca gca atg gcg             1128
Arg Thr Ile Ala Val Thr Phe Cys Gln Thr Leu Ala Ala Ala Met Ala
        325                 330                 335 gcg cgg ctg ggt aca aca cca atg gct gct ttt cag att tgt tta caa             1176
Ala Arg Leu Gly Thr Thr Pro Met Ala Ala Phe Gln Ile Cys Leu Gln
                340                 345                 350 gta tgg tta act tct tct ctt ctc aat gat ggt ctt gcc gtt gct ggt             1224
Val Trp Leu Thr Ser Ser Leu Leu Asn Asp Gly Leu Ala Val Ala Gly
        355                 360                 365 cag gcg att ctg gct tgt tcg ttt gct gag aag gac tat aac aaa gtg             1272
Gln Ala Ile Leu Ala Cys Ser Phe Ala Glu Lys Asp Tyr Asn Lys Val
370                 375                 380                 385 act gct gtt gca tcc cgt gtt cta cag atg ggt ttt gtg tta gga ctt             1320
Thr Ala Val Ala Ser Arg Val Leu Gln Met Gly Phe Val Leu Gly Leu
                390                 395                 400 gga ctg tcc gtt ttt gtt gga cta ggt ctc tac ttt ggt gcc gga gtt             1368
Gly Leu Ser Val Phe Val Gly Leu Gly Leu Tyr Phe Gly Ala Gly Val
        405                 410                 415
```

```
ttc tcc aag gac cct gct gtt att cac ctc atg gcc atc gga ata ccg      1416
Phe Ser Lys Asp Pro Ala Val Ile His Leu Met Ala Ile Gly Ile Pro
        420                 425                 430 ttt ata gca gca acg cag cca ata aac tct ctc gcc ttt gta ttg gat      1464
Phe Ile Ala Ala Thr Gln Pro Ile Asn Ser Leu Ala Phe Val Leu Asp
435                 440                 445 gga gtc aat ttt gga gca tct gat ttt gct tac act gca tac tcc atg      1512
Gly Val Asn Phe Gly Ala Ser Asp Phe Ala Tyr Thr Ala Tyr Ser Met
450                 455                 460                 465 gtg gga gtg gcg gcc ata agc att gca gca gta ata tat atg gca aag      1560
Val Gly Val Ala Ala Ile Ser Ile Ala Ala Val Ile Tyr Met Ala Lys
                470                 475                 480 acc aat ggt ttc ata gga ata tgg ata gct ctt aca atc tat atg gct      1608
Thr Asn Gly Phe Ile Gly Ile Trp Ile Ala Leu Thr Ile Tyr Met Ala
            485                 490                 495 ctc cgg gct att act gga att gcc agg atg gcg aca gga act gga ccg      1656
Leu Arg Ala Ile Thr Gly Ile Ala Arg Met Ala Thr Gly Thr Gly Pro
        500                 505                 510 tgg agg ttc ttg cgt gga cga tca tcc tct tca tct tcc taggacttag       1705
Trp Arg Phe Leu Arg Gly Arg Ser Ser Ser Ser Ser Ser
    515                 520                 525 tttatttata acgagttgca tctcttcttc cttcttcgtt tttgtttatg gttcttgtgt    1765
ttgtttttca acattttgtt cgagagaccg ttatcatatt atcagtttca cataaataat   1825
gcatattttt aagtcattaa aataaaaaaa aaaaaaaaaa aaa                      1868

<210> SEQ ID NO 3
<211> LENGTH: 526
<212> TYPE: PRT
<213> ORGANISM: Arabidopsis thaliana

<400> SEQUENCE: 3

Met Thr Glu Thr Gly Asp Asp Leu Ala Thr Val Lys Lys Pro Ile Pro
1               5                   10                  15

Phe Leu Val Ile Phe Lys Asp Leu Arg His Val Phe Ser Arg Asp Thr
            20                  25                  30

Thr Gly Arg Glu Ile Leu Gly Ile Ala Phe Pro Ala Ala Leu Ala Leu
        35                  40                  45

Ala Ala Asp Pro Ile Asp Ser Leu Ile Asp Thr Ala Phe Val Gly Arg
    50                  55                  60

Leu Gly Ala Val Gln Leu Ala Ala Val Gly Val Ser Ile Ala Ile Phe
65                  70                  75                  80

Asn Gln Ala Ser Arg Ile Thr Ile Phe Pro Leu Val Ser Leu Thr Thr
                85                  90                  95

Ser Phe Val Ala Glu Glu Asp Thr Met Glu Lys Met Lys Glu Glu Ala
            100                 105                 110

Asn Lys Ala Asn Leu Val His Ala Glu Thr Ile Leu Val Gln Asp Ser
        115                 120                 125

Leu Glu Lys Gly Ile Ser Ser Pro Thr Ser Asn Asp Thr Asn Gln Pro
    130                 135                 140

Gln Gln Pro Pro Ala Pro Asp Thr Lys Ser Asn Ser Gly Asn Lys Ser
145                 150                 155                 160

Asn Lys Lys Glu Lys Arg Thr Ile Arg Thr Ala Ser Thr Ala Met Ile
                165                 170                 175

Leu Gly Leu Ile Leu Gly Leu Val Gln Ala Ile Phe Leu Ile Phe Ser
            180                 185                 190

Ser Lys Leu Leu Leu Gly Val Met Gly Val Lys Pro Asn Ser Pro Met
```

195                 200                 205
Leu Ser Pro Ala His Lys Tyr Leu Ser Ile Arg Ala Leu Gly Ala Pro
    210                 215                 220
Ala Leu Leu Leu Ser Leu Ala Met Gln Gly Ile Phe Arg Gly Phe Lys
225                 230                 235                 240
Asp Thr Lys Thr Pro Leu Phe Ala Thr Val Ala Asp Val Ile Asn
                245                 250                 255
Ile Val Leu Asp Pro Ile Phe Ile Phe Val Leu Arg Leu Gly Ile Ile
                260                 265                 270
Gly Ala Ala Ile Ala His Val Ile Ser Gln Tyr Phe Met Thr Leu Ile
            275                 280                 285
Leu Phe Val Phe Leu Ala Lys Lys Val Asn Leu Ile Pro Pro Asn Phe
    290                 295                 300
Gly Asp Leu Gln Phe Gly Arg Phe Leu Lys Asn Gly Leu Leu Leu Leu
305                 310                 315                 320
Ala Arg Thr Ile Ala Val Thr Phe Cys Gln Thr Leu Ala Ala Ala Met
                325                 330                 335
Ala Ala Arg Leu Gly Thr Thr Pro Met Ala Ala Phe Gln Ile Cys Leu
                340                 345                 350
Gln Val Trp Leu Thr Ser Ser Leu Leu Asn Asp Gly Leu Ala Val Ala
            355                 360                 365
Gly Gln Ala Ile Leu Ala Cys Ser Phe Ala Glu Lys Asp Tyr Asn Lys
    370                 375                 380
Val Thr Ala Val Ala Ser Arg Val Leu Gln Met Gly Phe Val Leu Gly
385                 390                 395                 400
Leu Gly Leu Ser Val Phe Val Gly Leu Gly Leu Tyr Phe Gly Ala Gly
                405                 410                 415
Val Phe Ser Lys Asp Pro Ala Val Ile His Leu Met Ala Ile Gly Ile
                420                 425                 430
Pro Phe Ile Ala Ala Thr Gln Pro Ile Asn Ser Leu Ala Phe Val Leu
            435                 440                 445
Asp Gly Val Asn Phe Gly Ala Ser Asp Phe Ala Tyr Thr Ala Tyr Ser
    450                 455                 460
Met Val Gly Val Ala Ala Ile Ser Ile Ala Ala Val Ile Tyr Met Ala
465                 470                 475                 480
Lys Thr Asn Gly Phe Ile Gly Ile Trp Ile Ala Leu Thr Ile Tyr Met
                485                 490                 495
Ala Leu Arg Ala Ile Thr Gly Ile Ala Arg Met Ala Thr Gly Thr Gly
            500                 505                 510
Pro Trp Arg Phe Leu Arg Gly Arg Ser Ser Ser Ser Ser
    515                 520                 525

<210> SEQ ID NO 4
<211> LENGTH: 5737
<212> TYPE: DNA
<213> ORGANISM: Arabidopsis thaliana

<400> SEQUENCE: 4
tttctacata ttttgattc cattttcata agaaatctt cagtatatta ttacattcat    60
atttattact tctttattat ttaaagtgat cattccaatt ttatatatag aaaattattt   120
atttatttat ggcaaggttg caacatataa aaaaaagtt ggtatacaaa caaatatcta   180
aaataatccc ctctaaactc tcctagatac tcactcatca ctactcatct caagttcacg   240
tgactactta tataagcgtt gactacataa aggtaagata ttctctccac atatctcata   300

```
agttctatga ttttcttag tattgcatat atgttctcta tcctactagg atatatcaac    360
acaacataca caagttctca attgaattag aagctcatga gtaactataa ctgtatatat    420
agttaactag attacgagta agaatgcaat tgtaaagcct tttaattgaa cttcttcttc    480
ttttttgat aaaaggtttt taattaaaaa aacaagtaat taaccattac aagctaggac    540
aactaagtca tacatgttga gagtagtgag agagttaagc aaaagcttaa tctagtcctt    600
ttaaaagcta acaaacatag tagagattat aagatgtttg gtgtaaataa caacaatacc    660
cagtttgtac atgtgtttag aaaatagttt ggattatggt ctaaaatata taaattataa    720
gaaagatgat gtctaacgat tcaacatagc aaaagatgat gtacacaaat gttttgttt    780
tacccatgta aaaaacaga acattagttg ttaagtttat aggtttattt tctacattaa    840
ttttcacaac tttttagtac cagaacgcac aatcaattaa gttttcatct tctatatata    900
ctgatctaaa aatattaata taaggtttgg gataattcaa tttaatcaca tcgtttataa    960
aaagcggtta actctacgat aactaaataa attgtgttat atgaaaaggg gaagtggcaa   1020
tgtaggtaat ggaattgacg ttgatggctt gaaaaagatg gccttatctt gcggaacaaa   1080
caattacata cacgacacgc actatataca actcacctgt gttggtctct gttgccatct   1140
tttatgttat tgttttccga ctgtcgcctt cctttaacta atattataat tttaaagatg   1200
ttcataaatc acagtagaaa gcttgttttt gctaaaatga acatgacacg gatcatacaa   1260
aaaatatatt ttacactata gctatatacc gatttaatct taggtacttt gaatcgtgct   1320
aaaactaaac ggccttctca aaaccctccc tcttttcctc cctccctcag aaaccccctcc   1380
atcgacaaat aacgttatgc aattctctaa acaatgctcg acaagcatgt gttttagta   1440
atgctacaac ttatttctct tttcaacgtc ctaagaggca tcaaaaagat caaagatctt   1500
ggaaccgagg tcctatgcaa ggaatcatta taaagtacca tgttattttt ttaaataaca   1560
tcgttttctt aatataattt ataaataccg ttatttttac cgaaatttca tatatatgtc   1620
agttttatac tttgtacgat aacgccaaaa actttaatta tcgccaaaat tgtaaacggt   1680
attttcgtcg tttagttatt taccaaaaat aaaatgacga ttgcaactta tttagttaaa   1740
atacaaaaaa aaactaatat attaattgag cggacggaat ttttttccaa aatcccgatg   1800
tgtaaatatg agaacgtttc gaggataact tacaaattaa acattaataa aaatgataaa   1860
gtgtagttag gagctaaatt gtgatagtaa acatctatct ctaatattat taaatgaatt   1920
ataatactat tttaatcata gtattaaatt tctttaatta aaaatataaa taatttcaat   1980
ttaattctat accaaattaa cccgaaaata ttttatctaa catacacaaa gacacataaa   2040
agttttgata actgcctaaa aaaataagct tttgaattat taattagttg ttattcaatg   2100
ataaaataac attatttgtc aactagtgaa ttccaattac gcaaaatgat tcactttttt   2160
agtggaaaat atcaaagaaa aatgagaagt ttatatgaaa ataaactctt tcccactatg   2220
atgaatacat gtaagaaaac tttcatgaaa agaaaactta tttactcaat ataaaaatag   2280
aagactcttt atctttcacg agtaaaagtt cacgaaaacc atattttcct attgattaaa   2340
gaaatcatag aagttaaaat aatcaacaag ggcaagccaa aaacttctag tgtgggattt   2400
acttaataga agtatatata ttacgatgtt tatgcgtacc tattttccct caatgagaag   2460
agaaattcca taatattggt gtcttaagtt tggacgaaa taaagagcag caaaaaagtt   2520
agggaaggaa acctttgttt tcttcaataa ttatagaaaa taatttcttt tattgattta   2580
gatattaaat aagcaaagat atgcatgctc attacgtgtc tataaataaa aacacgtttg   2640
```

```
tacatagcat ctactataaa cgttcctttt gcttccccga ttcttcgaaa cacttattga   2700
tatcttcaga cacaacaaat taattacaga gacagttaca gaggaaaaag atctatgacg   2760
gaaactggtg atgatcttgc tacggtgaag aagccaatcc catttctcgt tatcttcaaa   2820
gatttaaggt gtgtgtttat gtattcatga aatggtgatg aaattttga aagaagtgat    2880 gcataacatt agtttattta tgtaaaattg cagacatgta ttcagtaggg acacaactgg   2940
gcgagagatt ctaggcatcg cgtttccagc agctttggct ttagctgctg atccaatcgc   3000
ttctctgatt gataccgctt tgtcgggcg tttaggagcg gttcagctag cggcggttgg    3060
agtttccatt gccatattca atcaagcttc tagaattacg atattcccac ttgtgagcct   3120
cacaacttca tttgtggcag aggaagacac gatggagaag atgaagaag aagcaaacaa    3180 agccaatctt gttcatgcag aaactatact tgttcaagat tctttggaaa agggcatttc   3240
ttcacctaca agtaacgata ccaaccagcc acagcaacct ccaggtaaat tccgcatatc   3300
tcactcgaca ttgataactt ttattaaagt ttcgattgtt tttttactgt tggtttcttc   3360
tctcgatctc ttttgtttca atttgttgtt tttttggttg tattaaactt agctccggat   3420
acaaagtcaa atagcggaaa caaatcgaat aaaaaggaga agaggaccat tagaacagca   3480
tcaacagcta tgatcttggg gttaatcctt ggccttgtgc aagctatttt cttgattttc   3540
agttcaaagt tgcttctagg cgtcatggga gtgaaaccag taagttttca gaaatataca   3600
tattttgttg ggatctatag cataaaatgt tttgactaat ttgagttgaa tttggataac   3660
agaattcacc aatgttatca ccagcacaca agtacttgag catacgagct ttgggggctc   3720
ctgcattgct tctatctctt gctatgcaag gcatctttcg tggattcaag gacaccaaaa   3780
ctcctctctt tgccactggt aattaagttg ttaacttaga tcatctttaa tgatcactct   3840
ccttacttct tataatattt tgccttaatg cgtgaaacag tcgtagcaga tgttatcaac   3900
atagttctcg accccatctt catttttgtg cttcgtctag ggatcatcgg tgcagccatt   3960
gcccatgtca tttctcagta agagaaatca ctaaaaaaat tccacacatg caaaagtgat   4020
cattattgaa caaaatcgct aggcgcactc ttgttttttct acagctataa atagacttgt   4080
gaagtcataa cctcaaacaa aaacaaatga tttgtttgtg tacgtgaagg tacttcatga   4140
ctctaatatt gttcgtcttc ctcgcaaaga aagttaattt gattccacca aacttcgggg   4200
atttgcagtt tggaaggttc cttaaaaatg gtacgtatgg atgcatattt attaaaagtt   4260
gtggttcttg caataatatt ttttttttaaa aacaagatcc gtcgtaggag ctaatgcaca   4320
gagtccaaaa ataaattaac aaaaaattta tctatataat aatagaattc aatcaaataa   4380
ggtctatatt taaatatttg aatattttga aatatatagt taagaaaatg agaaatgtgg   4440
atatatgtct aacaagtata gtattaaaaa tgaaagggct actattgctg gcgaggacca   4500
tagcagtgac gttttgtcag accttagcag cagcaatggc ggcgcggctg ggtacaacac   4560
caatggctgt tttcagatttt gtttacaagt atggttaact tcttctcttc tcaatgatgg   4620
tcttgccgtt gctggtcagg taatcatgtt ttctcgttgt attaatttat gtatagttta   4680
tatggttgat caagttgtat gtagaaaatg atcattcaat acgttgcagg cgattctggc   4740
ttgttcgttt gctgagaagg actataacaa agtgactgct gttgcatccc gtgttctaca   4800
ggttcggtcc aaaaatcaca ttaccaaacc tttctttaaa aataaaataa ttgtgtaact   4860
aaaacagaaa tgaatttgat acgcagatgg gttttgtgtt aggacttgga ctgtccgttt   4920
ttgttggact aggtctctac tttggtgccg gagttttctc caaggaccct gctgttattc   4980
acctcatggc catcggaata ccggtaacta ataatcaaat aataattact atagtataaa   5040
```

-continued

```
aatcatttta aaagaattttt actaatgaga agaggttata tatatttatg cagtttatag    5100
cagcaacgca gccaataaac tctctcgcct ttgtattgga tggagtcaat tttggagcat    5160
ctgattttgc ttacactgca tactccatgg tatgcacact atatatacta tgaaatgatt    5220
aaaattcctt tttttttttt tgaaatgact taaactttgt ctatcttttt ttcttgtaat    5280
ccaattatga taaatcaggt gggagtggcg gccataagca ttgcagcagt aatatatatg    5340
gcaaagacca atggtttcat aggaatatgg atagctctta caatctatat ggctctccgg    5400
gctattactg gaattgccag gtatttaaat tgggccttta ctatagccca ctatagtaga    5460
agcagtattt gactgagtgt ttgaatttat gcaggatggc gacaggaact ggaccgtgga    5520
ggttcttgcg tggacgatca tcctcttcat cttcctagga cttagtttat ttataacgag    5580
ttgcatctct tcttccttct tcgttttttgt ttatggttct tgtgtttgtt tttcaacatt    5640
ttgttcgaga gaccgttatc atattatcag tttcacataa ataatgcata tttttaagtc    5700
attaaaatat ggagccctct gccctcactg gcttttc                             5737
```

<210> SEQ ID NO 5
<211> LENGTH: 1867
<212> TYPE: DNA
<213> ORGANISM: Arabidopsis thaliana
<220> FEATURE:
<221> NAME/KEY: CDS
<222> LOCATION: (118)...(1182)

<400> SEQUENCE: 5

```
aaataatccc ctctaaactc tcctagatac tcactcatca ctactcatct caagttcacg     60
tgactactta tataagcgtt gactacataa agagacagtt acagaggaaa aagatct atg    120
                                                                 Met
                                                                  1 acg gaa act ggt gat gat ctt gct acg gtg aag aag cca atc cca ttt      168
Thr Glu Thr Gly Asp Asp Leu Ala Thr Val Lys Lys Pro Ile Pro Phe
       5                  10                  15 ctc gtt atc ttc aaa gat tta aga cat gta ttc agt agg gac aca act      216
Leu Val Ile Phe Lys Asp Leu Arg His Val Phe Ser Arg Asp Thr Thr
 20                  25                  30 ggg cga gag att cta ggc atc gcg ttt cca gca gct ttg gct tta gct      264
Gly Arg Glu Ile Leu Gly Ile Ala Phe Pro Ala Ala Leu Ala Leu Ala
 35                  40                  45 gct gat cca atc gct tct ctg att gat acc gct ttt gtc ggg cgt tta      312
Ala Asp Pro Ile Ala Ser Leu Ile Asp Thr Ala Phe Val Gly Arg Leu
 50                  55                  60                  65 gga gcg gtt cag cta gcg gcg gtt gga gtt tcc att gcc ata ttc aat      360
Gly Ala Val Gln Leu Ala Ala Val Gly Val Ser Ile Ala Ile Phe Asn
             70                  75                  80 caa gct tct aga att acg ata ttc cca ctt gtg agc ctc aca act tca      408
Gln Ala Ser Arg Ile Thr Ile Phe Pro Leu Val Ser Leu Thr Thr Ser
         85                  90                  95 ttt gtg gca gag gaa gac acg atg gag aag atg aaa gaa gaa gca aac      456
Phe Val Ala Glu Glu Asp Thr Met Glu Lys Met Lys Glu Glu Ala Asn
    100                 105                 110 aaa gcc aat ctt gtt cat gca gaa act ata ctt gtt caa gat tct ttg      504
Lys Ala Asn Leu Val His Ala Glu Thr Ile Leu Val Gln Asp Ser Leu
115                 120                 125 gaa aag ggc att tct tca cct aca agt aac gat acc aac cag cca cag      552
Glu Lys Gly Ile Ser Ser Pro Thr Ser Asn Asp Thr Asn Gln Pro Gln
130                 135                 140                 145 caa cct cca gct ccg gat aca aag tca aat agc gga aac aaa tcg aat      600
```

```
Gln Pro Pro Ala Pro Asp Thr Lys Ser Asn Ser Gly Asn Lys Ser Asn
            150                 155                 160 aaa aag gag aag agg acc att aga aca gca tca aca gct atg atc ttg       648
Lys Lys Glu Lys Arg Thr Ile Arg Thr Ala Ser Thr Ala Met Ile Leu
                165                 170                 175 ggg tta atc ctt ggc ctt gtg caa gct att ttc ttg att ttc agt tca       696
Gly Leu Ile Leu Gly Leu Val Gln Ala Ile Phe Leu Ile Phe Ser Ser
            180                 185                 190 aag ttg ctt cta ggc gtc atg gga gtg aaa cca aat tca cca atg tta       744
Lys Leu Leu Leu Gly Val Met Gly Val Lys Pro Asn Ser Pro Met Leu
        195                 200                 205 tca cca gca cac aag tac ttg agc ata cga gct ttg ggg gct cct gca       792
Ser Pro Ala His Lys Tyr Leu Ser Ile Arg Ala Leu Gly Ala Pro Ala
210                 215                 220                 225 ttg ctt cta tct ctt gct atg caa ggc atc ttt cgt gga ttc aag gac       840
Leu Leu Leu Ser Leu Ala Met Gln Gly Ile Phe Arg Gly Phe Lys Asp
                230                 235                 240 acc aaa act cct ctc ttt gcc act gtc gta gca gat gtt atc aac ata       888
Thr Lys Thr Pro Leu Phe Ala Thr Val Val Ala Asp Val Ile Asn Ile
                245                 250                 255 gtt ctc gac ccc atc ttt att ttt gtg ctt cgt cta ggg atc atc ggt       936
Val Leu Asp Pro Ile Phe Ile Phe Val Leu Arg Leu Gly Ile Ile Gly
            260                 265                 270 gca gcc att gcc cat gtc att tct cag tac ttc atg act cta ata ttg       984
Ala Ala Ile Ala His Val Ile Ser Gln Tyr Phe Met Thr Leu Ile Leu
        275                 280                 285 ttc gtc ttc ctc gca aag aaa gtt aat ttg att cca cca aac ttc ggg      1032
Phe Val Phe Leu Ala Lys Lys Val Asn Leu Ile Pro Pro Asn Phe Gly
290                 295                 300                 305 gat ttg cag ttt gga agg ttc ctt aaa aat ggg cta cta ttg ctg gcg      1080
Asp Leu Gln Phe Gly Arg Phe Leu Lys Asn Gly Leu Leu Leu Leu Ala
                310                 315                 320 agg acc ata gca gtg acg ttt tgt cag acc tta gca gca gca atg gcg      1128
Arg Thr Ile Ala Val Thr Phe Cys Gln Thr Leu Ala Ala Ala Met Ala
                325                 330                 335 gcg cgg ctg ggt aca aca cca atg gct gtt ttc aga ttt gtt tac aag      1176
Ala Arg Leu Gly Thr Thr Pro Met Ala Val Phe Arg Phe Val Tyr Lys
            340                 345                 350 tat ggt taacttcttc tcttctcaat gatggtcttg ccgttgctgg tcaggcgatt      1232
Tyr Gly
    355 ctggcttgtt cgtttgctga gaaggactat aacaaagtga ctgctgttgc atcccgtgtt      1292 ctacagatgg gttttgtgtt aggacttgga ctgtccgttt tgttggact aggtctctac       1352 tttggtgccg gagttttctc caaggaccct gctgttattc acctcatggc catcggaata       1412 ccgtttatag cagcaacgca gccaataaac tctctcgcct tgtattgga tggagtcaat        1472 tttggagcat ctgattttgc ttacactgca tactccatgg tgggagtggc ggccataagc      1532 attgcagcag taatatatat ggcaaagacc aatggtttca taggaatatg gatagctctt      1592 acaatctata tggctctccg ggctattact ggaattgcca ggatggcgac aggaactgga      1652 ccgtggaggt tcttgcgtgg acgatcatcc tcttcatctt cctaggactt agtttattta      1712 taacgagttg catctcttct tccttcttcg tttttgttta tggttcttgt gtttgttttt      1772 caacattttg ttcgagagac cgttatcata ttatcagttt cacataaata atgcatattt      1832 ttaagtcatt aaaataaaaa aaaaaaaaaa aaaaa                                 1867
```

<210> SEQ ID NO 6

```
<211> LENGTH: 355
<212> TYPE: PRT
<213> ORGANISM: Arabidopsis thaliana

<400> SEQUENCE: 6

Met Thr Glu Thr Gly Asp Asp Leu Ala Thr Val Lys Lys Pro Ile Pro
 1               5                  10                  15

Phe Leu Val Ile Phe Lys Asp Leu Arg His Val Phe Ser Arg Asp Thr
            20                  25                  30

Thr Gly Arg Glu Ile Leu Gly Ile Ala Phe Pro Ala Ala Leu Ala Leu
        35                  40                  45

Ala Ala Asp Pro Ile Ala Ser Leu Ile Asp Thr Ala Phe Val Gly Arg
    50                  55                  60

Leu Gly Ala Val Gln Leu Ala Ala Val Gly Val Ser Ile Ala Ile Phe
65                  70                  75                  80

Asn Gln Ala Ser Arg Ile Thr Ile Phe Pro Leu Val Ser Leu Thr Thr
                85                  90                  95

Ser Phe Val Ala Glu Glu Asp Thr Met Glu Lys Met Lys Glu Glu Ala
            100                 105                 110

Asn Lys Ala Asn Leu Val His Ala Glu Thr Ile Leu Val Gln Asp Ser
        115                 120                 125

Leu Glu Lys Gly Ile Ser Ser Pro Thr Ser Asn Asp Thr Asn Gln Pro
    130                 135                 140

Gln Gln Pro Pro Ala Pro Asp Thr Lys Ser Asn Ser Gly Asn Lys Ser
145                 150                 155                 160

Asn Lys Lys Glu Lys Arg Thr Ile Arg Thr Ala Ser Thr Ala Met Ile
                165                 170                 175

Leu Gly Leu Ile Leu Gly Leu Val Gln Ala Ile Phe Leu Ile Phe Ser
            180                 185                 190

Ser Lys Leu Leu Leu Gly Val Met Gly Val Lys Pro Asn Ser Pro Met
        195                 200                 205

Leu Ser Pro Ala His Lys Tyr Leu Ser Ile Arg Ala Leu Gly Ala Pro
    210                 215                 220

Ala Leu Leu Leu Ser Leu Ala Met Gln Gly Ile Phe Arg Gly Phe Lys
225                 230                 235                 240

Asp Thr Lys Thr Pro Leu Phe Ala Thr Val Ala Asp Val Ile Asn
                245                 250                 255

Ile Val Leu Asp Pro Ile Phe Ile Phe Val Leu Arg Leu Gly Ile Ile
            260                 265                 270

Gly Ala Ala Ile Ala His Val Ile Ser Gln Tyr Phe Met Thr Leu Ile
        275                 280                 285

Leu Phe Val Phe Leu Ala Lys Lys Val Asn Leu Ile Pro Pro Asn Phe
    290                 295                 300

Gly Asp Leu Gln Phe Gly Arg Phe Leu Lys Asn Gly Leu Leu Leu Leu
305                 310                 315                 320

Ala Arg Thr Ile Ala Val Thr Phe Cys Gln Thr Leu Ala Ala Ala Met
                325                 330                 335

Ala Ala Arg Leu Gly Thr Thr Pro Met Ala Val Phe Arg Phe Val Tyr
            340                 345                 350

Lys Tyr Gly
        355

<210> SEQ ID NO 7
<211> LENGTH: 5738
<212> TYPE: DNA
```

<213> ORGANISM: Arabidopsis thaliana

<400> SEQUENCE: 7

```
tttctacata ttttgattc cattttcata agaaaatctt cagtatatta ttacattcat      60
atttattact tctttattat ttaaagtgat cattccaatt ttatatatag aaaattattt     120
atttatttat ggcaaggttg caacatataa aaaaaagtt ggtatacaaa caaatatcta     180
aaataatccc ctctaaactc tcctagatac tcactcatca ctactcatct caagttcacg     240
tgactactta tataagcgtt gactacataa aggtaagata ttctctccac atatctcata     300
agttctatga tttttcttag tattgcatat atgttctcta tcctactagg atatatcaac     360
acaacataca caagttctca attgaattag aagctcatga gtaactataa ctgtatatat     420
agttaactag attacgagta agaatgcaat tgtaaagcct tttaattgaa cttcttcttc     480
ttttttgat aaaggtttt taattaaaaa aacaagtaat taaccattac aagctaggac     540
aactaagtca tacatgttga gagtagtgag agagttaagc aaaagcttaa tctagtcctt     600
ttaaagcta acaaacatag tagagattat aagatgtttg gtgtaaataa caacaatacc     660
cagtttgtac atgtgtttag aaaatagttt ggattatggt ctaaatata taaattataa     720
gaaagatgat gtctaacgat tcaacatagc aaaagatgat gtacacaaat gttttgttt     780
tacccatgta aaaaaacaga acattagttg ttaagtttat aggtttattt tctacattaa     840
ttttcacaac tttttagtac cagaacgcac aatcaattaa gttttcatct tctatatata     900
ctgatctaaa aatattaata taaggtttgg gataattcaa tttaatcaca tcgtttataa     960
aaagcggtta actctacgat aactaaataa attgtgttat atgaaaaggg gaagtggcaa    1020
tgtaggtaat ggaattgacg ttgatggctt gaaaaagatg gccttatctt gcggaacaaa    1080
caattacata cacgacacgc actatataca actcacctgt gttggtctct gttgccatct    1140
tttatgttat tgttttccga ctgtcgcctt ccttaacta atattataat tttaaagatg    1200
ttcataaatc acagtagaaa gcttgttttt gctaaaatga acatgacacg gatcatacaa    1260
aaaatatatt ttcacctata gctatatacc gatttaatct taggtacttt gaatcgtgct    1320
aaaactaaac ggccttctca aaaccctccc tctttcctc cctccctcag aaaccctcc    1380
atcgacaaat aacgttatgc aattctctaa acaatgctcg acaagcatgt gtttttagta    1440
atgctacaac ttatttctct tttcaacgtc ctaagaggca tcaaaaagat caaagatctt    1500
ggaaccgagg tcctatgcaa ggaatcatta taaagtacca tgttatttt ttaaataaca    1560
tcgtttctt aatataattt ataaataccg ttattttac cgaaatttca tatatatgtc    1620
agttttatac tttgtacgat aacgccaaaa actttaatta tcgccaaaat tgtaaacggt    1680
atttcgtcg tttagttatt taccaaaaat aaaatgacga ttgcaactta tttagttaaa    1740
atacaaaaaa aaactaatat attaattgag cggacggaat ttttttccaa atcccgatg    1800
tgtaaatatg agaacgtttc gaggataact tacaaattaa acattaataa aaatgataaa    1860
gtgtagttag gagctaaatt gtgatagtaa acatctatct ctaatattat taaatgaatt    1920
ataatactat tttaatcata gtattaaatt tctttaatta aaaatataaa taatttcaat    1980
ttaattctat accaaattaa cccgaaaata ttttatctaa catacacaaa gacacataaa    2040
agttttgata actgcctaaa aaaataagct tttgaattat taattagttg ttattcaatg    2100
ataaaataac attatttgtc aactagtgaa ttccaattac gcaaaatgat tcactttttt    2160
agtggaaaat atcaaagaaa aatgagaagt ttatatgaaa ataaactctt tcccactatg    2220
atgaatacat gtaagaaaac tttcatgaaa agaaaactta tttactcaat ataaaaatag    2280
```

```
aagactcttt atctttcacg agtaaaagtt cacgaaaacc atattttcct attgattaaa    2340
gaaatcatag aagttaaaat aatcaacaag ggcaagccaa aaacttctag tgtgggattt    2400
acttaataga agtatatata ttacgatgtt tatgcgtacc tattttccct caatgagaag    2460
agaaattcca taatattggt gtcttaagtt tggacggaaa taaagagcag caaaaaagtt    2520
agggaaggaa acctttgttt tcttcaataa ttatagaaaa taatttcttt tattgattta    2580
gatattaaat aagcaaagat atgcatgctc attacgtgtc tataaataaa aacacgtttg    2640
tacatagcat ctactataaa cgttccttt gcttccccga ttcttcgaaa cacttattga     2700
tatcttcaga cacaacaaat taattacaga gacagttaca gaggaaaaag atctatgacg    2760
gaaactggtg atgatcttgc tacggtgaag aagccaatcc catttctcgt tatcttcaaa    2820
gatttaaggt gtgtgtttat gtattcatga aatggtgatg aaattttga aagaagtgat     2880 gcataacatt agtttatta tgtaaaattg cagacatgta ttcagtaggg acacaactgg     2940
gcgagagatt ctaggcatcg cgtttccagc agctttggct ttagctgctg atccaatcgc    3000
ttctctgatt gataccgctt tgtcgggcg tttaggagcg gttcagctag cggcggttgg     3060
agtttccatt gccatattca atcaagcttc tagaattacg atattcccac ttgtgagcct    3120
cacaacttca tttgtggcag aggaagacac gatggagaag atgaaagaag aagcaaacaa    3180
agccaatctt gttcatgcag aaactatact tgttcaagat tctttggaaa agggcatttc    3240
ttcacctaca agtaacgata ccaaccagcc acagcaacct ccaggtaaat tccgcatatc    3300
tcactcgaca ttgataactt ttattaaagt ttcgattgtt tttttactgt tggtttcttc    3360
tctcgatctc ttttgtttca atttgttgtt tttttggttg tattaaactt agctccggat    3420
acaaagtcaa atagcggaaa caaatcgaat aaaaaggaga agaggaccat tagaacagca    3480
tcaacagcta tgatcttggg gttaatcctt ggccttgtgc aagctatttt cttgattttc    3540
agttcaaagt tgcttctagg cgtcatggga gtgaaaccag taagttttca gaaatataca    3600
tattttgttg ggatctatag cataaaatgt tttgactaat ttgagttgaa tttggataac    3660
agaattcacc aatgttatca ccagcacaca agtacttgag catacgagct ttgggggctc    3720
ctgcattgct tctatctctt gctatgcaag gcatctttcg tggattcaag gacaccaaaa    3780
ctcctctctt tgccactgat aattaagttg ttaacttaga tcatctttaa tgatcactct    3840
ccttacttct tataatattt tgccttaatg cgtgaaacag tcgtagcaga tgttatcaac    3900
atagttctcg accccatctt catttttgtg cttcgtctag ggatcatcgg tgcagccatt    3960
gcccatgtca tttctcagta agagaaatca ctaaaaaaat tccacacatg caaaagtgat    4020
cattattgaa caaaatcgct aggcgcactc ttgttttct acagctataa atagacttgt      4080
gaagtcataa cctcaaacaa aaacaaatga tttgtttgtg tacgtgaagg tacttcatga    4140
ctctaatatt gttcgtcttc ctcgcaaaga aagttaattt gattccacca aacttcgggg    4200
atttgcagtt tggaaggttc cttaaaaatg gtacgtatgg atgcatattt attaaaagtt    4260
gtggttcttg caataatatt ttttttttaaa aacaagatcc gtcgtaggag ctaatgcaca   4320
gagtccaaaa ataaattaac aaaaaattta tctatataat aatagaattc aatcaaataa    4380
ggtctatatt taaatattg aatattttga aatatatagt taagaaaatg agaaatgtgg     4440
atatatgtct aacaagtata gtattaaaaa tgaaagggct actattgctg gcgaggacca    4500
tagcagtgac gttttgtcag accttagcag cagcaatggc ggcgcggctg ggtacaacac    4560
caatggctgc ttttcagatt tgtttacaag tatggttaac ttcttctctt ctcaatgatg    4620
```

```
gtcttgccgt tgctggtcag gtaatcatgt tttctcgttg tattaattta tgtatagttt    4680
atatggttga tcaagttgta tgtagaaaat gatcattcaa tacgttgcag gcgattctgg    4740
cttgttcgtt tgctgagaag gactataaca aagtgactgc tgttgcatcc cgtgttctac    4800
aggttcggtc caaaaatcac attaccaaac ctttctttaa aaataaaata attgtgtaac    4860
taaaacagaa atgaatttga tacgcagatg ggttttgtgt taggacttgg actgtccgtt    4920
tttgttggac taggtctcta ctttggtgcc ggagttttct ccaaggaccc tgctgttatt    4980
cacctcatgg ccatcggaat accggtaact aataatcaaa taataattac tatagtataa    5040
aaatcatttt aaaagaattt tactaatgag aagaggttat atatatttat gcagtttata    5100
gcagcaacgc agccaataaa ctctctcgcc tttgtattgg atggagtcaa ttttggagca    5160
tctgattttg cttacactgc atactccatg gtatgcacac tatatatact atgaaatgat    5220
taaaattcct ttttttttt ttgaaatgac ttaaactttg tctatctttt tttcttgtaa     5280
tccaattatg ataaatcagg tgggagtggc ggccataagc attgcagcag taatatatat    5340
ggcaaagacc aatggtttca taggaatatg gatagctctt acaatctata tggctctccg    5400
ggctattact ggaattgcca ggtatttaaa ttgggccttt actatagccc actatagtag    5460
aagcagtatt tgactgagtg tttgaattta tgcaggatgg cgacaggaac tggaccgtgg    5520
aggttcttgc gtggacgatc atcctcttca tcttcctagg acttagttta tttataacga    5580
gttgcatctc ttcttccttc ttcgtttttg tttatggttc ttgtgtttgt ttttcaacat    5640
tttgttcgag agaccgttat catattatca gtttcacata aataatgcat attttttaagt   5700 cattaaaata tggagccctc tgccctcact ggctttc                             5738

<210> SEQ ID NO 8
<211> LENGTH: 1950
<212> TYPE: DNA
<213> ORGANISM: Arabidopsis thaliana
<220> FEATURE:
<221> NAME/KEY: CDS
<222> LOCATION: (118)...(870)

<400> SEQUENCE: 8
aaataatccc ctctaaactc tcctagatac tcactcatca ctactcatct caagttcacg      60
tgactactta tataagcgtt gactacataa agagacagtt acagaggaaa aagatct atg    120
                                                                 Met
                                                                  1 acg gaa act ggt gat gat ctt gct acg gtg aag aag cca atc cca ttt       168
Thr Glu Thr Gly Asp Asp Leu Ala Thr Val Lys Lys Pro Ile Pro Phe
        5                  10                  15 ctc gtt atc ttc aaa gat tta aga cat gta ttc agt agg gac aca act       216
Leu Val Ile Phe Lys Asp Leu Arg His Val Phe Ser Arg Asp Thr Thr
 20                  25                  30 ggg cga gag att cta ggc atc gcg ttt cca gca gct ttg gct tta gct       264
Gly Arg Glu Ile Leu Gly Ile Ala Phe Pro Ala Ala Leu Ala Leu Ala
 35                  40                  45 gct gat cca atc gct tct ctg att gat acc gct ttt gtc ggg cgt tta       312
Ala Asp Pro Ile Ala Ser Leu Ile Asp Thr Ala Phe Val Gly Arg Leu
 50                  55                  60                  65 gga gcg gtt cag cta gcg gcg gtt gga gtt tcc att gcc ata ttc aat       360
Gly Ala Val Gln Leu Ala Ala Val Gly Val Ser Ile Ala Ile Phe Asn
                 70                  75                  80 caa gct tct aga att acg ata ttc cca ctt gtg agc ctc aca act tca       408
Gln Ala Ser Arg Ile Thr Ile Phe Pro Leu Val Ser Leu Thr Thr Ser
         85                  90                  95
```

| | | | | | | | | | | | | | | | | |
|---|---|---|---|---|---|---|---|---|---|---|---|---|---|---|---|---|
| ttt | gtg | gca | gag | gaa | gac | acg | atg | gag | aag | atg | aaa | gaa | gaa | gca | aac | 456 |
| Phe | Val | Ala | Glu | Glu | Asp | Thr | Met | Glu | Lys | Met | Lys | Glu | Glu | Ala | Asn | |
| | | | | 100 | | | | | 105 | | | | | 110 | | |
| aaa | gcc | aat | ctt | gtt | cat | gca | gaa | act | ata | ctt | gtt | caa | gat | tct | ttg | 504 |
| Lys | Ala | Asn | Leu | Val | His | Ala | Glu | Thr | Ile | Leu | Val | Gln | Asp | Ser | Leu | |
| | 115 | | | | | 120 | | | | | 125 | | | | | |
| gaa | aag | ggc | att | tct | tca | cct | aca | agt | aac | gat | acc | aac | cag | cca | cag | 552 |
| Glu | Lys | Gly | Ile | Ser | Ser | Pro | Thr | Ser | Asn | Asp | Thr | Asn | Gln | Pro | Gln | |
| 130 | | | | | 135 | | | | | 140 | | | | | 145 | |
| caa | cct | cca | gct | ccg | gat | aca | aag | tca | aat | agc | gga | aac | aaa | tcg | aat | 600 |
| Gln | Pro | Pro | Ala | Pro | Asp | Thr | Lys | Ser | Asn | Ser | Gly | Asn | Lys | Ser | Asn | |
| | | | | 150 | | | | | 155 | | | | | 160 | | |
| aaa | aag | gag | aag | agg | acc | att | aga | aca | gca | tca | aca | gct | atg | atc | ttg | 648 |
| Lys | Lys | Glu | Lys | Arg | Thr | Ile | Arg | Thr | Ala | Ser | Thr | Ala | Met | Ile | Leu | |
| | 165 | | | | | 170 | | | | | 175 | | | | | |
| ggg | tta | atc | ctt | ggc | ctt | gtg | caa | gct | att | ttc | ttg | att | ttc | agt | tca | 696 |
| Gly | Leu | Ile | Leu | Gly | Leu | Val | Gln | Ala | Ile | Phe | Leu | Ile | Phe | Ser | Ser | |
| 180 | | | | | 185 | | | | | 190 | | | | | | |
| aag | ttg | ctt | cta | ggc | gtc | atg | gga | gtg | aaa | cca | aat | tca | cca | atg | tta | 744 |
| Lys | Leu | Leu | Leu | Gly | Val | Met | Gly | Val | Lys | Pro | Asn | Ser | Pro | Met | Leu | |
| | 195 | | | | 200 | | | | | 205 | | | | | | |
| tca | cca | gca | cac | aag | tac | ttg | agc | ata | cga | gct | ttg | ggg | gct | cct | gca | 792 |
| Ser | Pro | Ala | His | Lys | Tyr | Leu | Ser | Ile | Arg | Ala | Leu | Gly | Ala | Pro | Ala | |
| 210 | | | | 215 | | | | | 220 | | | | | 225 | | |
| ttg | ctt | cta | tct | ctt | gct | atg | caa | ggc | atc | ttt | cgt | gga | ttc | aag | gac | 840 |
| Leu | Leu | Leu | Ser | Leu | Ala | Met | Gln | Gly | Ile | Phe | Arg | Gly | Phe | Lys | Asp | |
| | | | | 230 | | | | | 235 | | | | | 240 | | |
| acc | aaa | act | cct | ctc | ttt | gcc | act | gat | aat | taagttggta | | acttagatca | | | | 890 |
| Thr | Lys | Thr | Pro | Leu | Phe | Ala | Thr | Asp | Asn | | | | | | | |
| | 245 | | | | | 250 | | | | | | | | | | |

```
tctttaatga tcactctcct tacttcttat aatattttgc cttaatgcgt gaaacagtcg    950
tagcagatgt tatcaacata gttctcgacc ccatcttcat ttttgtgctt cgtctaggga   1010
tcatcggtgc agccattgcc catgtcattt ctcagtactt catgactcta atattgttcg   1070
tcttcctcgc aaagaaagtt aatttgattc caccaaactt cggggatttg cagtttggaa   1130
ggttccttaa aaatgggcta ctattgctgg cgaggaccat agcagtgacg ttttgtcaga   1190
ccttagcagc agcaatggcg gcgcggctgg gtacaacacc aatggctgct tttcagattt   1250
gtttacaagt atggttaact tcttctcttc tcaatgatgg tcttgccgtt gctggtcagg   1310
cgattctggc ttgttcgttt gctgagaagg actataacaa agtgactgct gttgcatccc   1370
gtgttctaca gatgggtttt gtgttaggac ttggactgtc cgttttttgtt ggactaggtc   1430
tctactttgg tgccggagtt ttctccaagg accctgctgt tattcacctc atggccatcg   1490
gaataccgtt tatagcagca acgcagccaa taaactctct cgcctttgta ttggatggag   1550
tcaattttgg agcatctgat tttgcttaca ctgcatactc catggtggga gtggcggcca   1610
taagcattgc agcagtaata tatatggcaa agaccaatgg tttcatagga atatggatag   1670
ctcttacaat ctatatggct ctccgggcta ttactggaat tgccaggatg gcgacaggaa   1730
ctggaccgtg gaggttcttg cgtggacgat catcctcttc atcttcctag gacttagttt   1790
atttataacg agttgcatct cttcttcctt cttcgttttt gtttatggtt cttgtgtttg   1850
tttttcaaca ttttgttcga gagaccgtta tcatattatc agtttcacat aaataatgca   1910
tatttttaag tcattaaaat aaaaaaaaaa aaaaaaaaa                          1950
```

<210> SEQ ID NO 9
<211> LENGTH: 251

```
<212> TYPE: PRT
<213> ORGANISM: Arabidopsis thaliana

<400> SEQUENCE: 9

Met Thr Glu Thr Gly Asp Asp Leu Ala Thr Val Lys Lys Pro Ile Pro
1               5                   10                  15

Phe Leu Val Ile Phe Lys Asp Leu Arg His Val Phe Ser Arg Asp Thr
                20                  25                  30

Thr Gly Arg Glu Ile Leu Gly Ile Ala Phe Pro Ala Ala Leu Ala Leu
            35                  40                  45

Ala Ala Asp Pro Ile Ala Ser Leu Ile Asp Thr Ala Phe Val Gly Arg
    50                  55                  60

Leu Gly Ala Val Gln Leu Ala Ala Val Gly Val Ser Ile Ala Ile Phe
65                  70                  75                  80

Asn Gln Ala Ser Arg Ile Thr Ile Phe Pro Leu Val Ser Leu Thr Thr
                85                  90                  95

Ser Phe Val Ala Glu Asp Thr Met Glu Lys Met Lys Glu Ala
                100                 105                 110

Asn Lys Ala Asn Leu Val His Ala Glu Thr Ile Leu Val Gln Asp Ser
            115                 120                 125

Leu Glu Lys Gly Ile Ser Ser Pro Thr Ser Asn Asp Thr Asn Gln Pro
    130                 135                 140

Gln Gln Pro Pro Ala Pro Asp Thr Lys Ser Asn Ser Gly Asn Lys Ser
145                 150                 155                 160

Asn Lys Lys Glu Lys Arg Thr Ile Arg Thr Ala Ser Thr Ala Met Ile
                165                 170                 175

Leu Gly Leu Ile Leu Gly Leu Val Gln Ala Ile Phe Leu Ile Phe Ser
            180                 185                 190

Ser Lys Leu Leu Leu Gly Val Met Gly Val Lys Pro Asn Ser Pro Met
    195                 200                 205

Leu Ser Pro Ala His Lys Tyr Leu Ser Ile Arg Ala Leu Gly Ala Pro
    210                 215                 220

Ala Leu Leu Leu Ser Leu Ala Met Gln Gly Ile Phe Arg Gly Phe Lys
225                 230                 235                 240

Asp Thr Lys Thr Pro Leu Phe Ala Thr Asp Asn
                245                 250

<210> SEQ ID NO 10
<211> LENGTH: 523
<212> TYPE: PRT
<213> ORGANISM: Arabidopsis thaliana

<400> SEQUENCE: 10

Met Thr Glu Thr Gly Asp Asp Leu Ala Thr Val Lys Lys Pro Ile Pro
1               5                   10                  15

Phe Leu Val Ile Phe Lys Asp Leu Arg His Val Phe Ser Arg Asp Thr
                20                  25                  30

Thr Gly Arg Glu Ile Leu Gly Ile Ala Phe Pro Ala Ala Leu Ala Leu
            35                  40                  45

Ala Ala Asp Pro Ile Ala Ser Leu Ile Asp Thr Ala Phe Val Gly Arg
    50                  55                  60

Leu Gly Ala Val Gln Leu Ala Ala Val Gly Val Ser Ile Ala Ile Phe
65                  70                  75                  80

Asn Gln Ala Ser Arg Ile Thr Ile Phe Pro Leu Val Ser Leu Thr Thr
                85                  90                  95
```

-continued

```
Ser Phe Val Ala Glu Glu Asp Thr Met Glu Lys Met Lys Glu Glu Ala
            100                 105                 110
Asn Lys Ala Asn Leu Val His Ala Glu Thr Ile Leu Val Gln Asp Ser
        115                 120                 125
Leu Glu Lys Gly Ile Ser Ser Pro Thr Ser Asn Asp Thr Asn Gln Pro
    130                 135                 140
Gln Gln Pro Pro Ala Pro Asp Thr Lys Ser Asn Ser Gly Asn Lys Ser
145                 150                 155                 160
Asn Lys Lys Glu Lys Arg Thr Ile Arg Thr Ala Ser Thr Ala Met Ile
                165                 170                 175
Leu Gly Leu Ile Leu Gly Leu Val Gln Ala Ile Phe Leu Ile Phe Ser
            180                 185                 190
Ser Lys Leu Leu Leu Gly Val Met Gly Val Lys Pro Asn Ser Pro Met
        195                 200                 205
Leu Ser Pro Ala His Lys Tyr Leu Ser Ile Arg Ala Leu Gly Ala Pro
    210                 215                 220
Ala Leu Leu Leu Ser Leu Ala Met Gln Gly Ile Phe Arg Gly Phe Lys
225                 230                 235                 240
Asp Thr Lys Thr Pro Leu Phe Ala Thr Val Val Ala Asp Val Ile Asn
                245                 250                 255
Ile Val Leu Asp Pro Ile Phe Ile Phe Val Leu Arg Leu Gly Ile Ile
            260                 265                 270
Gly Ala Ala Ile Ala His Val Ile Ser Gln Tyr Phe Met Thr Leu Ile
        275                 280                 285
Leu Phe Val Phe Leu Ala Lys Lys Val Asn Leu Ile Pro Pro Asn Phe
    290                 295                 300
Gly Asp Leu Gln Phe Gly Arg Phe Leu Lys Asn Gly Leu Leu Leu Leu
305                 310                 315                 320
Ala Arg Thr Ile Ala Val Thr Phe Cys Gln Thr Leu Ala Ala Ala Met
                325                 330                 335
Ala Ala Arg Leu Gly Thr Thr Pro Met Ala Ala Phe Gln Ile Cys Leu
            340                 345                 350
Gln Val Trp Leu Thr Ser Ser Leu Leu Asn Asp Gly Leu Ala Val Ala
        355                 360                 365
Gly Gln Ala Leu Ala Cys Ser Phe Ala Glu Lys Asp Tyr Asn Lys Val
    370                 375                 380
Thr Ala Val Ala Ser Arg Val Leu Gln Met Gly Phe Val Leu Gly Leu
385                 390                 395                 400
Gly Leu Ser Val Phe Val Gly Leu Gly Leu Tyr Phe Gly Ala Gly Val
                405                 410                 415
Phe Ser Lys Asp Pro Ala Val Ile His Leu Met Ala Ile Gly Ile Pro
            420                 425                 430
Phe Ala Ala Thr Gln Pro Ile Asn Ser Leu Ala Phe Val Leu Asp Gly
        435                 440                 445
Val Asn Phe Gly Ala Ser Asp Phe Ala Tyr Thr Ala Tyr Ser Met Val
    450                 455                 460
Gly Val Ala Ala Ile Ser Ala Ala Val Ile Tyr Met Ala Lys Thr Asn
465                 470                 475                 480
Gly Phe Ile Gly Ile Trp Ile Ala Leu Thr Ile Tyr Met Ala Leu Arg
                485                 490                 495
Ala Ile Thr Gly Ile Ala Arg Met Ala Thr Gly Thr Gly Pro Trp Arg
            500                 505                 510
Phe Leu Arg Gly Arg Ser Ser Ser Ser Ser Ser
```

-continued

```
                515                 520

<210> SEQ ID NO 11
<211> LENGTH: 16
<212> TYPE: PRT
<213> ORGANISM: Arabidopsis thaliana

<400> SEQUENCE: 11

Pro Ala Asn Asp Val Thr Leu Pro Ile Lys Glu Asp Ser Ser Asn
 1               5                  10                  15

<210> SEQ ID NO 12
<211> LENGTH: 501
<212> TYPE: PRT
<213> ORGANISM: Arabidopsis thaliana

<400> SEQUENCE: 12

Met Ser Glu Asp Gly Tyr Asn Thr Asp Phe Pro Arg Asn Pro Leu Tyr
 1               5                  10                  15

Ile Phe Phe Ser Asp Phe Arg Ser Val Leu Lys Phe Asp Glu Leu Gly
                20                  25                  30

Leu Glu Ile Ala Arg Ile Ala Leu Pro Ala Ala Leu Ala Leu Thr Ala
            35                  40                  45

Asp Pro Ile Ala Ser Leu Val Asp Thr Ala Phe Ile Gly Gln Ile Gly
        50                  55                  60

Pro Val Glu Leu Ala Ala Val Gly Val Ser Ile Ala Leu Phe Asn Gln
65                  70                  75                  80

Val Ser Arg Ile Ala Ile Phe Pro Leu Val Ser Ile Thr Thr Ser Phe
                85                  90                  95

Val Ala Glu Glu Asp Ala Cys Ser Ser Gln Gln Asp Thr Val Arg Asp
            100                 105                 110

His Lys Glu Cys Ile Glu Ile Gly Ile Asn Asn Pro Thr Glu Glu Thr
        115                 120                 125

Ile Glu Leu Ile Pro Glu Lys His Lys Asp Ser Leu Ser Asp Glu Phe
    130                 135                 140

Lys Thr Ser Ser Ser Ile Phe Ser Ile Ser Lys Pro Pro Ala Lys Lys
145                 150                 155                 160

Arg Asn Ile Pro Ser Ala Ser Ser Ala Leu Ile Ile Gly Gly Val Leu
                165                 170                 175

Gly Leu Phe Gln Ala Val Phe Leu Ile Ser Ala Ala Lys Pro Leu Leu
            180                 185                 190

Ser Phe Met Gly Val Lys His Asp Ser Pro Met Met Arg Pro Ser Gln
        195                 200                 205

Arg Tyr Leu Ser Leu Arg Ser Leu Gly Ala Pro Ala Val Leu Leu Ser
    210                 215                 220

Leu Ala Ala Gln Gly Val Phe Arg Gly Phe Lys Asp Thr Thr Thr Pro
225                 230                 235                 240

Leu Phe Ala Thr Val Ile Gly Asp Val Thr Asn Ile Ile Leu Asp Pro
                245                 250                 255

Ile Phe Ile Phe Val Phe Arg Leu Gly Val Thr Gly Ala Ala Thr Ala
            260                 265                 270

His Val Ile Ser Gln Tyr Leu Met Cys Gly Ile Leu Leu Trp Lys Leu
        275                 280                 285

Met Gly Gln Val Asp Ile Phe Asn Met Ser Thr Lys His Leu Gln Phe
    290                 295                 300

Cys Arg Phe Met Lys Asn Gly Phe Leu Leu Leu Met Arg Val Ile Ala
```

-continued

```
            305                 310                 315                 320
Val Thr Phe Cys Val Thr Leu Ser Ala Ser Leu Ala Ala Arg Glu Gly
                325                 330                 335

Ser Thr Ser Met Ala Ala Phe Gln Val Cys Leu Gln Val Trp Leu Ala
            340                 345                 350

Thr Ser Leu Leu Ala Asp Gly Tyr Ala Val Ala Gly Gln Ala Ile Leu
            355                 360                 365

Ala Ser Ala Phe Ala Lys Lys Asp Tyr Lys Arg Ala Ala Thr Ala
            370             375                 380

Ser Arg Val Leu Gln Leu Gly Leu Val Leu Gly Phe Val Leu Ala Val
385                 390                 395                 400

Ile Leu Gly Ala Gly Leu His Phe Gly Ala Arg Val Phe Thr Lys Asp
                405                 410                 415

Asp Lys Val Leu His Leu Ile Ser Ile Gly Leu Pro Phe Val Ala Gly
                420                 425                 430

Thr Gln Pro Ile Asn Ala Leu Ala Phe Val Phe Asp Gly Val Asn Phe
            435                 440                 445

Gly Ala Ser Asp Phe Gly Tyr Ala Ala Ala Ser Leu Val Met Val Ala
    450                 455                 460

Ile Val Ser Ile Leu Cys Leu Leu Phe Leu Ser Ser Thr His Gly Phe
465                 470                 475                 480

Ile Gly Leu Trp Phe Gly Leu Thr Ile Tyr Met Ser Leu Arg Ala Ala
                485                 490                 495

Val Gly Phe Trp Arg
            500

<210> SEQ ID NO 13
<211> LENGTH: 479
<212> TYPE: PRT
<213> ORGANISM: Arabidopsis thaliana

<400> SEQUENCE: 13

Met Leu Leu Cys Val Ser Cys Leu Cys Asn Ala Leu Val Ser Val Leu
1               5                   10                  15

Ala Arg Glu Val Asn Gly Val His Thr Gly Val Ala Arg Pro Val Asp
                20                  25                  30

Ile Lys Arg Glu Leu Val Met Leu Ser Leu Pro Ala Ile Ala Gly Gln
            35                  40                  45

Ala Ile Asp Pro Leu Thr Leu Leu Met Glu Thr Ala Tyr Ile Gly Arg
        50                  55                  60

Leu Gly Ser Val Glu Leu Gly Ser Ala Gly Val Ser Met Ala Ile Phe
65              70                  75                  80

Asn Thr Ile Ser Lys Leu Phe Asn Ile Pro Leu Leu Ser Val Ala Thr
                85                  90                  95

Ser Phe Val Ala Glu Asp Ile Ala Lys Ile Ala Ala Gln Asp Leu Ala
            100                 105                 110

Ser Glu Asp Ser Gln Ser Asp Ile Pro Ser Gln Gly Leu Pro Glu Arg
        115                 120                 125

Lys Gln Leu Ser Ser Val Ser Thr Ala Leu Val Leu Ala Ile Gly Ile
    130                 135                 140

Gly Ile Phe Glu Ala Leu Ala Leu Ser Leu Ala Ser Gly Pro Phe Leu
145                 150                 155                 160

Arg Leu Met Gly Ile Gln Ser Val Ser Ser Val Gln Arg Met Ser Glu
                165                 170                 175
```

-continued

```
Met Phe Ile Pro Ala Arg Gln Phe Leu Val Leu Arg Ala Leu Gly Ala
            180                 185                 190

Pro Ala Tyr Val Val Ser Leu Ala Leu Gln Gly Ile Phe Arg Gly Phe
        195                 200                 205

Lys Asp Thr Lys Thr Pro Val Tyr Cys Leu Val Leu Ser Phe Pro Asn
    210                 215                 220

Phe His Asn Ser Gly Ile Gly Asn Phe Leu Ala Val Phe Leu Phe Pro
225                 230                 235                 240

Leu Phe Ile Tyr Lys Phe Arg Met Gly Val Ala Gly Ala Ala Ile Ser
                245                 250                 255

Ser Val Ile Ser Gln Met Val Leu Asn Pro Phe Pro Leu Ile His Arg
            260                 265                 270

Tyr Thr Val Ala Ile Leu Met Leu Ile Leu Leu Asn Lys Arg Val Ile
        275                 280                 285

Leu Leu Pro Pro Lys Ile Gly Ser Leu Lys Phe Gly Asp Tyr Leu Lys
    290                 295                 300

Ser Gly Gly Phe Val Leu Gly Arg Thr Leu Ser Val Leu Val Thr Met
305                 310                 315                 320

Thr Val Ala Thr Ser Met Ala Ala Arg Gln Gly Val Phe Ala Met Ala
                325                 330                 335

Ala His Gln Ile Cys Met Gln Val Trp Leu Ala Val Ser Leu Leu Thr
            340                 345                 350

Asp Ala Leu Ala Ser Ser Gly Gln Ala Leu Ile Ala Ser Ser Ala Ser
        355                 360                 365

Lys Arg Asp Phe Glu Gly Val Lys Glu Phe Ile Phe Thr Phe Trp Gly
    370                 375                 380

Cys Tyr Leu Ile Ser Cys Tyr Ile Tyr Ile Tyr Arg Glu Arg Cys Asn
385                 390                 395                 400

Val Phe Gly Val Val Gln Ile Gly Val Val Thr Gly Ile Ala Leu Ala
                405                 410                 415

Ile Val Leu Gly Met Ser Phe Ser Ser Ile Ala Asp Gly Gly Gly Arg
            420                 425                 430

Asn Ile Ile Ser Val His Ala Val Cys Thr Gly Arg Val Gly Ala Lys
        435                 440                 445

Trp Ser Val Gly Ala Glu His Val His Gly Ile Ala Asp Gly Gly
    450                 455                 460

Trp Ile Gln Gln Val Lys Lys Glu Leu Pro Val Ser Ile Tyr Lys
465                 470                 475
```

<210> SEQ ID NO 14
<211> LENGTH: 484
<212> TYPE: PRT
<213> ORGANISM: Arabidopsis thaliana

<400> SEQUENCE: 14

```
Met Ala Asp Pro Ala Thr Ser Ser Pro Leu Leu Asp Asp His Val Gly
1               5                   10                  15

Gly Glu Asp Glu Arg Gly Arg Arg Ser Arg Ser Ser Thr Leu Val Gln
            20                  25                  30

Lys Val Ile Asp Val Glu Glu Ala Lys Ala Gln Met Ile Tyr Ser Leu
        35                  40                  45

Pro Met Ile Leu Thr Asn Val Phe Tyr Tyr Cys Ile Pro Ile Thr Ser
    50                  55                  60

Val Met Phe Ala Ser His Leu Gly Gln Leu Glu Leu Ala Gly Ala Thr
65                  70                  75                  80
```

-continued

```
Leu Ala Asn Ser Trp Ala Thr Val Ser Gly Phe Ala Phe Met Val Gly
                85                  90                  95

Leu Ser Gly Ser Leu Glu Thr Leu Cys Gly Gln Gly Phe Gly Ala Lys
            100                 105                 110

Arg Tyr Arg Met Leu Gly Val His Leu Gln Ser Ser Cys Ile Val Ser
            115                 120                 125

Leu Val Phe Ser Ile Leu Ile Thr Ile Phe Trp Phe Thr Glu Ser
    130                 135                 140

Ile Phe Gly Leu Leu Arg Gln Asp Pro Ser Ile Ser Lys Gln Ala Ala
145                 150                 155                 160

Leu Tyr Met Lys Tyr Gln Ala Pro Gly Leu Leu Ala Tyr Gly Phe Leu
                165                 170                 175

Gln Asn Ile Leu Arg Phe Cys Gln Thr Gln Ser Ile Ile Ala Pro Leu
            180                 185                 190

Val Ile Phe Ser Phe Val Pro Leu Val Ile Asn Ile Ala Thr Ala Tyr
        195                 200                 205

Val Leu Val Tyr Val Ala Gly Leu Gly Phe Ile Gly Ala Pro Ile Ala
    210                 215                 220

Thr Ser Ile Ser Leu Trp Ile Ala Phe Leu Ser Leu Gly Thr Tyr Val
225                 230                 235                 240

Met Cys Ser Glu Lys Phe Lys Glu Thr Trp Thr Gly Phe Ser Leu Glu
                245                 250                 255

Ser Phe Arg Tyr Ile Val Ile Asn Leu Thr Leu Ser Leu Pro Ser Ala
            260                 265                 270

Ala Met Leu Lys Arg Leu Tyr Cys Cys Asn Ser Leu Glu Tyr Trp Ala
        275                 280                 285

Phe Glu Ile Leu Val Phe Leu Ala Gly Val Met Pro Asn Pro Glu Ile
    290                 295                 300

Asn Thr Ser Leu Val Ala Ile Cys Val Asn Thr Glu Ala Ile Ser Tyr
305                 310                 315                 320

Met Leu Thr Tyr Gly Leu Ser Ala Ala Ala Ser Thr Arg Val Ser Asn
                325                 330                 335

Glu Leu Gly Ala Gly Asn Val Lys Gly Ala Lys Lys Ala Thr Ser Val
            340                 345                 350

Ser Val Lys Leu Ser Leu Val Leu Ala Leu Gly Val Val Ile Val Leu
        355                 360                 365

Leu Val Gly His Asp Gly Trp Val Gly Leu Phe Ser Asp Ser Tyr Val
    370                 375                 380

Ile Lys Glu Glu Phe Ala Ser Leu Arg Phe Phe Leu Ala Ala Ser Ile
385                 390                 395                 400

Thr Leu Asp Ser Ile Gln Gly Val Leu Ser Gly Val Ala Arg Gly Cys
                405                 410                 415

Gly Trp Gln Arg Leu Val Thr Val Ile Asn Leu Ala Thr Phe Tyr Leu
            420                 425                 430

Ile Gly Met Pro Ile Ala Ala Phe Cys Gly Phe Lys Leu Lys Phe Tyr
        435                 440                 445

Ala Lys Gly Leu Trp Ile Gly Leu Ile Cys Gly Ile Phe Cys Gln Ser
    450                 455                 460

Ser Ser Leu Leu Leu Met Thr Ile Phe Arg Lys Trp Thr Lys Leu Asn
465                 470                 475                 480

Val Ala Thr Val
```

<210> SEQ ID NO 15
<211> LENGTH: 507
<212> TYPE: PRT
<213> ORGANISM: Arabidopsis thaliana

<400> SEQUENCE: 15

```
Met Ser Ser Thr Glu Thr Tyr Glu Pro Leu Thr Arg Leu His Ser
 1               5                  10                  15

Asp Ser Gln Ile Thr Glu Arg Ser Pro Glu Ile Glu Phe Leu
            20                  25                  30

Arg Arg Arg Gly Ser Thr Val Thr Pro Arg Trp Trp Leu Lys Leu Ala
            35                  40                  45

Val Trp Glu Ser Lys Leu Leu Trp Thr Leu Ser Gly Ala Ser Ile Val
 50                  55                  60

Val Ser Val Leu Asn Tyr Met Leu Ser Phe Val Thr Val Met Phe Thr
 65                  70                  75                  80

Gly His Leu Gly Ser Leu Gln Leu Ala Gly Ala Ser Ile Ala Thr Val
                85                  90                  95

Gly Ile Gln Gly Leu Ala Tyr Gly Ile Met Leu Gly Met Ala Ser Ala
            100                 105                 110

Val Gln Thr Val Cys Gly Gln Ala Tyr Gly Ala Arg Gln Tyr Ser Ser
            115                 120                 125

Met Gly Ile Ile Cys Gln Arg Ala Met Val Leu His Leu Ala Ala Ala
            130                 135                 140

Val Phe Leu Thr Phe Leu Tyr Trp Tyr Ser Gly Pro Ile Leu Lys Thr
145                 150                 155                 160

Met Gly Gln Ser Val Ala Ile Ala His Glu Gly Gln Ile Phe Ala Arg
                165                 170                 175

Gly Met Ile Pro Gln Ile Tyr Ala Phe Ala Leu Ala Cys Pro Met Gln
            180                 185                 190

Arg Phe Leu Gln Ala Gln Asn Ile Val Asn Pro Leu Ala Tyr Met Ser
            195                 200                 205

Leu Gly Val Phe Leu Leu His Thr Leu Leu Thr Trp Leu Val Thr Asn
    210                 215                 220

Val Leu Asp Phe Gly Leu Leu Gly Ala Ala Leu Ile Leu Ser Phe Ser
225                 230                 235                 240

Trp Trp Leu Leu Val Ala Val Asn Gly Met Tyr Ile Leu Met Ser Pro
                245                 250                 255

Asn Cys Lys Glu Thr Trp Thr Gly Phe Ser Thr Arg Ala Phe Arg Gly
            260                 265                 270

Ile Trp Pro Tyr Phe Lys Leu Thr Val Ala Ser Ala Val Met Leu Cys
        275                 280                 285

Leu Glu Ile Trp Tyr Asn Gln Gly Leu Val Ile Ile Ser Gly Leu Leu
    290                 295                 300

Ser Asn Pro Thr Ile Ser Leu Asp Ala Ile Ser Ile Cys Met Tyr Tyr
305                 310                 315                 320

Leu Asn Trp Asp Met Gln Phe Met Leu Gly Leu Ser Ala Ala Ile Ser
                325                 330                 335

Val Arg Val Ser Asn Glu Leu Gly Ala Gly Asn Pro Arg Val Ala Met
            340                 345                 350

Leu Ser Val Val Val Asn Ile Thr Thr Val Leu Ile Ser Ser Val
        355                 360                 365

Leu Cys Val Ile Val Leu Val Phe Arg Val Gly Leu Ser Lys Ala Phe
    370                 375                 380
```

```
Thr Ser Asp Ala Glu Val Ile Ala Ala Val Ser Asp Leu Phe Pro Leu
385                 390                 395                 400

Leu Ala Val Ser Ile Phe Leu Asn Gly Ile Gln Pro Ile Leu Ser Gly
                405                 410                 415

Val Ala Ile Gly Ser Gly Trp Gln Ala Val Ala Tyr Val Asn Leu
            420                 425                 430

Val Thr Tyr Tyr Val Ile Gly Leu Pro Ile Gly Cys Val Leu Gly Phe
        435                 440                 445

Lys Thr Ser Leu Gly Val Ala Gly Ile Trp Trp Gly Met Ile Ala Gly
    450                 455                 460

Val Ile Leu Gln Thr Leu Thr Leu Ile Val Leu Thr Leu Lys Thr Asn
465                 470                 475                 480

Trp Thr Ser Glu Val Glu Asn Ala Ala Gln Arg Val Lys Thr Ser Ala
                485                 490                 495

Thr Glu Asn Gln Glu Met Ala Asn Ala Gly Val
                500                 505

<210> SEQ ID NO 16
<211> LENGTH: 536
<212> TYPE: PRT
<213> ORGANISM: Arabidopsis thaliana

<400> SEQUENCE: 16

Thr Leu Gln Gln Glu Ala Trp Gln Gln Gly Tyr Asp Ser His Asp Arg
1               5                   10                  15

Lys Arg Leu Leu Asp Glu Glu Arg Asp Leu Leu Ile Asp Asn Lys Leu
            20                  25                  30

Leu Ser Gln His Gly Asn Gly Gly Asp Ile Glu Ser His Gly His
        35                  40                  45

Gly Gln Ala Ile Gly Pro Asp Glu Glu Glu Arg Pro Ala Glu Ile Ala
    50                  55                  60

Asn Thr Trp Glu Ser Ala Ile Glu Ser Gly Gln Lys Ile Ser Thr Thr
65                  70                  75                  80

Phe Lys Arg Glu Thr Gln Val Ile Thr Met Asn Ala Leu Pro Leu Ile
                85                  90                  95

Phe Thr Phe Ile Leu Gln Asn Ser Leu Ser Leu Ala Ser Ile Phe Ser
                100                 105                 110

Val Ser His Leu Gly Thr Lys Glu Leu Gly Gly Val Thr Leu Gly Ser
            115                 120                 125

Met Thr Ala Asn Ile Thr Gly Leu Ala Ala Ile Gln Gly Leu Cys Thr
130                 135                 140

Cys Leu Asp Thr Leu Cys Ala Gln Ala Tyr Gly Ala Lys Asn Tyr His
145                 150                 155                 160

Leu Val Gly Val Leu Val Gln Arg Cys Ala Val Ile Thr Ile Leu Ala
                165                 170                 175

Phe Leu Pro Met Met Tyr Val Trp Phe Val Trp Ser Glu Lys Ile Leu
                180                 185                 190

Ala Leu Met Ile Pro Glu Arg Glu Leu Cys Ala Leu Ala Ala Asn Tyr
            195                 200                 205

Leu Arg Val Thr Ala Phe Gly Val Pro Gly Phe Ile Leu Phe Glu Cys
    210                 215                 220

Gly Lys Arg Phe Leu Gln Cys Gln Gly Ile Phe His Ala Ser Thr Ile
225                 230                 235                 240

Val Leu Phe Val Cys Ala Pro Leu Asn Ala Leu Met Asn Tyr Leu Leu
                245                 250                 255
```

Val Trp Asn Asp Lys Ile Gly Ile Gly Tyr Leu Gly Ala Pro Leu Ser
            260                 265                 270

Val Val Ile Asn Tyr Trp Leu Met Thr Leu Gly Leu Leu Ile Tyr Ala
            275                 280                 285

Met Thr Thr Lys His Lys Glu Arg Pro Leu Lys Cys Trp Asn Gly Ile
            290                 295                 300

Ile Pro Lys Glu Gln Ala Phe Lys Asn Trp Arg Lys Met Ile Asn Leu
305                 310                 315                 320

Ala Ile Pro Gly Val Val Met Val Glu Ala Glu Phe Leu Gly Phe Glu
                325                 330                 335

Val Leu Thr Ile Phe Ala Ser His Leu Gly Thr Asp Ala Leu Gly Ala
            340                 345                 350

Gln Ser Ile Val Ala Thr Ile Ala Ser Leu Ala Tyr Gln Val Pro Phe
            355                 360                 365

Ser Ile Ser Val Ser Thr Ser Thr Arg Val Ala Asn Phe Ile Gly Ala
            370                 375                 380

Ser Leu Tyr Asp Ser Cys Met Ile Thr Cys Arg Val Ser Leu Leu Leu
385                 390                 395                 400

Ser Phe Val Cys Ser Ser Met Asn Met Phe Val Ile Cys Arg Tyr Lys
                405                 410                 415

Glu Gln Ile Ala Ser Leu Phe Ser Thr Glu Ser Ala Val Val Lys Met
                420                 425                 430

Val Val Asp Thr Leu Pro Leu Leu Ala Phe Met Gln Leu Phe Asp Ala
            435                 440                 445

Phe Asn Ala Ser Thr Ala Gly Cys Leu Arg Gly Gln Gly Arg Gln Lys
450                 455                 460

Ile Gly Gly Tyr Ile Asn Leu Val Ala Phe Tyr Cys Leu Cys Val Pro
465                 470                 475                 480

Met Ala Tyr Val Leu Ala Phe Leu Tyr His Ile Gly Val Gly Leu Trp
                485                 490                 495

Leu Gly Thr Thr Ser Ala Leu Val Met Met Ser Val Cys Gln Gly Tyr
            500                 505                 510

Ala Val Pro His Gln Asp Arg Arg Ile Leu Gly Ala Ala Arg Lys
            515                 520                 525

Arg Asn Ala Glu Thr His Thr Ser
530                 535

<210> SEQ ID NO 17
<211> LENGTH: 456
<212> TYPE: PRT
<213> ORGANISM: Arabidopsis thaliana

<400> SEQUENCE: 17

Met His Arg Tyr Lys Glu Glu Ala Ser Ser Leu Ile Lys Leu Ala Thr
1               5                   10                  15

Pro Val Leu Ile Ala Ser Val Ala Gln Thr Gly Met Gly Phe Val Asp
            20                  25                  30

Thr Val Met Ala Gly Gly Val Thr Gln Thr Asp Met Ala Ala Val Ser
            35                  40                  45

Val Ala Ser Ser Ile Trp Leu Pro Ser Ile Leu Phe Gly Ile Gly Leu
            50                  55                  60

Leu Met Ala Leu Val Pro Val Ala Gln Leu Asn Gly Ser Ala Arg
65                  70                  75                  80

Arg Glu Lys Ile Pro Phe Glu Ile Gln Gln Gly Val Val Leu Ala Leu

```
                85                  90                  95
Leu Ile Ser Ile Pro Ile Ile Gly Val Leu Gln Thr Gln Phe Ile
            100                 105                 110
Leu Gln Leu Met Asp Val Glu Ala Val Met Ala Asp Lys Thr Val Gly
        115                 120                 125
Tyr Ile His Ala Val Ile Phe Ala Val Pro Ala Phe Leu Leu Phe Gln
    130                 135                 140
Thr Leu Arg Ser Phe Thr Asp Gly Met Ser Leu Thr Lys Pro Ala Met
145                 150                 155                 160
Val Ile Gly Phe Ile Gly Leu Leu Leu Asn Ile Pro Leu Asn Trp Ile
                165                 170                 175
Phe Val Tyr Gly Lys Phe Gly Ala Pro Glu Leu Gly Val Gly Cys
            180                 185                 190
Gly Val Ala Thr Thr Ile Val Tyr Trp Val Met Phe Ala Leu Leu Leu
        195                 200                 205
Ala Tyr Val Met Thr Ser Ser Arg Leu Lys Ser Ile Asn Val Phe Gly
    210                 215                 220
Glu Tyr His Lys Pro Gln Trp Lys Ala Gln Val Arg Leu Phe Lys Leu
225                 230                 235                 240
Gly Phe Pro Val Ala Ala Leu Phe Phe Glu Val Thr Leu Phe Ala
            245                 250                 255
Val Val Ala Leu Leu Val Ser Pro Leu Gly Pro Ile Ile Val Ala Ala
        260                 265                 270
His Gln Val Ala Ile Asn Phe Ser Ser Leu Val Phe Met Leu Pro Met
    275                 280                 285
Ser Val Gly Ala Ala Val Ser Ile Arg Val Gly His Arg Leu Gly Glu
    290                 295                 300
Glu Asn Val Asp Gly Ala Arg Val Ala Ser Arg Val Gly Ile Met Val
305                 310                 315                 320
Gly Leu Ala Leu Ala Thr Ile Thr Ala Ile Ile Thr Val Leu Ser Arg
                325                 330                 335
Glu Leu Ile Ala Glu Leu Tyr Thr Asn Asn Pro Glu Val Ile Thr Leu
            340                 345                 350
Ala Met Gln Leu Leu Leu Phe Ala Ala Val Tyr Gln Cys Thr Asp Ala
        355                 360                 365
Val Gln Val Ile Ala Ala Gly Ala Leu Arg Gly Tyr Lys Asp Met Arg
    370                 375                 380
Ala Ile Phe Asn Arg Thr Phe Ile Ala Tyr Trp Ile Leu Gly Leu Pro
385                 390                 395                 400
Thr Gly Tyr Ile Leu Gly Arg Thr Asp Trp Ile Val Glu Pro Met Gly
                405                 410                 415
Ala Gln Gly Phe Trp Leu Gly Phe Ile Ile Gly Leu Thr Ala Ala Ala
            420                 425                 430
Leu Met Leu Gly Val Arg Leu Arg Trp Met His Arg Gln Glu Pro Asp
        435                 440                 445
Val Gln Leu Asn Phe Ser Leu Gln
    450                 455

<210> SEQ ID NO 18
<211> LENGTH: 457
<212> TYPE: PRT
<213> ORGANISM: Arabidopsis thaliana

<400> SEQUENCE: 18
```

-continued

```
Met Gln Lys Tyr Ile Ser Glu Ala Arg Leu Leu Ala Leu Ala Ile
  1               5                  10                  15

Pro Val Ile Leu Ala Gln Ile Ala Gln Thr Ala Met Gly Phe Val Ser
             20                  25                  30

Thr Val Met Ala Gly Gly Tyr Ser Ala Thr Asp Met Ala Ala Val Ala
         35                  40                  45

Ile Gly Thr Ser Ile Trp Leu Pro Ala Ile Leu Phe Gly His Gly Leu
     50                  55                  60

Leu Leu Ala Leu Thr Pro Val Ile Ala Gln Leu Asn Gly Ser Gly Arg
 65              70                  75                      80

Arg Glu Arg Ile Ala His Gln Val Arg Gln Gly Phe Trp Leu Ala Gly
                 85                  90                  95

Phe Val Ser Val Leu Ile Met Leu Val Leu Trp Asn Ala Gly Tyr Ile
             100                 105                 110

Ile Arg Ser Met Glu Asn Ile Asp Pro Ala Leu Ala Asp Lys Ala Val
         115                 120                 125

Gly Tyr Leu Arg Ala Leu Leu Trp Gly Ala Pro Gly Tyr Leu Phe Phe
     130                 135                 140

Gln Val Ala Arg Asn Gln Cys Glu Gly Leu Ala Lys Thr Lys Pro Gly
145                 150                 155                 160

Met Val Met Gly Phe Ile Gly Leu Leu Val Asn Ile Pro Val Asn Tyr
                 165                 170                 175

Ile Phe Ile Tyr Gly His Phe Gly Met Pro Glu Leu Gly Gly Val Gly
             180                 185                 190

Cys Gly Val Ala Thr Ala Ala Val Tyr Trp Val Met Phe Leu Ala Met
         195                 200                 205

Val Ser Tyr Ile Lys Arg Ala Arg Ser Met Arg Asp Ile Arg Asn Glu
 210                 215                 220

Lys Gly Thr Ala Lys Pro Asp Pro Ala Val Met Lys Arg Leu Ile Gln
225                 230                 235                 240

Leu Gly Leu Pro Ile Ala Leu Ala Leu Phe Phe Glu Val Thr Leu Phe
                 245                 250                 255

Ala Val Val Ala Leu Leu Val Ser Pro Leu Gly Ile Val Asp Val Ala
             260                 265                 270

Gly His Gln Ile Ala Leu Asn Phe Ser Ser Leu Met Phe Val Leu Pro
         275                 280                 285

Met Ser Leu Ala Ala Ala Val Thr Ile Arg Val Gly Tyr Arg Leu Gly
 290                 295                 300

Gln Gly Ser Thr Leu Asp Ala Gln Thr Ala Ala Arg Thr Gly Leu Met
305                 310                 315                 320

Val Gly Val Cys Met Ala Thr Leu Thr Ala Ile Phe Thr Val Ser Leu
                 325                 330                 335

Arg Glu Gln Ile Ala Leu Leu Tyr Asn Asp Asn Pro Glu Val Val Thr
             340                 345                 350

Leu Ala Ala His Leu Met Leu Leu Ala Ala Val Tyr Gln Ile Ser Asp
         355                 360                 365

Ser Ile Gln Val Ile Gly Ser Gly Ile Leu Arg Gly Tyr Lys Asp Thr
 370                 375                 380

Arg Ser Ile Phe Tyr Ile Thr Phe Thr Ala Tyr Trp Val Leu Gly Leu
385                 390                 395                 400

Pro Ser Gly Tyr Ile Leu Ala Leu Thr Asp Leu Val Val Glu Pro Met
                 405                 410                 415

Gly Pro Ala Gly Phe Trp Ile Gly Phe Ile Ile Gly Leu Thr Ser Ala
```

```
                     420                 425                 430
Ala Ile Met Met Met Leu Arg Met Arg Phe Leu Gln Arg Leu Pro Ser
            435                 440                 445
Ala Ile Ile Leu Gln Arg Ala Ser Arg
            450                 455

<210> SEQ ID NO 19
<211> LENGTH: 459
<212> TYPE: PRT
<213> ORGANISM: Arabidopsis thaliana

<400> SEQUENCE: 19

Met Pro Pro Gly Val Ala Val Cys Phe Ser Ser Leu Phe Ile Arg Leu
  1               5                  10                  15

Val Cys Met Ala Phe Leu Thr Ser Ser Asp Lys Ala Leu Trp His Leu
             20                  25                  30

Ala Leu Pro Met Ile Phe Ser Asn Ile Thr Val Pro Leu Leu Gly Leu
         35                  40                  45

Val Asp Thr Ala Val Ile Gly His Leu Asp Ser Pro Val Tyr Leu Gly
     50                  55                  60

Gly Val Ala Val Gly Ala Thr Ala Thr Ser Phe Leu Phe Met Leu Leu
 65                  70                  75                  80

Leu Phe Leu Arg Met Ser Thr Thr Gly Leu Thr Ala Gln Ala Tyr Gly
                 85                  90                  95

Ala Lys Asn Pro Gln Ala Leu Ala Arg Thr Leu Val Gln Pro Leu Leu
            100                 105                 110

Leu Ala Leu Gly Ala Gly Ala Leu Ile Ala Leu Leu Arg Thr Pro Ile
        115                 120                 125

Ile Asp Leu Ala Leu His Ile Val Gly Gly Ser Glu Ala Val Leu Glu
    130                 135                 140

Gln Ala Arg Arg Phe Leu Glu Ile Arg Trp Leu Ser Ala Pro Ala Ser
145                 150                 155                 160

Leu Ala Asn Leu Val Leu Leu Gly Trp Leu Leu Gly Val Gln Tyr Ala
                165                 170                 175

Arg Ala Pro Val Ile Leu Leu Val Gly Asn Ile Leu Asn Ile Val
            180                 185                 190

Leu Asp Val Trp Leu Val Met Gly Leu His Met Asn Val Gln Gly Ala
        195                 200                 205

Ala Leu Ala Thr Val Ile Ala Glu Tyr Ala Thr Leu Leu Ile Gly Leu
    210                 215                 220

Leu Met Val Arg Lys Ile Leu Lys Leu Arg Gly Ile Ser Gly Glu Met
225                 230                 235                 240

Leu Lys Thr Ala Trp Arg Gly Asn Phe Arg Arg Leu Leu Ala Leu Asn
                245                 250                 255

Arg Asp Ile Met Leu Arg Ser Leu Leu Leu Gln Leu Cys Phe Gly Ala
            260                 265                 270

Ile Thr Val Leu Gly Ala Arg Leu Gly Ser Asp Ile Ile Ala Val Asn
        275                 280                 285

Ala Val Leu Met Thr Leu Leu Thr Phe Thr Ala Tyr Ala Leu Asp Gly
    290                 295                 300

Phe Ala Tyr Ala Val Glu Ala His Ser Gly Gln Ala Tyr Gly Ala Arg
305                 310                 315                 320

Asp Gly Ser Gln Leu Leu Asp Val Trp Arg Ala Ala Cys Arg Gln Ser
                325                 330                 335
```

-continued

| | | | | | | | | | | | |
|---|---|---|---|---|---|---|---|---|---|---|---|
|Gly|Ile|Val|Ala|Leu|Leu|Phe|Ser|Val|Val|Tyr|Leu Leu Ala Gly Glu|
| | | |340| | |345| | | |350| |

His Ile Ile Ala Leu Leu Thr Ser Leu Thr Gln Ile Gln Gln Leu Ala
        355                 360                 365

Asp Arg Tyr Leu Ile Trp Gln Val Ile Leu Pro Val Gly Val Trp
    370                 375                 380

Cys Tyr Leu Leu Asp Gly Met Phe Ile Gly Ala Thr Arg Ala Thr Glu
385                 390                 395                 400

Met Arg Asn Ser Met Ala Val Ala Ala Ala Gly Phe Ala Leu Thr Leu
                405                 410                 415

Leu Thr Leu Pro Trp Leu Gly Asn His Ala Leu Trp Leu Ala Leu Thr
                420                 425                 430

Val Phe Leu Ala Leu Arg Gly Leu Ser Leu Ala Ala Ile Trp Arg Arg
            435                 440                 445

His Trp Arg Asn Gly Thr Trp Phe Ala Ala Thr
    450                 455

<210> SEQ ID NO 20
<211> LENGTH: 1868
<212> TYPE: DNA
<213> ORGANISM: Arabidopsis thaliana
<220> FEATURE:
<221> NAME/KEY: CDS
<222> LOCATION: (118)...(1695)

<400> SEQUENCE: 20

```
aaataatccc ctctaaactc tcctagatac tcactcatca ctactcatct caagttcacg      60
tgactactta tataagcgtt gactacataa agagacagtt acagaggaaa aagatct atg    120
                                                                  Met
                                                                    1 acg gaa act ggt gat gat ctt gct acg gtg aag aag cca atc cca ttt      168
Thr Glu Thr Gly Asp Asp Leu Ala Thr Val Lys Lys Pro Ile Pro Phe
            5                   10                  15 ctc gtt atc ttc aaa gat tta aga cat gta ttc agt agg gac aca act      216
Leu Val Ile Phe Lys Asp Leu Arg His Val Phe Ser Arg Asp Thr Thr
         20                  25                  30 ggg cga gag att cta ggc atc gcg ttt cca gca gct ttg gct tta gct      264
Gly Arg Glu Ile Leu Gly Ile Ala Phe Pro Ala Ala Leu Ala Leu Ala
     35                  40                  45 gct gat cca atc gct tct ctg att gat acc gct ttt gtc ggg cgt tta      312
Ala Asp Pro Ile Ala Ser Leu Ile Asp Thr Ala Phe Val Gly Arg Leu
 50                  55                  60                  65 gga gcg gtt cag cta gcg gcg gtt gga gtt tcc att gcc ata ttc aat      360
Gly Ala Val Gln Leu Ala Ala Val Gly Val Ser Ile Ala Ile Phe Asn
                 70                  75                  80 caa gct tct aga att acg ata ttc cca ctt gtg agc ctc aca act tca      408
Gln Ala Ser Arg Ile Thr Ile Phe Pro Leu Val Ser Leu Thr Thr Ser
             85                  90                  95 ttt gtg gca gag gaa gac acg atg gag aag atg aaa gaa gaa gca aac      456
Phe Val Ala Glu Glu Asp Thr Met Glu Lys Met Lys Glu Glu Ala Asn
        100                 105                 110 aaa gcc aat ctt gtt cat gca gaa act ata ctt gtt caa gat tct ttg      504
Lys Ala Asn Leu Val His Ala Glu Thr Ile Leu Val Gln Asp Ser Leu
    115                 120                 125 gaa aag ggc att tct tca cct aca agt aac gat acc aac cag cca cag      552
Glu Lys Gly Ile Ser Ser Pro Thr Ser Asn Asp Thr Asn Gln Pro Gln
130                 135                 140                 145 caa cct cca gct ccg gat aca aag tca aat agc gga aac aaa tcg aat      600
Gln Pro Pro Ala Pro Asp Thr Lys Ser Asn Ser Gly Asn Lys Ser Asn
```

-continued 150              155              160
aaa aag gag aag agg acc att aga aca gca tca aca gct atg atc ttg        648
Lys Lys Glu Lys Arg Thr Ile Arg Thr Ala Ser Thr Ala Met Ile Leu
            165              170              175 ggg tta atc ctt ggc ctt gtg caa gct att ttc ttg att ttc agt tca        696
Gly Leu Ile Leu Gly Leu Val Gln Ala Ile Phe Leu Ile Phe Ser Ser
        180              185              190 aag ttg ctt cta ggc gtc atg gga gtg aaa cca aat tca cca atg tta        744
Lys Leu Leu Leu Gly Val Met Gly Val Lys Pro Asn Ser Pro Met Leu
    195              200              205 tca cca gca cac aag tac ttg agc ata cga gct ttg ggg gct cct gca        792
Ser Pro Ala His Lys Tyr Leu Ser Ile Arg Ala Leu Gly Ala Pro Ala
210              215              220              225 ttg ctt cta tct ctt gct atg caa ggc atc ttt cgt gga ttc aag gac        840
Leu Leu Leu Ser Leu Ala Met Gln Gly Ile Phe Arg Gly Phe Lys Asp
            230              235              240 acc aaa act cct ctc ttt gcc act gtc gta gca gat gtt atc aac ata        888
Thr Lys Thr Pro Leu Phe Ala Thr Val Val Ala Asp Val Ile Asn Ile
        245              250              255 gtt ctc gac ccc atc ttc att ttt gtg ctt cgt cta ggg atc atc ggt        936
Val Leu Asp Pro Ile Phe Ile Phe Val Leu Arg Leu Gly Ile Ile Gly
    260              265              270 gca gcc att gcc cat gtc att tct cag tac ttc atg act cta ata ttg        984
Ala Ala Ile Ala His Val Ile Ser Gln Tyr Phe Met Thr Leu Ile Leu
275              280              285 ttc gtc ttc ctc gca aag aaa gtt aat ttg att cca cca aac ttc ggg       1032
Phe Val Phe Leu Ala Lys Lys Val Asn Leu Ile Pro Pro Asn Phe Gly
            290              295              300              305 gat ttg cag ttt gga agg ttc ctt aaa aat ggg cta cta ttg ctg gcg       1080
Asp Leu Gln Phe Gly Arg Phe Leu Lys Asn Gly Leu Leu Leu Ala
        310              315              320 agg acc ata gca gtg acg ttt tgt cag acc tta gca gca gca atg gcg       1128
Arg Thr Ile Ala Val Thr Phe Cys Gln Thr Leu Ala Ala Ala Met Ala
    325              330              335 gcg cgg ctg ggt aca aca cca atg gct gct ttt cag att tgt tta caa       1176
Ala Arg Leu Gly Thr Thr Pro Met Ala Ala Phe Gln Ile Cys Leu Gln
340              345              350 gta tgg tta act tct tct ctt ctc aat gat ggt ctt gcc gtt gct ggt       1224
Val Trp Leu Thr Ser Ser Leu Leu Asn Asp Gly Leu Ala Val Ala Gly
355              360              365 cag gcg att ctg gct tgt tcg ttt gct gag aag gac tat aac aaa gtg       1272
Gln Ala Ile Leu Ala Cys Ser Phe Ala Glu Lys Asp Tyr Asn Lys Val
370              375              380              385 act gct gtt gca tcc cgt gtt cta cag atg ggt ttt gtg tta gga ctt       1320
Thr Ala Val Ala Ser Arg Val Leu Gln Met Gly Phe Val Leu Gly Leu
            390              395              400 gga ctg tcc gtt ttt gtt gga cta ggt ctc tac ttt ggt gcc gga gtt       1368
Gly Leu Ser Val Phe Val Gly Leu Gly Leu Tyr Phe Gly Ala Gly Val
        405              410              415 ttc tcc aag gac cct gct gtt att cac ctc atg gcc atc gga ata ccg       1416
Phe Ser Lys Asp Pro Ala Val Ile His Leu Met Ala Ile Gly Ile Pro
    420              425              430 ttt ata gca gca acg cag cca ata aac tct ctc gcc ttt gta ttg gat       1464
Phe Ile Ala Ala Thr Gln Pro Ile Asn Ser Leu Ala Phe Val Leu Asp
435              440              445 gga gtc aat ttt gga gca tct gat ttt gct tac act gca tac tcc atg       1512
Gly Val Asn Phe Gly Ala Ser Asp Phe Ala Tyr Thr Ala Tyr Ser Met
450              455              460              465 gtg gga gtg gcg gcc ata agc att gca gca gta ata tat atg gca aag       1560

```
Val Gly Val Ala Ala Ile Ser Ile Ala Ala Val Ile Tyr Met Ala Lys
            470             475             480 acc aat ggt ttc ata gga ata tgg ata gct ctt aca atc tat atg gct    1608
Thr Asn Gly Phe Ile Gly Ile Trp Ile Ala Leu Thr Ile Tyr Met Ala
            485             490             495 ctc cgg gct att act gga att gcc agg atg gcg aca gga act gga ccg    1656
Leu Arg Ala Ile Thr Gly Ile Ala Arg Met Ala Thr Gly Thr Gly Pro
            500             505             510 tgg agg ttc ttg cgt gga cga tca tcc tct tca tct tcc taggacttag     1705
Trp Arg Phe Leu Arg Gly Arg Ser Ser Ser Ser Ser Ser
            515             520             525 tttatttata acgagttgca tctcttcttc cttcttcgtt tttgtttatg gttcttgtgt  1765
ttgtttttca acattttgtt cgagagaccg ttatcatatt atcagtttca cataaataat  1825
gcatattttt aagtcattaa aataaaaaaa aaaaaaaaaa aaa                    1868
```